US012655450B1

(12) United States Patent
Hill et al.

(10) Patent No.: US 12,655,450 B1
(45) Date of Patent: Jun. 16, 2026

(54) METHODS, SYSTEMS, AND KITS FOR DETECTION OF NUCLEIC ACID MOLECULES

(71) Applicant: 10x Genomics, Inc., Pleasanton, CA (US)

(72) Inventors: Andrew John Hill, Oakland, CA (US); Katherine Pfeiffer, Oakland, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 1199 days.

(21) Appl. No.: 17/512,241

(22) Filed: Oct. 27, 2021

Related U.S. Application Data

(60) Provisional application No. 63/106,186, filed on Oct. 27, 2020.

(51) Int. Cl.

| | |
|---|---|
| *C12N 15/90* | (2006.01) |
| *C12N 9/22* | (2006.01) |
| *C12N 15/11* | (2006.01) |
| *C12Q 1/6806* | (2018.01) |
| *C12Q 1/6813* | (2018.01) |

(52) U.S. Cl.
CPC .............. *C12N 15/90* (2013.01); *C12N 9/22* (2013.01); *C12N 15/111* (2013.01); *C12Q 1/6806* (2013.01); *C12Q 1/6813* (2013.01); *C12N 2310/20* (2017.05)

(58) Field of Classification Search
CPC ........ C12N 15/90; C12N 9/22; C12N 15/111; C12N 2310/20; C12Q 1/6806; C12Q 1/6813
See application file for complete search history.

(56) References Cited

U.S. PATENT DOCUMENTS

| | | | |
|---|---|---|---|
| 4,124,638 | A | 11/1978 | Hansen |
| 5,185,099 | A | 2/1993 | Delpuech et al. |
| 5,270,183 | A | 12/1993 | Corbett et al. |
| 5,478,893 | A | 12/1995 | Ghosh et al. |
| 5,736,330 | A | 4/1998 | Fulton |
| 5,756,334 | A | 5/1998 | Perler et al. |
| 5,846,719 | A | 12/1998 | Brenner et al. |
| 5,900,481 | A | 5/1999 | Lough et al. |
| 5,942,609 | A | 8/1999 | Hunkapiller et al. |
| 5,994,056 | A | 11/1999 | Higuchi |
| 6,033,880 | A | 3/2000 | Haff et al. |
| 6,057,149 | A | 5/2000 | Burns et al. |
| 6,123,798 | A | 9/2000 | Gandhi et al. |
| 6,171,850 | B1 | 1/2001 | Nagle et al. |
| 6,172,218 | B1 | 1/2001 | Brenner |
| 6,176,962 | B1 | 1/2001 | Soane et al. |
| 6,265,552 | B1 | 7/2001 | Schatz |
| 6,306,590 | B1 | 10/2001 | Mehta et al. |
| 6,327,410 | B1 | 12/2001 | Walt et al. |
| 6,379,929 | B1 | 4/2002 | Burns et al. |
| 6,406,848 | B1 | 6/2002 | Bridgham et al. |
| 6,409,832 | B2 | 6/2002 | Weigl et al. |
| 6,492,118 | B1 | 12/2002 | Abrams et al. |
| 6,524,456 | B1 | 2/2003 | Ramsey et al. |
| 6,586,176 | B1 | 7/2003 | Trnovsky et al. |
| 6,632,655 | B1 | 10/2003 | Mehta et al. |
| 6,915,679 | B2 | 7/2005 | Chien et al. |
| 7,041,481 | B2 | 5/2006 | Anderson et al. |
| 7,115,400 | B1 | 10/2006 | Adessi et al. |
| 7,129,091 | B2 | 10/2006 | Ismagilov et al. |
| 7,268,167 | B2 | 9/2007 | Higuchi et al. |
| 7,282,370 | B2 | 10/2007 | Bridgham et al. |
| 7,294,503 | B2 | 11/2007 | Quake et al. |
| 7,323,305 | B2 | 1/2008 | Leamon et al. |
| 7,544,473 | B2 | 6/2009 | Brenner |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

Biswas, S. et. al., Theoretical and Applied Genetics, vol. 133, Issue 8, p. 2323-2334 (published online May 14, 2020) (Year: 2020).*
Bowling, S., et al., Cell, vol. 181, Issue 6, p. 1410-1422, (Jun. 11, 2020) (Year: 2020).*
Georgiadis, C. et al., Molecular Therapy, vol. 26, Issue 5, p. 1215-1227 (Mar. 6, 2018). (Year: 2018).*
Wang, F. et al., The Journal of Molecular Diagnostics, vol. 14, Issue 1, p. 22-29 (Jan. 2012) (Year: 2012).*
Severins, I. et al., Biophysical Journal, vol. 115, p. 957-967, published Sep. 18, 2018 (Year: 2018).*
10X Genomics, Inc. CG000153 Rev A. Chromium Single Cell DNA Reagent Kits User Guide. 2018.

(Continued)

*Primary Examiner* — Neil P Hammell
*Assistant Examiner* — Krishna N Ravindra
(74) *Attorney, Agent, or Firm* — WILSON SONSINI GOODRICH & ROSATI

(57) ABSTRACT

The present disclosure provides methods, systems, and kits for processing or analyzing a sample. Processing a sample may comprise hybridizing a probe molecule to a binding region of a nucleic acid molecule, barcoding the probe-nucleic acid molecule complex, and performing extension, denaturation, and amplification processes. A target nucleic acid molecule in the present disclosure may comprise a CRISPR guide nucleic acid molecule or other molecule used with gene editing. Processing a sample may comprise hybridizing first and second probes to adjacent or non-adjacent binding regions of a nucleic acid molecule, linking the first and second probes to provide a probe-linked nucleic acid molecule, and barcoding the probe-linked nucleic acid molecule. One or more processes of the methods described herein may be performed within a partition, such as a droplet or well. One or more processes of the methods described herein may be performed on a cell, such as a permeabilized cell.

24 Claims, 36 Drawing Sheets

(56)  References Cited

U.S. PATENT DOCUMENTS

| | | | |
|---|---|---|---|
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,709,197 B2 | 5/2010 | Drmanac |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,370 B2 | 4/2015 | Hong |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,550,429 B2 | 2/2020 | Harada et al. |
| 10,557,158 B2 | 2/2020 | Hardenbol et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,920,183 B2 | 3/2024 | Bharadwaj et al. |
| 11,952,626 B2 | 4/2024 | Pfeiffer et al. |
| 12,065,688 B2 | 8/2024 | Bell |
| 12,084,715 B1 | 9/2024 | Lund |
| 12,163,179 B2 | 12/2024 | Bell et al. |
| 12,169,198 B2 | 12/2024 | Price et al. |
| 12,188,014 B1 | 1/2025 | Price et al. |
| 12,235,262 B1 | 2/2025 | Giresi |
| 12,398,262 B1 | 8/2025 | Gibbons |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |

(56) References Cited

U.S. PATENT DOCUMENTS

| | | |
|---|---|---|
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0133344 A1 | 5/2015 | Shendure et al. |
| 2015/0267191 A1 | 9/2015 | Steelman et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0073073 A1 | 3/2018 | Fu et al. |
| 2018/0080075 A1 | 3/2018 | Brenner et al. |
| 2018/0105808 A1 | 4/2018 | Mikkelsen et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367969 A1 | 12/2019 | Belhocine et al. |
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0403375 A1 | 12/2022 | Alvarado Martinez |
| 2023/0167496 A1 | 6/2023 | Bava |
| 2024/0002914 A1 | 1/2024 | Pfeiffer et al. |
| 2024/0272044 A1 | 8/2024 | Bava |
| 2025/0250612 A1 | 8/2025 | Smibert et al. |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015164212 A1 | 10/2015 |

(56) References Cited

FOREIGN PATENT DOCUMENTS

| | | |
|---|---|---|
| WO | WO-2016040476 A1 | 3/2016 |
| WO | WO-2016061517 A2 | 4/2016 |
| WO | WO-2016126871 A2 | 8/2016 |
| WO | WO-2016168584 A1 | 10/2016 |
| WO | WO-2017015075 A1 | 1/2017 |
| WO | WO-2017066231 A1 | 4/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018075693 A1 | 4/2018 |
| WO | WO-2018091676 A1 | 5/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019071039 A1 | 4/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021222301 A1 | 11/2021 |
| WO | WO-2021222302 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |
| WO | WO-2024243444 A1 | 11/2024 |

OTHER PUBLICATIONS

10X Genomics, Inc. CG000184 Rev A. Chromium Single Cell 3' Reagent Kits v3 User Guide with Feature Barcoding Technology for CRISPR Screening. 2018.

10X Genomics, Inc. CG000185 Rev B. Chromium Single Cell 3' Reagent Kits User Guide with Feature Barcoding Technology for Cell Surface Protein. 2018.

10X Genomics, Inc. CG000208 Rev E. Chromium Next GEM Single Cell V(D)J reagent Kits v1.1 User Guide with Feature Barcode Technology for Cell Surface Protein. 2020.

10X Genomics, Inc. CG000209 Rev D. Chromium Next GEM Single Cell ATAC Reagent Kits v1.1 User Guide. 2020.

10X Genomics, Inc. CG000239 Rev B. Visium Spatial Gene Expression Reagent Kits User Guide. 2020.

10X Genomics, Inc. CG00026. Chromium Single Cell 3' Reagent Kit User Guide. 2016.

10X Genomics, Inc. LIT00003 Rev B Chromium Genome Solution Application Note. 2017.

Abate, A.R. et al. "Beating Poisson encapsulation statistics using close-packed ordering" Lab on a Chip (Sep. 21, 2009) 9(18):2628-2631.

Adamson et al., "Production of arrays of chemically distinct nanolitre plugs via repeated splitting in microfluidic devices", Lab Chip 6(9): 1178-1186 (Sep. 2006).

Agasti, S.S. et al. "Photocleavable DNA barcode-antibody conjugates allow sensitive and multiplexed protein analysis in single cell" J Am Chem Soc (2012) 134(45):18499-18502.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Boulanger, et al, "Massively parallel haplotyping on microscopic beads for the high-throughput phase analysis of single molecules", PLoS One, vol. 7:1-10, 2012.

Braeckmans et al., Scanning the Code. Modern Drug Discovery. 2003:28-32.

Brenner, et al. "In vitro cloning of complex mixtures of DNA on microbeads: physical separation of differentially expressed cDNAs." Proc Natl Acad Sci U S A. Feb. 15, 2000;97(4):1665-70.

Brown, K., Targeted Sequencing Using Droplet-Based Microfluidics, RainDance Technologies, 2009, 1-18.

Browning, et al. Haplotype phasing: existing methods and new developments. Nat Rev Genet. Sep. 16, 2011;12(10):703-14. doi: 10.1038/nrg3054. Review.

Buchman GW, et al. Selective RNA amplification: a novel method using dUMP-containing primers and uracil DNA glycosylase. PCR Methods Appl. Aug. 1993; 3(1):28-31.

Burns, et al. An Integrated Nanoliter DNA Analysis Device. Science. Oct. 16, 1998;282(5388):484-7.

Burns, et al. Microfabricated structures for integrated DNA analysis. Proc Natl Acad Sci U S A. May 28, 1996; 93(11): 5556-5561.

Burns, et al. The intensification of rapid reactions in multiphase systems using slug flow in capillaries. Lab Chip. Sep. 2001;1(1):10-15. Epub Aug. 9, 2001.

Chen, et al. Chemical transfection of cells in picoliter aqueous droplets in fluoro carbon oil. Anal Chem. Nov. 15, 2011;83(22):8816-20. doi: 10.1021/ac2022794. Epub Oct. 17, 2011.

Chien et al. "Multiport flow-control system for lab-on-a-chip microfluidic devices", Fresenius J. Anal Chem, 371:106-111 (Jul. 27, 2001).

Chu, et al. Controllable monodisperse multiple emulsions. Angew Chem Int Ed Engl. 2007;46(47):8970-4.

Clausell-Tormos et al., "Droplet-based microfluidic platforms for the encapsulation and screening of mammalian cells and multicellular organisms", Chem. Biol. 15:427-437 (2008).

Co-pending U.S. Appl. No. 16/434,076, inventor Giresi; Paul, filed on Jun. 6, 2019.

Co-pending U.S. Appl. No. 16/434,084, inventor Giresi; Paul, filed on Jun. 6, 2019.

Co-pending U.S. Appl. No. 16/434,102, inventors Price; Andrew D. et al., filed on Jun. 6, 2019.

Co-pending U.S. Appl. No. 16/708,214, inventors Wheeler; Tobias Daniel et al., filed on Dec. 9, 2019.

Co-pending U.S. Appl. No. 16/737,762, inventors Price; Andrew D. et al., filed on Jan. 8, 2020.

Co-pending U.S. Appl. No. 16/737,770, inventors Belhocine; Zahara Kamila et al., filed on Jan. 8, 2020.

Co-pending U.S. Appl. No. 16/789,273, inventors Maheshwari; Arundhati Shamoni et al., filed on Feb. 12, 2020.

Co-pending U.S. Appl. No. 16/800,450, inventor Katherine; Pfeiffer, filed on Feb. 25, 2020.

Co-pending U.S. Appl. No. 17/014,909, inventor Giresi; Paul, filed on Sep. 8, 2020.

(56) References Cited

OTHER PUBLICATIONS

Co-pending U.S. Appl. No. 17/148,942, inventors Mcdermott; Geoffrey et al., filed on Jan. 14, 2021.

Co-pending U.S. Appl. No. 17/166,982, inventors Mcdermott; Geoffrey et al., filed on Feb. 3, 2021.

Co-pending U.S. Appl. No. 17/175,542, inventors Maheshwari; Arundhati Shamoni et al., filed on Feb. 12, 2021.

Co-pending U.S. Appl. No. 17/220,303, inventor Walter; Dagmar, filed on Apr. 1, 2021.

Co-pending U.S. Appl. No. 17/381,612, inventor Martinez; Luigi Jhon Alvarado, filed on Jul. 21, 2021.

Co-pending U.S. Appl. No. 17/499,039, inventors Pfeiffer; Katherine et al., filed on Oct. 12, 2021.

Co-pending U.S. Appl. No. 17/522,741, inventors Zheng; Xinying et al., filed on Nov. 9, 2021.

CRISP-Seq Barcoded sgRNA Libraries (Perturb-Seq, CROP-Seq), Cellecta, Inc., 2021, Webpage accessed at https://cellecta.com/collections/crispr-seq-barcoded-sgrna-libraries-perturb-seq-crop-seq.

Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.

Datlinger et al. Pooled CRISPR screening with single-cell transcriptome readout. Nature Methods Advance Online Publication (Jan. 18, 2017). DOI: http://www.nature.com/doifinder/10.1038/nmeth.4177. 10 pages.

Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Drmanac et al., Sequencing by hybridization (SBH): advantages, achievements, and opportunities. Adv Biochem Eng Biotechnol. 2002;77 :75-101.

Duffy et al., Rapid Protyping of Microfluidic Systems and Polydimethylsiloxane, Anal Chem 70:4974-4984 (1998).

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Esser-Kahn, et al. Triggered release from polymer capsules. Macromolecules. 2011; 44:5539-5553.

Fan, et al. Noninvasive diagnosis of fetal aneuploidy by shotgun sequencing DNA from maternal blood. Proc Natl Acad Sci U S A. Oct. 21, 2008;105(42): 16266-71. Epub Oct. 6, 2008.

Fan, et al. Whole-genome molecular haplotyping of single cells. Nature Biotechnology, vol. 29, No. 1. Jan. 1, 2011. pp. 51-59.

Fang, et al. Fluoride-cleavable biotinylation phosphoramidite for 5'-end-labeling and affinity purification of synthetic oligonucleotides. Nucleic Acids Res. Jan. 15, 2003;31(2):708-15.

Frampton, G.M. et al. "Development and validation of a clinical cancer genomic profiling test based on massively parallel DNA sequencing" Nature Biotechnology (2013) 31(11):1023-1031. doi: 10.1038/nbr.2696.

Gericke, et al. Functional cellulose beads: preparation, characterization, and applications. Chemical reviews 113.7 (2013): 4812-4836.

Guo, et al. Droplet microfluidics for high-throughput biological assays. Lab Chip. Jun. 21, 2012;12(12):2146-55. doi: 10.1039/c2lc21147e. Epub Feb. 9, 2012.

Gyarmati, et al. Reversible disulphide formation in polymer networks: a versatile functional group from synthesis to applications. European Polymer Journal. 2013; 49:1268-1286.

Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.

Hill et al., On the design of CRISPR-based single-cell molecular screens, Nature Methods, vol. 15, No. 4; pp. 271-274, Feb. 19, 2018.

Holtze, et al. Biocompatible surfactants for water-in-fluorocarbon emulsions. Lab Chip. Oct. 2008;8(10):1632-9. doi: 10.1039/b806706f. Epub Sep. 2, 2008.

Hosokawa, et al. Massively parallel whole genome amplification for single-cell sequencing using droplet microfluidics. Scientific Reports 7, Article No. 5199 (2017).

Hug, et al. Measurement of the No. of molecules of a single mRNA species in a complex mRNA preparation. J Theor Biol. Apr. 21, 2003;221(4):615-24.

Hughes, et al. Choose your label wisely: water-soluble fluorophores often interact with lipid bilayers. PloS one 9.2 (2014): e87649.

Islam, et al. Highly multiplexed and strand-specific single-cell RNA 5' end sequencing. Nat Protoc. Apr. 5, 2012;7(5):813-28. doi: 10.1038/nprot.2012.022.

Jaitin, et al. Massively parallel single-cell RNA-seq for marker-free decomposition of tissues into cell types. Science. Feb. 14, 2014;343(6172):776-9. doi: 10.1126/science.1247651.

Jarosz, M. et al. "Using 1ng of DNA to detect haplotype phasing and gene fusions from whole exome sequencing of cancer cell lines" Cancer Res (2015) 75(suppl15):4742.

Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad SciU S A. Apr. 2, 2013;110(14):5552-7. doi: 10.1073/pnas.1218696110. Epub Mar. 18, 2013.

Kenis, et al. Microfabrication Inside Capillaries Using Multiphase Laminar Flow Patterning. Science. 1999; 285:83-85.

Kirkness et al. "Sequencing of isolated sperm cells for direct haplotyping of a human genome," Genome Res (2013) 23:826-832.

Kitzman et al. "Haplotype-resolved genome sequencing of a Gujarati Indian individual." Nat Biotechnol (2011) 29:59-63.

Kitzman, et al. Noninvasive whole-genome sequencing of a human fetus. Sci Transl Med. Jun. 6, 2012;4(137):137ra76. doi: 10.1126/scitranslmed.3004323.

Kivioja, et al. Counting absolute numbers of molecules using unique molecular identifiers. Nat Methods. Nov. 20, 2011;9(1):72-4.

Klein, et al. Droplet barcoding for single-cell transcriptomics applied to embryonic stem cells. Cell. May 21, 2015; 161:1187-1201.

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip The Royal Soc. of Chem. 8: 1110-1115 (2008).

Lagally, et al. Single-Molecular DNA Amplification and Analysis in an Integrated Microfluidic Device. Anal Chem. Feb. 1, 2001;73(3):565-70.

Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].

Lennon et al. A scalable, fully automated process for construction of sequence-ready barcoded libraries for 454. Genome Biology 11:R15 (2010).

Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].

Lundin, et al., "Hierarchical molecular tagging to resolve long continuous sequences by massively parallel sequencing", Sci Rep., 3:1186, 2013.

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

Madl, et al. "Bioorthogonal Strategies for Engineering Extracellular matrices", Madl, Chritopher, Adv. Funct. Master. Jan. 19, 2018, vol. 28, 1706046, pp. 1-21.

Mair, et al. Injection molded microfluidic chips featuring integrated interconnects. Lab Chip. Oct. 2006;6(10):1346-54. Epub Jul. 31, 2006.

Mccoy, R. et al. "Illumina TruSeq Synthetic Long-Reads Empower De Novo Assembly and Resolve Complex, Highly-Repetitive Transposable Elements" PLOS (2014) 9(9):e1016689.

Microfluidic ChipShop. Microfluidic product catalogue. Oct. 2009.

US 12,655,450 B1

Page 6

(56) References Cited

OTHER PUBLICATIONS

Myllykangas et al. "Efficient targeted resequencing of human germline and cancer genomes by oligonucleotide-selective sequencing," Nat Biotechnol, (2011) 29:1024-1027.

Myllykangas et al., Targeted Sequencing Library Preparation By Genomic DNA Circularization, BMC Biotechnology, 2011, 11(122), 1-12.

Navin. The first five years of single-cell cancer genomics and beyond. Genome Res. Oct. 2015;25(10):1499-507. doi: 10.1101/gr.191098.115.

Nisisako, et al. Droplet formation in a microchannel network. Lab Chip. Feb. 2002;2(1):24-6. Epub Jan. 18, 2002.

Nisisako, T. et al. Droplet Formation in a Microchannel on PMMA Plate. Micro Total Analysis Systems. 2001. Kluwer Academic Publishers. pp. 137-138.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, R. et al., "Single cell multiplex gene detection and sequencing using microfluidicallygenerated agarose emulsions" Angew. Chem. Int. Ed. Engl. (2011) 50(2):390-395.

Orakdogen, N. "Novel responsive poly(N,N-dimethylaminoethyl methacrylate) gel beads: preparation, mechanical properties and pH-dependent swelling behavior" J Polym Res (2012) 19:9914.

Perrott, Jimmy. Optimization and Improvement of Emulsion PCR for the Ion Torrent Next-Generation Sequencing Platform. (2011) Thesis.

Peters, B.A. et al. Accurate whole-genome sequencing and haplotyping from 10 to 20 human cells. Nature, 487(7406): 190-195 (Jul. 11, 2012).

Plunkett, et al. Chymotrypsin responsive hydrogel: application of a disulfide exchange protocol for the preparation of methacrylamide containing peptides. Biomacromolecules. Mar.-Apr. 2005;6(2):632-7.

Priest, et al. Generation of Monodisperse Gel Emulsions in a Microfluidic Device, Applied Physics Letters, 88:024106 (2006).

Pushkarev et al. "Single-molecule sequencing of an individual human genome," Nature Biotech (2009) 27:847-850.

Ramsey, J.M. "The burgeoning power of the shrinking laboratory" Nature Biotech (1999) 17:1061-1062.

Ramskold et al. (2012) "Full-length mRNA-Seq from single-cell levels of RNA and individual circulating tumor cells" Nature Biotechnology 30(8):777-782.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.

Rodrigue, S. et al. "Whole genome amplification and de novo assembly of single bacterial cells" PLoS One. Sep. 2, 2009;4(9):e6864. doi: 10.1371/journal.pone.0006864.

Rotem, A. et al., "High-throughput single-cell labeling (Hi-SCL) for RNA-Seq using drop-based microfluidics" PLOS One (May 22, 2015) 0116328 (14 pages).

Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.

Schubert, et al. Microemulsifying fluorinated oils with mixtures of fluorinated and hydrogenated surfactants. Colloids and Surfaces A; Physicochemical and Engineering Aspects, 84(1994) 97-106.

Seiffert, et al. Microfluidic fabrication of smart microgels from macromolecular precursors. Polymer. vol. 51, Issue 25, Nov. 26, 2010, pp. 5883-5889.

Seiffert, S. et al., "Smart microgel capsules from macromolecular precursors" J. Am. Chem. Soc. (2010) 132:6606-6609.

Shah, et al. "Fabrication of mono disperse thermosensitive microgels and gel capsules in micro fluidic devices", Soft Matter, 4:2303-2309 (2008).

Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.

Smith, et al. Highly-multiplexed barcode sequencing: an efficient method for parallel analysis of pooled samples. Nucleic Acids Research, 38(13): e142 (2010).

Song, et al. Reactions in droplets in microfluidic channels. Angew Chem Int Ed Engl. Nov. 13, 2006;45(44):7336-56.

Thaxton, C.S. et al. "A Bio-Bar-Code Assay Based Upon Dithiothreitol Oligonucleotide Release" Anal Chem (2005) 77:8174-8178.

Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.

Thorsen, et al. Dynamic pattern formation in a vesicle-generating microfluidic device. Physical Review Letters. American Physical Society. 2001; 86(18):4163-4166.

Tonelli, et al. Perfluoropolyether functional oligomers: unusual reactivity in organic chemistry. Journal of fluorine chemistry. 2002; 118(1)"107-121.

Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

Turner, et al. Assaying chromosomal inversions by single-molecule haplotyping. Nat Methods. Jun. 2006;3(6):439-45.

Turner, et al., "High-throughput haplotype determination over long distances by haplotype fusion PCR and ligation haplotyping", Nat Protoc., 4: 1771-83, 2009.

Uttamapinant, et al. Fast, cell-compatible click chemistry with copper-chelating azides for biomolecular labeling. Angew. Chem. Int. End. Engl., Jun. 11, 2012: 51(24) pp. 5852-5856.

Vitak, et al. Sequencing thousands of single-cell genomes with combinatorial indexing.Nature methods 14.3 (2017): 302-308.

Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.

Wang, et al. Efficient and unique cobarcoding of second-generation sequencing reads from long DNA molecules enabling cost-effective and accurate sequencing, haplotyping, and de novo assembly. Genome Research 29.5 (2019): 798-808.

Weigl, et al. Microfluidic Diffusion-Based Separation and Detection. Science. 1999; pp. 346-347.

Williams, et al. Amplification of complex gene libraries by emulsion PCR. Nature Methods. 2006;3(7):545-50.

Xi, et al. New library construction method for single-cell genomes. PLoS One. Jul. 19, 2017;12(7):e0181163. doi: 10.1371/journal.pone.0181163. eCollection 2017.

Xiao, et al, "Determination of haplotypes from single DNA molecules: a method for single-molecule barcoding", Hum Mutat., 28:913-21, 2007.

Zhang, et al. One-step fabrication of supramolecular microcapsules from microfluidic droplets. Science. Feb. 10, 2012;335(6069):690-4. doi: 10.1126/science.1215416.

Zheng, et al. Massively parallel digital transcriptional profiling of single cells. Nat Commun. Jan. 16, 2017;8:14049. doi: 10.1038/ncomms14049.

Zheng, X.Y. et al. "Haplotyping germline and cancer genomes with high-throughput linked-read sequencing" Nature Biotech (Feb. 1, 2016) 34(3):303-311.

Zhu, et al. Reverse transcriptase template switching: a SMART approach for full-length cDNA library construction. Biotechniques. Apr. 2001;30(4):892-7.

Co-pending U.S. Appl. No. 17/545,862, inventor Katherine; Pfeiffer, filed on Dec. 8, 2021.

Co-pending U.S. Appl. No. 18/046,843, inventor Toh; Mckenzi, filed on Oct. 14, 2022.

Co-pending U.S. Appl. No. 18/152,650, inventor Shastry; Shankar, filed on Jan. 10, 2023.

Co-pending U.S. Appl. No. 18/392,684, inventors Fernandes; Sunjay Jude et al., filed on Dec. 21, 2023.

(56)          References Cited

OTHER PUBLICATIONS

Co-pending U.S. Appl. No. 18/743,583, inventor Nagendran; Monica, filed on Jun. 14, 2024.
Co-pending U.S. Appl. No. 18/795,976, inventors Meer; Elliott et al., filed on Aug. 6, 2024.
Co-pending U.S. Appl. No. 18/824,258, inventor Stott; Ryan Timothy, filed on Sep. 4, 2024.
Co-pending U.S. Appl. No. 18/959,351, inventor Schnalll-Levin; Michael, filed on Nov. 25, 2024.
Co-pending U.S. Appl. No. 19/093,986, inventors Bloju; Octavian Marian et al., filed on Mar. 28, 2025.
Co-pending U.S. Appl. No. 19/342,226, inventor Rahimi Lenji; Mohammad, filed on Sep. 26, 2025.
Co-pending U.S. Appl. No. 19/342,369, inventor Paul; Eugene Lund et al., filed on Sep. 26, 2025.
Co-pending U.S. Appl. No. 19/343,385, inventor Schnall-Levin; Michael, filed on Sep. 29, 2025.

\* cited by examiner

600

604

610

612

606

608

616

602

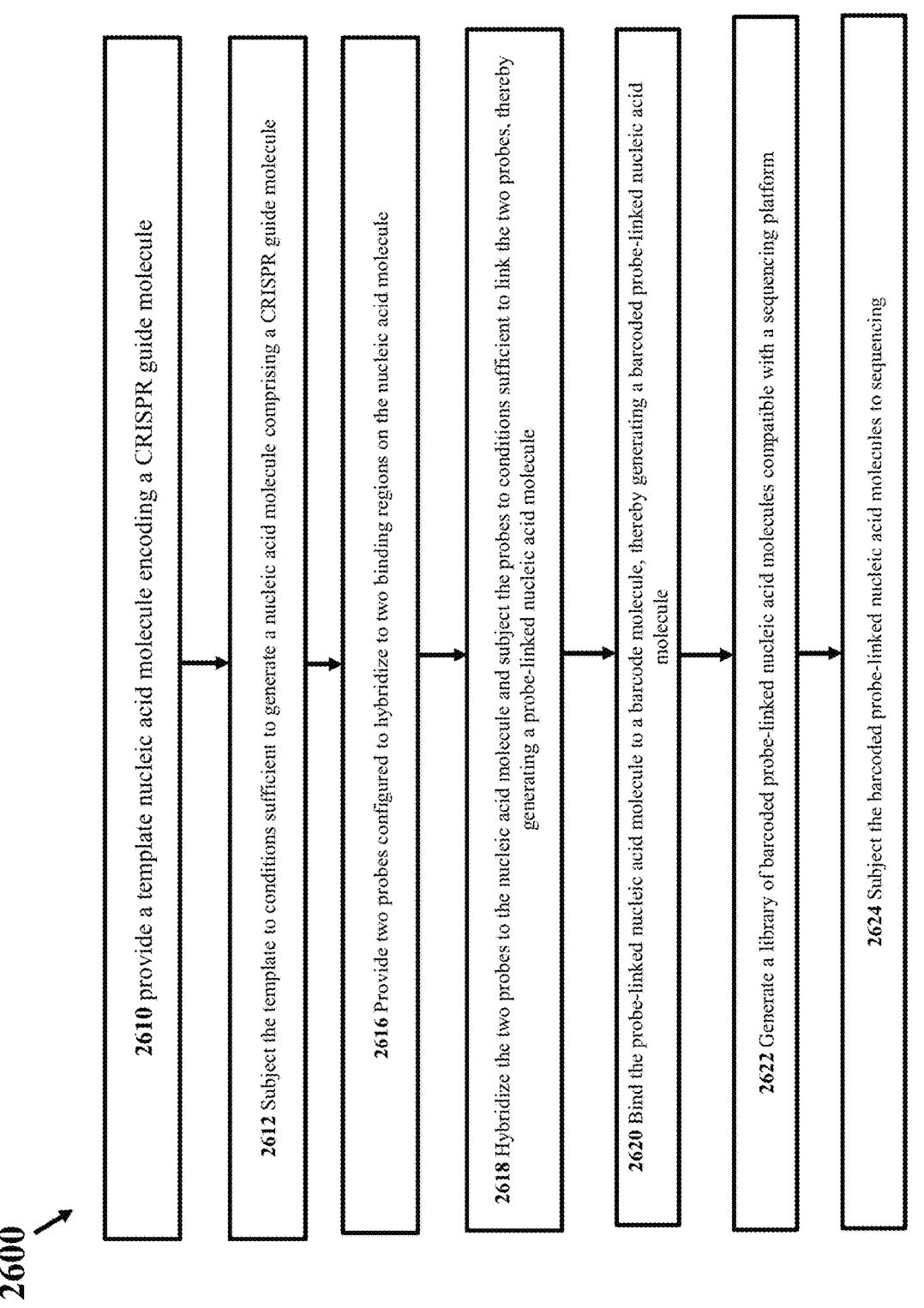

2610 provide a template nucleic acid molecule encoding a CRISPR guide molecule

2612 Subject the template to conditions sufficient to generate a nucleic acid molecule comprising a CRISPR guide molecule

2616 Provide two probes configured to hybridize to two binding regions on the nucleic acid molecule

2618 Hybridize the two probes to the nucleic acid molecule and subject the probes to conditions sufficient to link the two probes, thereby generating a probe-linked nucleic acid molecule

2620 Bind the probe-linked nucleic acid molecule to a barcode molecule, thereby generating a barcoded probe-linked nucleic acid molecule

2622 Generate a library of barcoded probe-linked nucleic acid molecules compatible with a sequencing platform

2624 Subject the barcoded probe-linked nucleic acid molecules to sequencing

METHODS, SYSTEMS, AND KITS FOR DETECTION OF NUCLEIC ACID MOLECULES

CROSS REFERENCE

This application claims the benefit of U.S. Provisional Application No. 63/106,186, filed Oct. 27, 2020, which is incorporated herein by reference in its entirety.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Biological samples may comprise nucleic acid molecules. Samples in partitions may be subjected to heating or cooling, or chemical reactions, such as to yield species that may be qualitatively or quantitatively processed.

SUMMARY

Recognized herein is a need for systems and methods for processing or analyzing samples comprising nucleic acid molecules. In some cases, samples may comprise nucleic acid molecules which may be configured to make a change such as an edit to a target nucleic acid molecule. There may be a need to detect such nucleic acid molecules configured to make a change in a target nucleic acid molecule. In some examples, the sample may comprise a CRISPR guide molecule which may be configured to make an edit to one or more nucleic acid molecules. The methods and systems provided herein may facilitate detection of CRISPR guide nucleic acid molecules. In some cases, the methods and systems may comprise providing one or more probes facilitating the detection.

The methods provided herein may comprise hybridizing one or more probes to a target nucleic acid molecule. In some examples, the target nucleic acid molecule may comprise a CRISPR guide nucleic acid molecule. In some examples, the target nucleic acid molecule may comprise a barcode sequence that permits identification of the CRISPR guide nucleic acid molecule. The CRISPR guide may comprise or be a guide RNA (gRNA) or single guide RNA (sgRNA). The gRNA may comprise a spacer sequence. Hybridizing the one or more probes to the target nucleic acid (e.g., gRNA) may generate a complex or construct such as a linked molecule which may be further processed and/or analyzed.

In some embodiments, the methods may further comprise barcoding the linked molecule or complex. The method may further comprise performing processes and/or reactions such as extension, denaturation, and/or amplification processes to provide nucleic acid molecules comprising a sequence which may be the same or substantially the same as or complementary to that of the binding region of the target nucleic acid. In some embodiments, a method may comprise hybridizing a first probe and a second probe to a target nucleic acid molecule, linking the first and second probes to provide a probe-linked nucleic acid molecule, and barcoding the probe-linked nucleic acid molecule.

In some embodiments, one or more processes of the methods provided herein may be performed within a partition such as a droplet or well. In some embodiments, the methods of the present disclosure may obviate the need for reverse transcription during analysis of ribonucleic acid molecules (RNA e.g., messenger RNA (mRNA)) and may be useful, for example, in controlled analysis and processing of analytes such as biological particles, nucleic acids, and proteins. In some examples, the methods of the present disclosure may facilitate detecting a CRISPR guide or a spacer thereof in a single-cell sequencing assay (e.g., single-cell RNA-seq assay). In some cases, the single-cell RNA-seq assay may comprise a CRISPR droplet sequencing (CROP-seq) assay.

In an aspect, the present disclosure provides a method for analysis of a plurality of nucleic acid molecules, comprising: (a) providing a plurality of nucleic acid molecules each comprising: (i) a constant upstream binding region, (ii) a variable region comprising a sequence encoding a CRISPR guide molecule or a barcode sequence that identifies the CRISPR guide molecule, and (iii) a constant downstream binding region; (b) hybridizing a plurality of first nucleic acid probes to the upstream binding regions of the plurality of nucleic acid molecules, and a plurality of second nucleic acid probes to the downstream binding regions of the plurality of nucleic acid molecules; and (c) subjecting a first nucleic acid probe of the plurality of first nucleic acid probes and/or a second nucleic acid probe of the plurality of second nucleic acid probes hybridized to a nucleic acid molecule of the plurality of nucleic acid molecules to conditions sufficient to link the first nucleic acid probe and the second nucleic acid probe to one another to yield a probe-linked nucleic acid molecule hybridized to the nucleic acid molecule.

In some embodiments, (b) comprises ligating the first nucleic acid probe to the second nucleic acid probe. In some embodiments, the ligating comprises directly ligating a 3' end of the second nucleic acid probe to a 5' end of the first nucleic acid probe. In some embodiments, (b) comprises extending a 3' end of the second nucleic acid probe to generate an extension product. In some embodiments, (b) comprises ligating a 3' end of the extension product to a 5' end of the first nucleic acid probe. In some embodiments, (b) comprises directly ligating a 5' end of the first nucleic acid probe to a 3' end of the second nucleic acid probe.

In some embodiments, the variable region comprises a spacer sequence of the CRISPR guide molecule. In some embodiments, the plurality of nucleic acid molecules is provided to a plurality of cells. In some embodiments, the first nucleic acid probe and/or the second nucleic acid probe comprises a barcode sequence.

In some embodiments, the constant upstream binding region comprises a promoter sequence. In some embodiments, the promoter sequence is a pol II promotor sequence. In some embodiments, the promoter sequence is a U6 promoter sequence.

In some embodiments, the constant downstream binding region comprises a CRISPR enzyme binding sequence. In some embodiments, the constant upstream binding region comprises the same sequence among the plurality of nucleic acid molecules. In some embodiments, the constant downstream binding region comprises the same sequence among the plurality of nucleic acid molecules.

In some embodiments, a nucleic acid molecule of the plurality of nucleic acid molecules comprises a deoxyribonucleic acid (DNA) molecule. In some embodiments, the DNA molecule is a plasmid. In some embodiments, the plasmid is a viral vector plasmid. In some embodiments, the plasmid comprises a long terminal repeat sequence. In some embodiments, the long terminal repeat sequence comprises said variable region comprising a sequence encoding a CRISPR guide RNA or the barcode sequence that identifies the CRISPR guide RNA. In some embodiments, the method comprises denaturing the plasmid prior to (b). In some embodiments, the plasmid comprises two sequences encoding the CRISPR guide molecule.

In some embodiments, a nucleic acid molecule of the plurality of nucleic acid molecules comprises a ribonucleic acid (RNA) molecule. In some embodiments, the RNA molecule is messenger RNA. In some embodiments, the RNA molecule comprises a polyA tail. In some embodiments, the RNA molecule comprises a 3' untranslated region, which comprises said variable region comprising a sequence encoding a CRISPR guide RNA or the barcode sequence that identifies the CRISPR guide RNA. In some embodiments, the method further comprises expressing the RNA molecule from a template nucleic acid molecule. In some embodiments, the template nucleic acid molecule comprises a plasmid. In some embodiments, the expressing comprises use of a RNA polymerase II. In some embodiments, the method further comprises expressing another RNA molecule from the template nucleic acid molecule. In some embodiments, the expressing the another RNA molecule comprises use of a RNA polymerase III.

In some embodiments, the method further comprises coupling a nucleic acid barcode molecule to the probe-linked nucleic acid molecule to generate a barcoded nucleic acid molecule. In some embodiments, the coupling is performed in a partition. In some embodiments, a single cell of a plurality of cells is partitioned into the partition prior to the coupling. In some embodiments, the nucleic acid barcode molecule is coupled to a solid support. In some embodiments, the partition is a droplet or a well. In some embodiments, the solid support is a bead. In some embodiments, the method further comprises extracting the probe-linked nucleic acid molecule from the partition. In some embodiments, the method further comprises breaking the partition. In some embodiments, the method further comprises sequencing the barcoded nucleic acid molecule, or an amplification product thereof. In some embodiments, the method further comprises determining a sequence of the variable region comprising a sequence encoding a CRISPR guide RNA or the barcode sequence that identifies the CRISPR guide RNA, or a sequence complementary thereto in the barcoded nucleic acid molecule, or an amplification product thereof. In some embodiments, the method further comprises subjecting the nucleic acid molecule to conditions sufficient to hybridize the first nucleic acid probe to the nucleic acid molecule to yield a nucleic acid molecule hybridized to the first nucleic acid probe. In some embodiments, the method further comprises subjecting the nucleic acid molecule hybridized to the first nucleic acid probe to conditions sufficient to hybridize the second nucleic acid probe to the nucleic acid molecule hybridized to the first nucleic acid probe.

In another aspect, the present disclosure provides a method comprising subjecting a nucleic acid molecule comprising a CRISPR spacer sequence to conditions sufficient to hybridize a first nucleic acid probe to the nucleic acid molecule and a second nucleic acid probe to the nucleic acid molecule to yield a probe-associated nucleic acid molecule.

In another aspect, the present disclosure provides a method for nucleic acid sample processing comprising a) subjecting a plasmid to conditions sufficient to express a first ribonucleic acid (RNA) molecule and a second RNA molecule; b) hybridizing a first nucleic acid probe and a second nucleic acid probe to the second RNA molecule to yield a probe-associated RNA molecule; and c) subjecting the probe-associated RNA molecule to conditions sufficient to generate a linked probe molecule, wherein the linked probe molecule comprises the first nucleic acid probe linked to the second nucleic acid probe.

In some embodiments, both the first and the second RNA molecules comprise a CRISPR guide sequence. In some embodiments, the first RNA molecule comprises a CRISPR spacer sequence configured to bind a CRISPR enzyme. In some embodiments, the plasmid comprises a long terminal repeat (LTR) sequence.

In another aspect, the present disclosure provides a system comprising a reaction volume comprising (a) a cell or nucleus comprising a plasmid configured for expression of a ribonucleic acid (RNA) molecule; (b) a first nucleic acid probe configured to hybridize to the ribonucleic acid (RNA) molecule; and (c) a second nucleic acid probe configured to hybridize to the ribonucleic acid (RNA) molecule.

In some embodiments, the RNA molecule comprises a CRISPR spacer sequence. In some embodiments, the RNA molecule comprises a sequence configured to bind a CRISPR enzyme. In some embodiments, the plasmid comprises a long terminal repeat (LTR) sequence. In some embodiments, the reaction volume is a partition. In some embodiments, the partition is a droplet or a well.

In another aspect, the present disclosure provides a kit comprising (a) a nucleic acid molecule comprising: (i) a constant upstream binding region, (ii) a variable region comprising a sequence encoding a CRISPR guide molecule or a barcode sequence that identifies the CRISPR guide molecule, and (iii) a constant downstream binding region, (b) a first nucleic acid probe configured to hybridize to the constant upstream binding region of the nucleic acid molecule; (c) a second nucleic acid probe configured to hybridize to the constant downstream binding region of the nucleic acid molecule; and (d) a support comprising a plurality of nucleic acid barcode molecules.

In some embodiments, the nucleic acid molecule comprises a deoxyribonucleic acid (DNA) molecule. In some embodiments, the DNA molecule comprises a plasmid. In some embodiments, the nucleic acid molecule comprises a ribonucleic acid (RNA) molecule. In some embodiments, the RNA molecule comprises a CRISPR spacer sequence.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 10A illustrates a nucleic acid molecule, a first probe, and a second probe, and FIG. 10B illustrates a nucleic acid molecule with the first and second probes hybridized thereto. FIG. 10C illustrates a probe-linked nucleic acid molecule, while FIG. 10D illustrates a barcoded probe-linked nucleic acid molecule.

FIG. 11A illustrates a probe-bound nucleic acid molecule. FIG. 11B shows the addition of a first barcode sequence segment. FIG. 11C shows the addition of a second barcode sequence segment. FIG. 11D shows addition of a third barcode sequence segment.

FIG. 12A illustrates a target nucleic acid molecule, a first probe, and a second probe, and FIG. 12B illustrates a target nucleic acid molecule with the first and second probes hybridized thereto. FIG. 12C illustrates a probe-linked nucleic acid molecule, while FIG. 12D illustrates a barcode molecule hybridized to a probe-linked nucleic acid molecule. FIG. 12E illustrates a barcoded probe-linked nucleic acid molecule.

FIGS. 13A-13C schematically illustrates a method of using such a probe. FIG. 13A illustrates a molecular inversion probe comprising first and second probe ends hybridized to a target nucleic acid molecule. FIG. 13B illustrates a circular probe-linked nucleic acid molecule. FIG. 13C illustrates cleavage and linearization of the circular probe for barcoding. FIGS. 13D-13E illustrate circularization of a first probe and a second probe using a splint molecule.

FIG. 15A illustrates formation of a triazole bond. FIG. 15B illustrates formation of a phosphorothioate bond. FIG. 15C illustrates formation of an amide bond. FIG. 15D illustrates a formation of phosphoramidate bond. FIG. 15E illustrates a conjugation reaction.

FIG. 16A illustrates a nucleic acid molecule, a first probe, and a second probe, while FIG. 16B illustrates a nucleic acid molecule with the first and second probes hybridized thereto and extension of the gap between probes. FIG. 16C illustrates an extended nucleic acid molecule, and FIG. 16D illustrates a probe-linked nucleic acid molecule.

FIG. 17A shows a nucleic acid molecule and a first probe. FIG. 17B illustrates a nucleic acid molecule with the first probe hybridized thereto and a hybridization of an adaptor nucleic acid molecule to a sequence of the probe. FIG. 17C illustrates hybridization of a barcode nucleic acid molecules to the adaptor nucleic acid molecule to generate a barcoded nucleic acid molecule.

FIG. 20A schematically shows barcoding of a nucleic acid molecule. FIG. 20A illustrates a probe-linked nucleic acid molecule, while FIG. 20B illustrates a splint molecule associated with a probe-linked nucleic acid molecule. FIG. 20C illustrates a nucleic acid barcode molecule associating with the adapter molecule associated with a probe-linked nucleic acid molecule while FIG. 20D illustrates a barcoded probe-linked nucleic acid molecule.

FIG. 21A illustrates a nucleic acid molecule, a first probe, a second probe, and FIG. 21B illustrates a nucleic acid molecule with the first and second probes hybridized thereto. FIG. 21C illustrates a barcoded nucleic acid molecule, while FIG. 21D illustrates digestion of unhybridized nucleic acid molecules. FIG. 21E illustrates a barcoded probe-linked nucleic acid molecule.

FIG. 22A illustrates fixation of cells and partitioning of cells. FIG. 22B shows barcoding of cells in partitions. FIG. 22C shows pooling of barcoded cells. FIG. 22D shows barcoding of barcoded cells using an adapter molecule and a barcode molecule.

FIG. 25B illustrates the analyte nucleic acid molecule presented in FIG. 25A, a first probe, and a second probe. FIG. 25C illustrates the nucleic acid molecule with the first and second probes hybridized thereto and extension of the gap between probes. FIG. 25D illustrates the extended nucleic acid molecule, and FIG. 25E illustrates a probe-linked nucleic acid molecule.

FIG. 26 shows an example workflow for performing the methods of the present disclosure.

DETAILED DESCRIPTION

Figure 1:
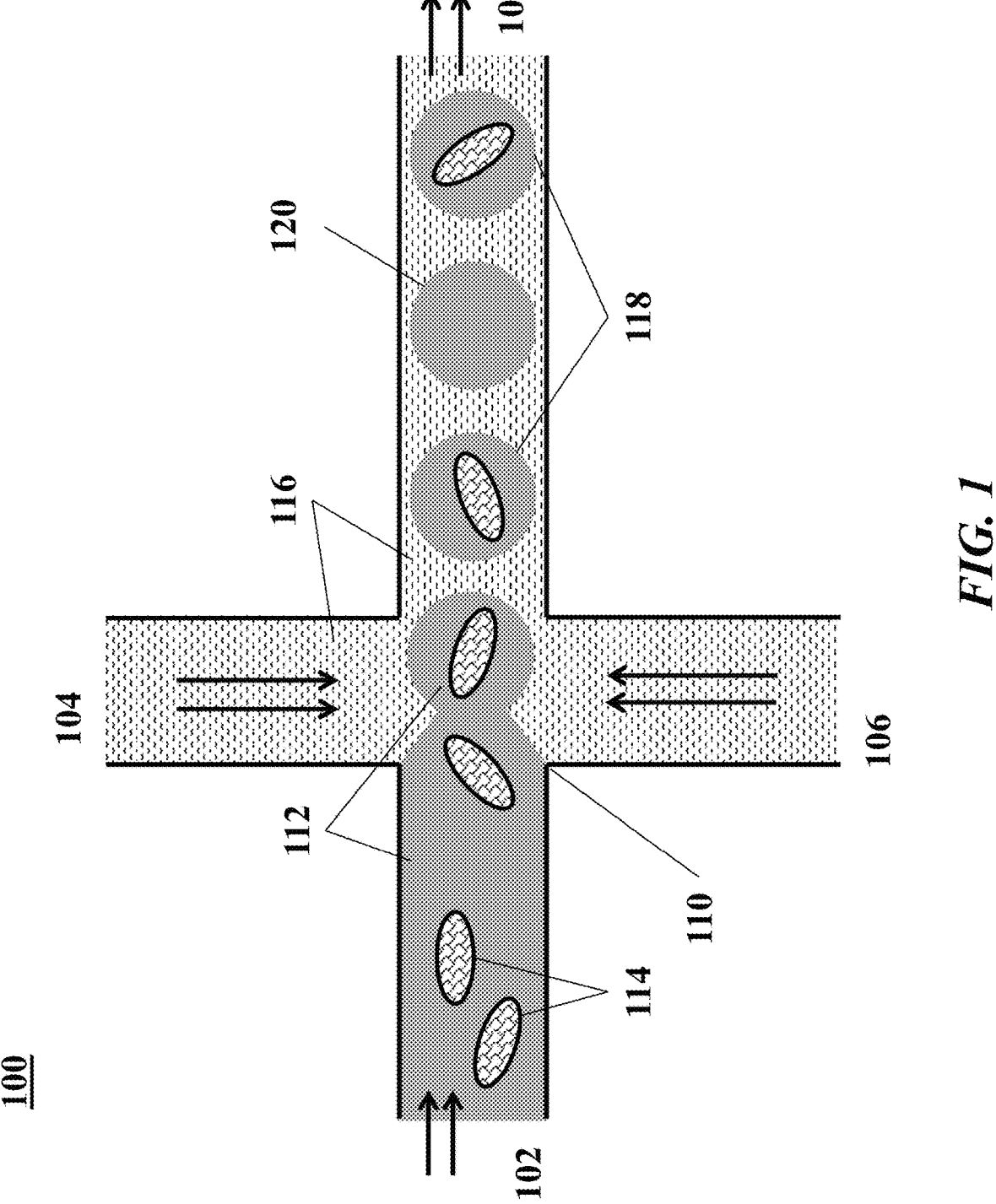
FIG. 1 shows an example of a microfluidic channel structure for partitioning individual biological particles

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values.

For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid. The nucleic acid sequence may be a targeted sequence or a non-targeted sequence. The nucleic acid barcode molecule may be coupled to or attached to the nucleic acid molecule comprising the nucleic acid sequence. For example, in the methods and systems described herein, hybridization and extension of a nucleic acid molecule (e.g., a messenger RNA (mRNA) molecule or probe molecule) of a cell with a nucleic acid barcode molecule (e.g., a nucleic acid barcode molecule containing a barcode sequence and a nucleic acid primer sequence complementary to a nucleic acid sequence of the mRNA molecule or probe molecule) results in a barcoded nucleic acid molecule that has a sequence corresponding to the nucleic acid sequence of the nucleic acid molecule and the barcode sequence (or a reverse complement thereof). The processing of the nucleic acid molecule comprising the nucleic acid sequence, the nucleic acid barcode molecule, or both, can include a nucleic acid reaction, such as, in non-limiting examples, reverse transcription, nucleic acid extension, ligation, etc. The nucleic acid reaction may be performed prior to, during, or following barcoding of the nucleic acid sequence to generate the barcoded nucleic acid molecule. For example, the nucleic acid molecule comprising the nucleic acid sequence may be subjected to reverse transcription and then be attached to the nucleic acid barcode molecule to generate the barcoded nucleic acid molecule, or the nucleic acid molecule comprising the nucleic acid sequence may be attached to the nucleic acid barcode molecule and subjected to a nucleic acid reaction (e.g., extension, ligation) to generate the barcoded nucleic acid molecule. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the nucleic acid molecule (e.g., mRNA).

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell but may not include other constituents of the cell. An example of such constituents is a nucleus or an organelle. A cell may be a live cell. The live cell may be capable of being cultured, for example, being cultured when enclosed in a gel or polymer matrix or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Methods, Systems, And Kits for Nucleic Acid Processing

Provided herein are methods, systems, and kits for processing and analyzing nucleic acid molecules. In some examples, a nucleic acid molecule (e.g., an analyte nucleic acid molecule) which may be analyzed using the methods, systems, and kits of the present disclosure may comprise a CRISPR guide molecule. In some examples, the CRISPR guide molecule may comprise a spacer sequence and a backbone or scaffold. In some examples, the nucleic acid molecule to be analyzed (e.g., a nucleic acid molecule comprising a CRISPR guide molecule) may be introduced and/or delivered into a biological particle such as a cell or a cell constituent (e.g., a nucleus of a cell) using any of a variety of techniques. For example, in some cases, a delivery molecule may be provided and/or constructed which may be configured to deliver and/or express the nucleic acid molecule within the biological particle.

The delivery molecule or delivery vehicle may comprise any molecule or sequence which may be capable of penetrating the membrane of a cell and delivering a cargo (e.g., the analyte nucleic acid molecule) into the intracellular environment. A nucleic acid molecule for analysis may be within the biological particle (e.g., cell or cell constituent). In an example, the delivery molecule may comprise or be a vector which may be configured to express a nucleic acid molecule to be analyzed (i.e., target nucleic acid molecule) within the biological particle (e.g., cell or cell constituent). In some aspects, the delivery molecule (e.g., a vector or plasmid) itself may be analyzed (i.e., target nucleic acid molecule). For example, the plasmid may contain binding regions for the first and second nucleic acid probes provided herein. In some cases, prior to binding of the nucleic acid probes to the plasmid, an optional denaturation step may be performed to separate the two strands of the plasmid. The nucleic acid molecule delivered into or expressed within a biological particle may comprise a CRISPR guide molecule and other sequences which may be configured to be detected and analyzed according to the methods of the present disclosure, such as with the aid of one or more probes which may be configured to bind the analyte nucleic acid molecule. In some cases, the plasmid may have one or more sequences encoding for CRISPR guide molecule(s) or the plasmid may have a barcode (CRISPR barcode) that permits identification or association to a CRISPR guide molecule. In some cases, various CRISPR gene editing systems can be compatible, e.g., as described in Hill et al., On the design of CRISPR-based single cell molecular screens. Nat Methods: April 2018; 15(4): 271-274; Datlinger et al., Pooled CRISPR screening with single-cell transcriptome read-out. Nat Methods. March 2017; 14(3): 297-301, and Jaitin et al., Dissecting Immune Circuits by Linking CRISPR-Pooled Screens with Single-Cell RNA-Seq. Cell: Dec. 15, 2016; 167(7): 1883-1896, each of which is incorporated herein by reference in its entirety. In some aspects, the nucleic acid molecule for analysis can be a separate reporter transcript generated from the plasmid. In some cases, this may enable determination of which CRISPR guide molecule that is introduced to the cell without capturing or analysis of the guide molecule (gRNA) itself. In some cases, the methods provided may be used with various methods, such as for single cell RNA sequencing, e.g., as described in Dixit, et al, Perturb-Seq: Dissecting Molecular Circuits with Scalable Single-Cell RNA Profiling of Pooled Genetic Screens. Cell; Dec. 15, 2016; 167(7): 1853-1866.e17, which is incorporated herein by reference in its entirety.

In some cases, one or more probes may bind to the analyte nucleic acid molecule (e.g., an analyte which may have been expressed by a template nucleic acid molecule such as a vector or plasmid in a cell with the aid of an enzyme, the analyte comprising a CRISPR guide molecule). The method may further comprise linking two probes to generate a probe-linked molecule. The probe-linked molecule may be further attached to a barcode to generate a barcoded nucleic acid molecule and be subjected to further processing and analysis according to the methods provided herein. In an example, a barcode may attach to an overhanging sequence of a probe or to the end of the probe. Extension from an end of the probe to an end of the barcode may form an extended nucleic acid molecule comprising both a sequence complementary to the barcode sequence and a sequence complementary to a binding region of the nucleic acid molecule. In some examples the extended nucleic acid molecule may then be denatured from the barcode and the nucleic acid molecule and duplicated. Duplication may comprise generating multiple copies of the barcoded probe-linked molecule. For example, the barcoded probe-linked molecule may be amplified using polymerase chain reaction (PCR). The barcoded probe-linked molecule may be further subjected to sequencing and a sequence of the barcoded probe-linked molecule may be identified. The sequence of the barcoded probe-linked molecule may indicate the presence of a particular CRISPR guide molecule.

Sequencing may comprise detecting a sequence of a spacer of a CRISPR guide molecule in a sample or in a single biological particle. In some examples, sequencing may be used to detect a barcode sequence that permits identification of the CRISPR guide nucleic acid molecule introduced to the sample. In some examples, the methods may comprise generating a library of nucleic acid molecules or constructs configured for analysis by a sequencing platform. Sequencing of such constructs may be performed to analyze and characterize the biological particles such as cells in which the analyte nucleic acid molecule comprising a CRISPR guide has been expressed, generated, and/or processed.

In an aspect, provided herein is a system comprising a reaction volume comprising a cell or nucleus comprising a plasmid configured for expression of a ribonucleic acid (RNA) molecule; a first nucleic acid probe configured to hybridize to the ribonucleic acid (RNA) molecule; and a second nucleic acid probe configured to hybridize to the ribonucleic acid (RNA) molecule. In some examples, the RNA molecule in the system may comprise a CRISPR spacer sequence. In some examples, the RNA molecule may comprise a sequence configured to bind a CRISPR enzyme. The plasmid may comprise a long terminal repeat (LTR) sequence. In some examples, the reaction volume may be a partition. The partition may be a droplet or a well.

In an aspect, provided herein is a kit comprising a nucleic acid molecule configured for expression of a ribonucleic acid (RNA) molecule; a first nucleic acid probe configured to hybridize to the ribonucleic acid (RNA) molecule (e.g., to a constant upstream binding region); a second nucleic acid probe configured to hybridize to the ribonucleic acid (RNA) molecule (e.g., to a constant downstream binding region); and a support (e.g., a bead) comprising a plurality of nucleic acid barcode molecules. In some examples, the nucleic acid molecule provided in the kit may comprise a plasmid. In some examples, the RNA molecule may comprise a CRISPR spacer sequence.

In an aspect, provided herein is a kit comprising a plurality of nucleic acid molecules wherein each nucleic acid molecule comprises: a constant upstream region; a variable region comprising a sequence encoding a CRISPR guide molecule or a barcode sequence that identifies the CRISPR guide molecule, and a constant downstream binding region; a first nucleic acid probe configured to hybridize to the nucleic acid molecule (e.g., to the constant upstream binding region); a second nucleic acid probe configured to hybridize to the nucleic acid molecule (e.g., to the constant downstream binding region); and a support (e.g., a bead) comprising a plurality of nucleic acid barcode molecules. The nucleic acid molecule may be a DNA (e.g., vector or plasmid) or an RNA molecule (e.g., transcript). The variable region of the nucleic acid molecule can be flanked on both sides with a constant binding region among a plurality of nucleic acid molecules. The variable region can be specific to the CRISPR guide molecule, thereby allowing identification of the specific CRISPR guide molecule introduced to the sample or the cell (e.g., the sequence encoding the CRISPR guide molecule or a portion thereof, a spacer sequence of the CRISPR guide molecule or a portion thereof, a barcode sequence that identifies the CRISPR guide molecule, etc.). The constant binding regions may comprise a partial sequence of the CRISPR guide molecule, for example, a backbone or scaffold sequence.

The methods and systems provided herein may facilitate analysis of nucleic acid molecules. In some examples, analysis of nucleic acid molecules may comprise analyzing a CRISPR guide nucleic acid molecule by ligation-mediated nucleic acid analysis.

An example of a workflow 2600 for performing the methods of the present disclosure is provided in FIG. 26. The methods may comprise providing 2610 a template nucleic acid molecule encoding a clustered regularly interspaced short palindromic repeats (CRISPR) guide nucleic acid molecule (e.g., an sgRNA). In some cases, the template may be a plasmid encoding a nucleic acid molecule in a biological particle such as a cell. An example of a plasmid 2400 is shown in FIG. 24. The template (e.g., a plasmid encoding a CRISPR guide molecule (e.g., sgRNA)) may penetrate a cell and enter the intracellular (e.g., intranuclear) environment of the cell. In some examples, the cell may be optionally fixed prior to 2610. The workflow 2600 may further comprise subjecting 2612 the template or plasmid to conditions sufficient to generate a nucleic acid molecule comprising a CRISPR guide. For example, the template may be used to generate (e.g., to express) a nucleic acid molecule, in some cases, with the aid of an enzyme such as a polymerase. An example of a nucleic acid molecule that can be processed and analyzed according to the methods provided herein is nucleic acid molecule 2300 shown in FIG. 23. Another example of a nucleic acid molecule that can be processed and analyzed according to the methods provided herein is a plasmid encoding a CRISPR guide molecule. For example, the plasmid 2400 with sequence 2326 encoding a CRISPR guide molecule may be used to express nucleic acid molecule 2300 comprising a CRISPR guide molecule 2326' in a cell. In some cases, the nucleic acid molecule 2300 may be a transcript generated using template or plasmid 2400. For example, a nucleic acid molecule to be analyzed may be a transcript generated using polymerase III or polymerase II on the plasmid. In some cases, the nucleic acid molecule 2300 (i.e., analyte) may comprise the guide nucleic acid molecule 2326'. The guide nucleic acid molecule 2326' (e.g., sgRNA) may comprise a guide backbone or scaffold 2320' and a spacer 2318'. In some examples, two known nucleic acid sequences (e.g., sequence 2316' and sequence 2320') may flank the spacer 2318', and the methods may comprise detecting a sequence of the spacer. Examples of the sequence of the plasmid and polymerase II transcript are described in further detail in the following sections.

The workflow 2600 may further comprise providing one or more probes (2616). The one or more probes may be nucleic acid probes. The one or more probes may be hybridization probes. In some cases, one or more of the probes may comprise a barcode sequence. The probes may be configured to hybridize to the nucleic acid molecule which is to be analyzed. For example, a probe of the one or more probes may comprise a sequence which may be substantially complementary to a sequence on the nucleic acid molecule (e.g., sequence 2316, 2318, 2320, 2316', 2318', or 2320'), or in some examples, a sequence adjacent to the spacer or the spacer itself. The nucleic acid molecule may comprise one or more binding regions each of which may be complementary to a sequence of a probe (e.g., a constant upstream binding region and a constant downstream binding region). The one or more probes may be configured to hybridize to the binding regions of the nucleic acid molecule which is to be analyzed according to the methods and systems described in further detail elsewhere herein.

The workflow 2600 may further comprise hybridizing the one or more probes to the nucleic acid molecule (2618), thereby generating a probe-linked nucleic acid molecule. In some examples, two probes may be hybridized to the nucleic acid molecule. In some cases, the two probes may bind to two adjacent sequences on the nucleic acid molecule, for example, one probe may bind to a spacer on the nucleic acid molecule, and another probe may bind to a sequence adjacent to the spacer. In another example, the two probes may bind to two sequences adjacent to the spacer sequence which may be flanking the spacer. In some aspects, the two probes may bind to two constant sequences (among a plurality of target nucleic acid molecules) flanking a variable sequence (e.g., the spacer, guide molecules, or a sequence that permits identification of the guide molecule). In some cases, the target nucleic acid molecule comprises from 5' to 3': a constant upstream binding region, a variable region, and a constant downstream binding region. The method may further comprise subjecting the probes and/or the nucleic acid molecule to conditions sufficient to link the two probes to one another. In some examples, linking may comprise or need extending one of the probes from one end, for example, if the two probes are hybridized to two sequences on the nucleic acid molecule which are not adjacent to one another. In some cases, such extension may be referred to as a gap-fill herein. Hybridization of the one or more probes to the nucleic acid molecule and linking them to one another may generate a probe-linked nucleic acid molecule comprising the CRISPR guide molecule facilitating the analysis and detection of the guide (e.g., sgRNA).

In some aspects, the method comprises: (a) providing a plurality of nucleic acid molecules each comprising: a constant upstream binding region, a variable region comprising a sequence encoding a CRISPR guide molecule or a barcode sequence that identifies the CRISPR guide molecule, and a constant downstream binding region; (b) hybridizing a plurality of first nucleic acid probes to the upstream binding regions of the plurality of nucleic acid molecules, and a plurality of second nucleic acid probes to the downstream binding regions of the plurality of nucleic acid molecules; (c) extending the 3' end of the second nucleic acid probe to generate an extension product; and (d) ligating the 3' end of the extension product to a 5' end of the first nucleic acid probe.

The workflow 2600 may further comprise binding (2620) the probe-linked nucleic acid molecule to a barcode molecule, thereby generating a barcoded probe-linked molecule according to the methods described in further detail elsewhere herein.

In some examples, the workflow 2600 may comprise partitioning the sample in a plurality of partitions such as droplets or wells. Partitioning may be performed at any point in the workflow. In an example, steps 2610-2618 may be performed in bulk prior to partitioning the sample in the partitions. For example, after 2618, the sample may be compartmentalized in a plurality of partitions such as droplets. Barcoding 2620 may be performed in partitions (e.g., droplets). In other examples, partitioning may be performed prior to 2610 or at a different time point in the workflow. In one example, a template nucleic acid molecule encoding a CRISPR guide molecule is provided to a plurality of cells and single cells of the plurality of cells can be partitioned prior to barcoding in the partition with the single cell.

The workflow 2600 may further comprise additional processing steps 2622 to generate a library of barcoded probe-linked nucleic acid molecules which may have varying sequences. The varying sequences may comprise varying spacers. In other examples, other sequences of the nucleic acid molecule may vary within the library. The library may be compatible with one or more sequencing platforms. The sequencing platform may be any sequencing platform. The workflow 2600 may further comprise subjecting 2624 the barcoded probe-linked nucleic acid molecules to sequencing. Sequencing may provide information about a plurality of biological particles such as cells which have been subject to processing according to the methods provided herein.

In an aspect, provided herein is method for analysis of a nucleic acid molecule. The nucleic acid molecule which may be analyzed according the methods of the present disclosure may be referred to as an analyte nucleic acid molecule. The method may comprise providing a nucleic acid molecule which in some cases may comprise a CRISPR guide molecule, such as a CRISPR deoxyribonucleic acid (CRISPR DNA), CRISPR ribonucleic acid (CRISPR RNA) molecule, or nucleic acids that comprises a barcode sequence that identifies a CRISPR guide molecule. In some examples, a CRISPR guide molecule may comprise or be a DNA or RNA sequence which may be found in various sources, in some cases, in the genomes of prokaryotic organisms such as bacteria and archaea. In some cases, CRISPR guide molecules may be derived from DNA fragments of bacteriophages that had previously infected the prokaryote. In some examples, CRISPR guide molecules may be used to detect and/or destroy DNA from similar bacteriophages during subsequent infections. CRISPR guide molecules may have various sources and applications and may be used to make, direct, or facilitate a change such as an edit to the sequence of one or more target nucleic acid molecules. In many examples, there may be a need to detect, analyze, read, or determine a sequence of a CRISPR guide molecule and/or a portion thereof which may for example be used to make edits to a plurality of biological particles.

The methods and systems of the present disclosure may comprise providing a CRISPR guide molecule (e.g., DNA, RNA, oligonucleotide, or another sequence) which may be configured to make an edit to a target nucleic acid molecule, for example inside a cell, such as a eukaryotic cell (e.g., mammalian cell of any kind). The method may further comprise detecting the sequence of the CRISPR guide or a portion thereof. In some aspects, a barcode sequence that permits identification of the CRISPR guide molecule can be detected.

A CRISPR guide molecule may comprise a guide RNA, such as a gRNA, an sgRNA. A guide RNA may comprise RNA molecules which may hybridize to a sequence in a nucleic acid molecule which is to be analyzed. In some examples, a change or edit to a nucleic acid molecule may comprise the insertion or deletion of uridine residues into the target sequence. The target sequence may comprise or be any kind of nucleic acid molecule. In some cases, a target nucleic acid molecule may be a messenger RNA (mRNA).

In some examples, the process of making the change or edit may be referred to as nucleic acid editing, such as RNA editing or DNA editing.

The system may further comprise a CRISPR enzyme. The methods of the present disclosure may comprise using a CRISPR enzyme. The CRISPR enzyme may comprise a nuclease. In some examples, a nuclease may comprise a CRISPR-associated protein 9 (CRISPR Cas9) which is an enzyme that may use CRISPR sequences (e.g., CRISPR RNA or DNA) as a guide to recognize and/or cleave specific strands of nucleic acid molecules (e.g., target nucleic acid molecule) that may comprise a complementary sequence to the CRISPR sequence. A system or sample comprising a nuclease (e.g., Cas9 enzyme) and CRISPR sequences may be used to make a change such as an edit to a target nucleic acid molecule which may be within a biological particle or an organism. Alternatively, the target nucleic acid molecule may be outside a biological particle or organism. A biological particle may comprise any biological particle described elsewhere herein. In some cases, a biological particle may be a cell or a cell constituent, such as a nucleus of a cell. Editing may comprise a wide variety of applications including basic biological research, development of biotechnology products, and treatment of diseases. In some cases, the plasmid 2400 may be used as a template to make the nucleic acid molecule 2300 comprising a CRISPR guide molecule, and the CRISPR guide molecule may make a complex with a CRISPR enzyme (e.g., Cas9). The CRISPR guide molecule may bind a target nucleic acid molecule, and the CRISPR enzyme may cleave the target nucleic acid molecule and make an edit to it.

In some examples, nucleic acid editing using the CRISPR guide molecule (e.g., gRNA) may comprise prokaryotic DNA editing which may, in some cases, involve CRISPR and Cas9. In an example prokaryotic DNA-editing system, the gRNA may confer target sequence specificity to the CRISPR-Cas9 system. A gRNA may comprise non-coding short RNA sequences which may bind to the complementary target DNA sequences. Guide RNA (gRNA) may bind to the Cas9 enzyme and guide the complex (e.g., via pairing) to a specific location on the DNA, where Cas9 may perform its endonuclease activity by cutting the target DNA strand.

In some examples, in addition to expression of the nuclease (e.g., Cas9), the CRISPR-nuclease system may need a specific RNA molecule to recruit and direct the nuclease activity to the region of interest. In some examples a guide RNA may comprise a synthetic trans-activating CRISPR RNA (tracrRNA) plus a synthetic CRISPR RNA (crRNA) which may be designed to cleave the gene target site of interest. In some examples, a guide nucleic acid molecule may comprise a synthetic or expressed single guide RNA (sgRNA) which may comprise at least one of a crRNA and a tracrRNA, in some cases, it may comprise both as a single construct. The crRNA and the tracrRNA may form a complex which may act as the guide RNA (gRNA) for the Cas9 enzyme. The scaffolding ability of tracrRNA along with crRNA specificity can be combined into a single synthetic gRNA which may simplify guiding of gene alterations to a one component system which may increase the editing efficiency. In some examples, there may be a need or interest for determining a sequence of a guide nucleic acid molecule or a portion thereof in a sample. In some cases, such detection may comprise a single-cell assay, such as a single-cell RNA sequencing (RNA-seq) assay. In some examples, the methods and systems provided herein may facilitate detection of spacer of a guide nucleic acid (e.g., CRISPR guide spacer) in a single-cell RNA-seq assay. In many cases, there may be a need or interest for determining a sequence of the spacer of a guide nucleic acid molecule in a sample. Detecting a sequence of the spacer sequence of the CRISPR guide molecule on the analyte molecule may facilitate determining a sequence of a protospacer sequence of a target nucleic acid molecule (i.e., target of the CRISPR guide molecule).

A target nucleic acid molecule may be a nucleic acid molecule that is targeted to be edited by the CRISPR guide molecule (e.g., sequence 2326') and a CRISPR enzyme (e.g., Cas9 or another CRISPR enzyme). For example, nucleic acid molecule 2300 which comprises a CRISPR guide molecule 2326' may be configured to bind a target nucleic acid molecule and make an edit to the sequence of the target nucleic acid molecule. In some examples, the spacer 2318' of the CRISPR guide molecule 2326' on nucleic acid molecule 2300 may be substantially complementary to a protospacer sequence on a target nucleic acid molecule and may bind to it. The methods of the present disclosure may comprise generating a linked nucleic acid molecule (e.g., a probe-linked nucleic acid molecule) which may comprise a sequence substantially complementary to the spacer sequence 2318' which may be substantially the same as a protospacer sequence of a target nucleic acid molecule. The methods, systems and kits provided here may facilitate detecting and determining the sequence of the protospacer sequence.

A target nucleic acid molecule may comprise a protospacer adjacent motif. A protospacer adjacent motif (PAM) may comprise a nucleic acid sequence which may follow the nucleic acid sequence targeted by the nuclease (e.g., Cas9). The PAM may comprise at least 1, 2, 3, 4, 5, 6, or more base pairs. In some examples, a PAM may be a 2-6-base pair DNA sequence following the DNA sequence targeted by the nuclease. The PAM may be a component of a virus, vector, or plasmid. In some examples, the nuclease may need the PAM sequence in order to bind to or cleave the target nucleic acid molecule (e.g., DNA sequence). The PAM may be a component which may distinguish bacterial self from non-self DNA, and it may prevent the CRISPR locus from being targeted and destroyed by the CRISPR-associated nuclease (e.g., Cas9).

Provided herein are methods that may be used for various sample processing and/or analysis applications. The methods may comprise processing and/or analyzing a nucleic acid molecule (e.g., an analyte nucleic acid molecule). In some examples, the nucleic acid molecule may comprise a CRISPR guide molecule, such as a gRNA which may comprise a spacer sequence. In some examples, the methods of the present disclosure may facilitate detecting the sequence of the spacer of a CRISPR guide molecule (e.g., gRNA) in a sample or in a biological particle in a sample. In some examples, the methods may facilitate detecting a sequence of a protospacer of a target nucleic acid molecule.

The nucleic acid molecule (e.g., analyte, such as a nucleic acid molecule comprising a CRISPR guide molecule) may be within a biological particle such as a cell or cell constituent (e.g., a cell nucleus). The nucleic acid molecule may be within an organism. In some examples, the sample to be processed and/or analyzed may comprise a cell and/or a cell nucleus. The methods may facilitate detecting and/or determining the sequence of the spacer 2318' of the CRISPR guide molecule and/or the sequence of the protospacer sequence of the target nucleic acid molecule.

In some examples, the methods and systems of the present disclosure may facilitate barcoding a nucleic acid molecule. In some examples, barcoding may comprise barcoding a probe-linked nucleic acid molecule such as an analyte nucleic acid molecule comprising a CRISPR guide molecule which is hybridized to one or more probes, and in some cases, may be within a partition such as a droplet, a well, or a container. Alternatively, in some cases, the nucleic acid molecule may not be in the partition.

In some examples, the method may not require performing reverse transcription. Stated a different way, in some cases, the methods of the present disclosure may be an alternative to reverse transcription, may obviate the need for reverse transcription, and may be superior to reverse transcription-based methods, for example, in terms of accuracy, precision, throughput, and/or other measures.

In some examples, the methods and systems provided herein may comprise providing one or more probes. The probes may be nucleic acid probes which may be configured to hybridize a nucleic acid molecule such as the analyte nucleic acid molecule which in some cases may comprise a CRISPR guide molecule (e.g., sgRNA). In some examples, the analyte nucleic acid molecule may comprise a binding region which may be configured to bind a first probe. The analyte nucleic acid molecule may further comprise a binding region configured to bind a second probe. The first and second probes may be similar or different.

In some examples, the method may comprise attaching a probe to the nucleic acid molecule (e.g., analyte nucleic acid molecule). The analyte nucleic acid molecule may be a nucleic acid molecule that is to be processed and/or analyzed according to the methods of the present disclosure. The nucleic acid molecule may be any suitable nucleic acid molecule. In some examples, the nucleic acid molecule may comprise an mRNA. In some examples, the nucleic acid molecule may comprise a CRISPR guide molecule. The CRISPR guide molecule may comprise a spacer sequence. The spacer sequence of the CRISPR guide molecule may be complementary to a protospacer sequence of a target nucleic acid molecule which may be configured to edited using the CRISPR-based approach. In some examples, the method provided herein may facilitate determining a sequence of the spacer sequence in an analyte nucleic acid molecule. Detecting the sequencer of the spacer (e.g., spacer 2318') and/or a sequence of a protospacer (e.g., a sequence complementary to the spacer 2318' such as sequence 2318" shown in FIG. 25D) in the target nucleic acid molecule (e.g., a target nucleic acid molecule such as a target mRNA in a cell).

The method may comprise attaching a barcode comprising a barcode sequence to the probe (e.g., subsequent to hybridizing the probe to the nucleic acid molecule which is to be analyzed). For example, the nucleic acid barcode molecule may attach to an overhanging sequence of the probe or to the end of the probe. Extension from an end of the probe to an end of the nucleic acid barcode molecule may form an extended nucleic acid molecule comprising both a sequence complementary to the barcode sequence and a sequence complementary to a binding region of the nucleic acid molecule. The extended nucleic acid molecule may then be denatured from the nucleic acid barcode molecule and the nucleic acid molecule and duplicated. In some cases, this method may obviate the need for performing reverse transcription. In some cases, reverse transcription may not be a preferred method. For example, reverse transcription may, in some cases, be error prone. Alternatively, in some cases, the methods may be compatible with or may comprise reverse transcription. One or more processes of the methods provided herein may be carried out within a partition such as a droplet or well.

In an aspect, the present disclosure provides a method for analysis of a nucleic acid molecule (e.g., analyte nucleic acid molecule). The method may comprise providing a nucleic acid molecule which may comprise a CRISPR spacer sequence. The CRISPR spacer may be a spacer of a guide nucleic acid molecule, such as a gRNA. The spacer sequence may be substantially complementary to a protospacer of a target nucleic acid molecule which may be edited using the CRISPR guide molecule. The method may comprise detecting the sequence of the spacer sequence in an analyte nucleic acid molecule in a cell and/or the sequence of a protospacer sequence in a target nucleic acid molecule in the cell. The method may be applied in a population of cells and be used to determine the sequences of a plurality of spacers of the analyte nucleic acid molecules (e.g., a plurality of different analyte nucleic acid molecules) and/or the sequences of a plurality of protospacers (e.g., plurality of different protospacers) in a plurality of target nucleic acid molecules in a plurality of cells. The method may be used for cell profiling.

Figure 23:
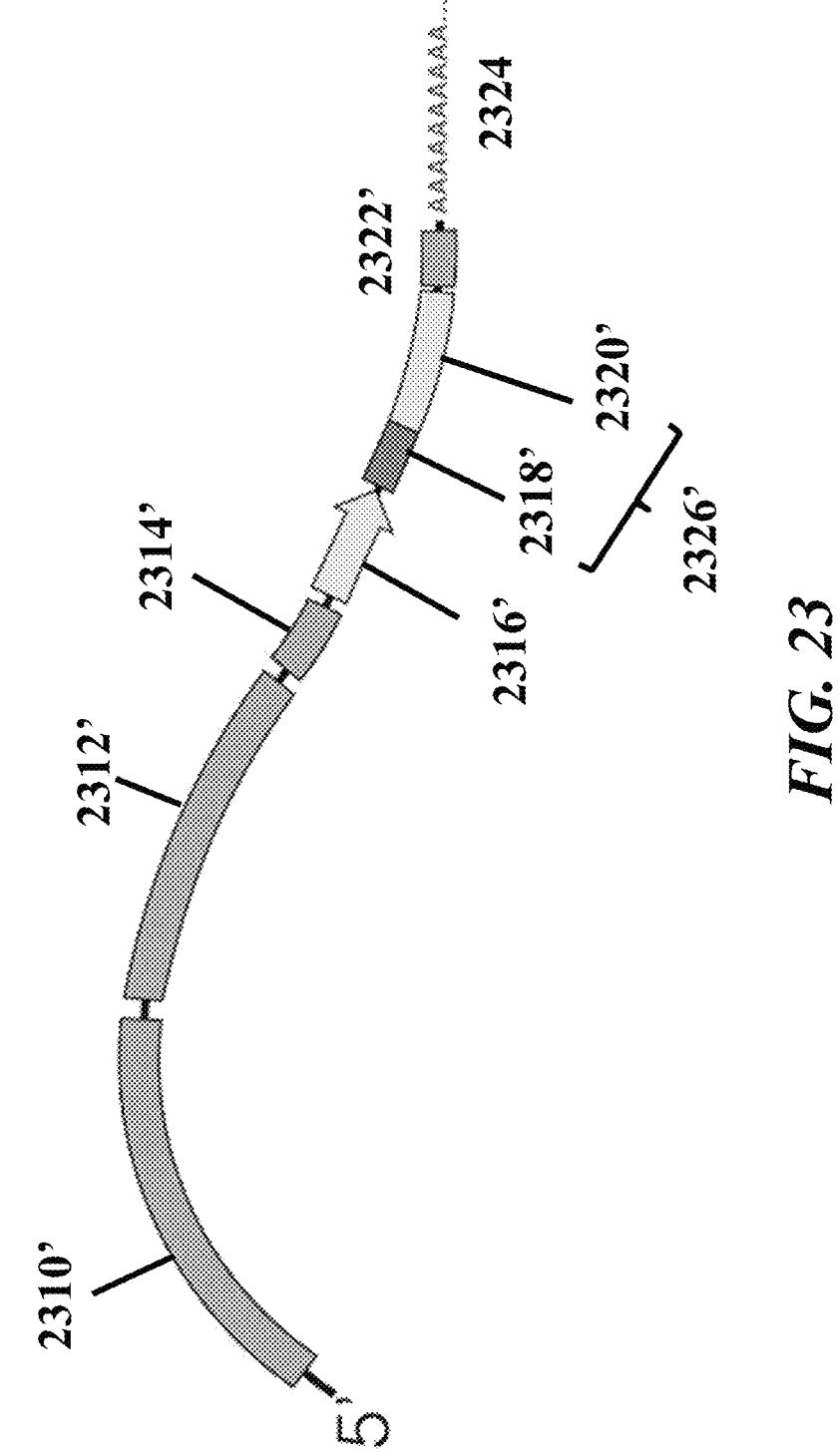
FIG. 23 shows an example nucleic acid molecule which may be processed and analyzed using the methods, systems, and kits of the present disclosure.
Figure 24:
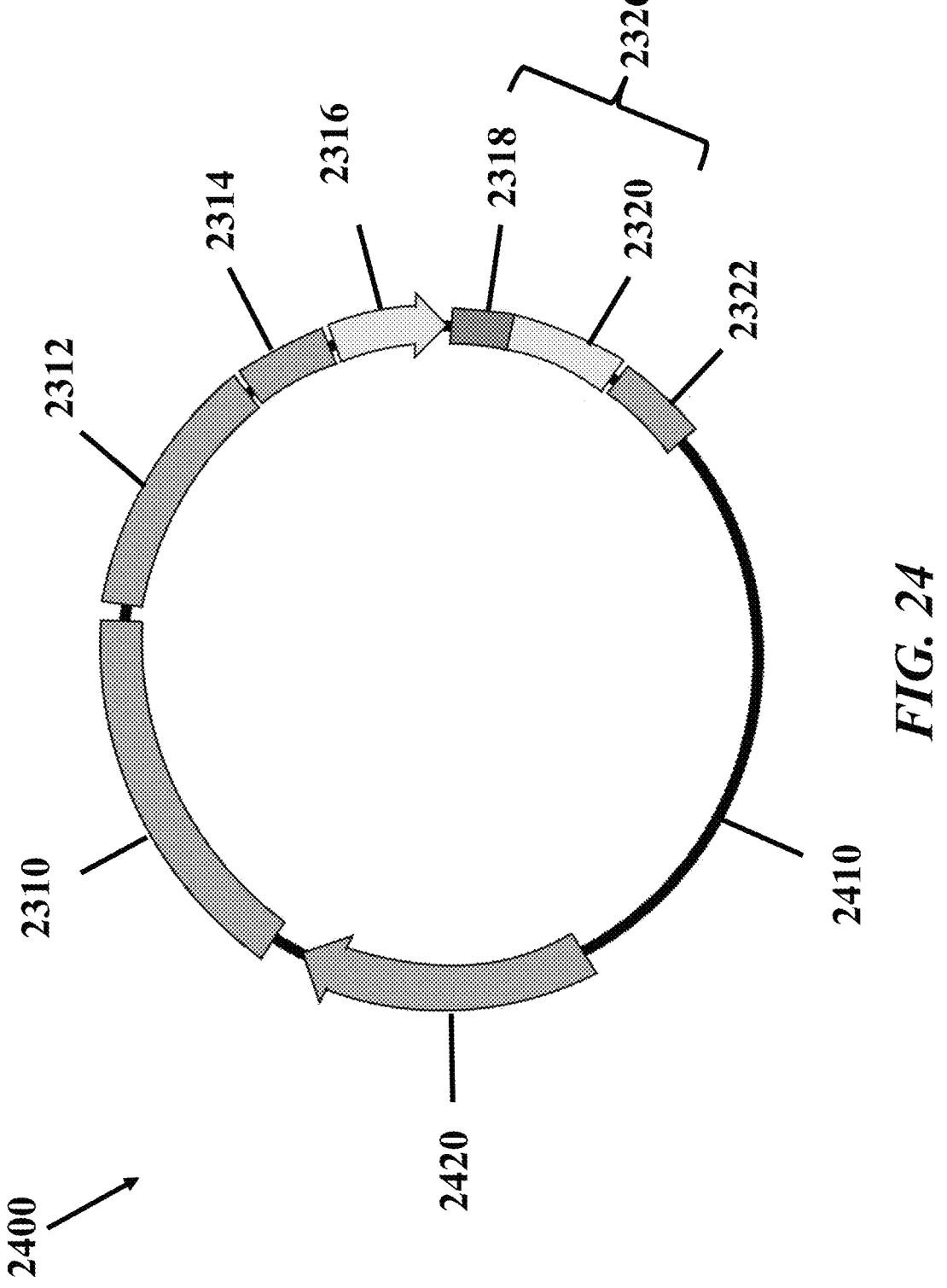
FIG. 24 shows an example plasmid encoding the nucleic acid molecule shown in FIG. 23 which may be processed according to the methods provided herein.

An example of a nucleic acid molecule (e.g., analyte) 2300 which may be processed and/or analyzed using the methods of the present disclosure is shown in FIG. 23. The methods, systems, and kits of the present disclosure may comprise the nucleic acid molecule 2300 or may facilitate providing (e.g., encoding) the nucleic acid molecule which is to be analyzed (e.g., in a cell). The nucleic acid molecule 2300 may comprise a CRISPR guide molecule 2326'. The CRISPR guide molecule 2326' may comprise a spacer 2318' and a backbone or scaffold 2320'. In some examples, the spacer may comprise or be a viral DNA, such as an ssDNA. In some examples, the method provided herein may comprise determining the sequence of the spacer 2318' with the aid of one or more probes using the methods, systems, and kits provided herein. The backbone or scaffold 2320' may be adjacent to the spacer 2318'. For example, the backbone may be on the 3' end of the spacer 2318'.

The nucleic acid molecule may further comprise a promoter sequence 2316'. In an example, the promoter sequence may comprise or be a U6 promoter, such as a human U6 promoter sequence. In some examples, the promoter sequence 2316' may be adjacent to the spacer 2318'. For example, the promoter sequence may be on the 5' end of the spacer 2318'. The nucleic acid molecule 2300 may further comprise one or more long terminal repeats (LTR). For example, the nucleic acid molecule 2300 may comprise an LTR 2322' adjacent to the CRISPR guide molecule 2326'. The LTR 2322' may be on the 3' end of the scaffold 2320' of the CRISPR guide molecule 2326'.

The nucleic acid molecule 2300 may further comprise a poly-A tail 2324. The poly-A tail may be on the 3' end of the nucleic acid molecule 2300. In some examples, the poly-A tail may be on the 3' end of the LTR 2322'. The poly-A tail may facilitate detecting the nucleic acid molecule using the methods provided herein and analyzing it by sequencing. The nucleic acid molecule 2300 may further comprise another LTR 2314'. The LTR 2314' may be on the 5' end of the promoter sequence 2316'.

The method may further comprise providing one or more probes. The methods, systems, and kits of the present disclosure may comprise or provide one or more probes. In some examples, the CRISPR spacer sequence may be hybridized to one or more probes. In an example, the CRISPR spacer sequence may be hybridized to a first nucleic acid probe and a second nucleic acid probe. The method may comprise subjecting the first nucleic acid probe or the second nucleic acid probe to conditions sufficient to link the first nucleic acid probe and the second nucleic acid probe to one another to yield a nucleic acid probe-linked molecule hybridized to the nucleic acid molecule.

In some examples, subjecting the first nucleic acid probe or the second nucleic acid probe to conditions sufficient to link the first nucleic acid probe and the second nucleic acid probe to one another may comprise ligating the first nucleic acid probe to the second nucleic acid probe. In some examples, the ligating may comprise ligating (e.g., directly) a 3' end of the second nucleic acid probe to a 5' end of the first nucleic acid probe. In some examples, subjecting the first nucleic acid probe or the second nucleic acid probe to conditions sufficient to link the first nucleic acid probe and the second nucleic acid probe to one another may comprise extending a 3' end of the second nucleic acid probe to generate an extension product. In some examples, subjecting the first nucleic acid probe or the second nucleic acid probe to conditions sufficient to link the first nucleic acid probe and the second nucleic acid probe to one another may comprise ligating a 3' end of the extension product to a 5' end of the first nucleic acid probe.

In some examples, providing a nucleic acid molecule comprising a CRISPR spacer sequence hybridized to a first nucleic acid probe and a second nucleic acid probe may comprise (i) hybridizing the first nucleic acid probe to a first binding region 5' of the CRISPR spacer sequence and (ii) hybridizing the second nucleic acid probe to a second binding region 3' of the CRISPR spacer sequence. In some examples, the first binding region comprises a promoter sequence. In some examples, the promoter sequence may be a human U6 promoter sequence. In some examples, the second binding region may comprise a CRISPR enzyme binding sequence.

In an example, a binding region is the scaffold of the CRISPR guide molecule and another binding region is the promoter sequence. In another example, a binding region is the spacer sequence of the CRISPR guide nucleic acid molecule and another binding region is the promoter sequence.

In some examples, subjecting the first nucleic acid probe or the second nucleic acid probe to conditions sufficient to link the first nucleic acid probe and the second nucleic acid probe to one another may comprise extending a 3' end of the second nucleic acid probe to generate an extension product. In some examples, subjecting the first nucleic acid probe or the second nucleic acid probe to conditions sufficient to link the first nucleic acid probe and the second nucleic acid probe to one another may comprise ligating a 3' end of the extension product to a 5' end of the first nucleic acid probe.

In some examples, providing a nucleic acid molecule comprising a CRISPR spacer sequence hybridized to a first nucleic acid probe and a second nucleic acid probe may comprise hybridizing the first nucleic acid probe to a binding region 5' of the CRISPR spacer sequence and hybridizing the second nucleic acid probe to the CRISPR spacer sequence. In some examples, the binding region may comprise a promoter sequence. In some examples, the promoter sequence may be a U6 promoter sequence, such as a human U6 promoter sequence.

In some examples, subjecting the first nucleic acid probe or the second nucleic acid probe to conditions sufficient to link the first nucleic acid probe and the second nucleic acid probe to one another may comprise directly ligating a 5' end of the first nucleic acid probe to a 3' end of the second nucleic acid probe.

In some examples providing a nucleic acid molecule comprising a CRISPR spacer sequence hybridized to a first nucleic acid probe and a second nucleic acid probe may comprise hybridizing the first nucleic acid probe to the CRISPR spacer sequence and hybridizing the second nucleic acid probe to a binding region 3' of the CRISPR spacer sequence.

In some examples, the binding region 3' of the CRISPR spacer sequence comprises a CRISPR enzyme binding sequence (e.g., backbone or scaffold of a CRISPR guide molecule). In some examples, the method may comprise directly ligating a 5' end of the first nucleic acid probe to a 3' end of the second nucleic acid probe.

In some examples, the nucleic acid molecule (e.g., analyte nucleic acid molecule) may comprise a ribonucleic acid (RNA) molecule. In some examples, the RNA molecule may be a messenger RNA. In some examples, the RNA molecule (e.g., mRNA) may comprise a poly-A tail. The poly-A tail may facilitate analyzing the molecule (e.g., according to the methods provided herein and/or by sequencing).

In some examples, the method may further comprise expressing the analyte nucleic acid molecule from a template nucleic acid molecule. In some cases, the template nucleic acid molecule may comprise or be a plasmid. In some cases, expressing may comprise use of an enzyme such as a polymerase (e.g., RNA polymerase II). In some examples, the method may further comprise expressing another RNA molecule from the template nucleic acid molecule. Expressing the another RNA molecule may comprise use of an RNA polymerase III.

In some examples, the method may further comprise coupling a barcode to the probe-linked nucleic acid molecule to generate a barcoded nucleic acid molecule (e.g., barcoded probe-linked nucleic acid molecule). In some examples, the coupling may be performed in a partition. In some examples, the barcode may be coupled to a support. The support may be solid or semi-solid. The support may be a bead. The support may be a gel bead. In some examples, the partition may be a droplet or a well (e.g., a microwell).

In some examples, the method may further comprise extracting the probe-linked nucleic acid molecule from the partition. In some examples, the method may further comprise breaking the partition. Breaking the partition (e.g., breaking or coalescing droplets) may be accomplished using a wide variety of techniques. Breaking may facilitate extracting the contents of the partitions such as the linked nucleic In some examples, the method may further comprise sequencing the barcoded nucleic acid molecule, or an amplification product thereof. The method may further comprise determining a sequence of the CRISPR spacer or a sequence complementary thereto (e.g., a sequence of a protospacer of a target nucleic acid molecule) in the barcoded nucleic acid molecule or an amplification product thereof. The method may further comprise subjecting the nucleic acid molecule to conditions sufficient to hybridize the first nucleic acid probe to the nucleic acid molecule to yield a nucleic acid molecule hybridized to the first nucleic acid probe.

The method may further comprise subjecting the nucleic acid molecule hybridized to the first nucleic acid probe to conditions sufficient to hybridize the second nucleic acid probe to the nucleic acid molecule hybridized to the first nucleic acid probe to generate the nucleic acid molecule comprising a CRISPR spacer sequence hybridized to a first nucleic acid probe and a second nucleic acid probe.

In an aspect, provided herein is a method comprising subjecting a nucleic acid molecule comprising a CRISPR spacer sequence to conditions sufficient to hybridize a first nucleic acid probe to the nucleic acid molecule and a second nucleic acid probe to the nucleic acid molecule to yield a probe-associated nucleic acid molecule.

Provided herein is a method for nucleic acid sample processing, comprising: subjecting a plasmid to conditions sufficient to express a ribonucleic acid (RNA) molecule; hybridizing a first nucleic acid probe and a second nucleic acid probe to the RNA molecule to yield a probe-associated RNA molecule; and subjecting the probe-associated RNA molecule to conditions sufficient to generate a linked probe molecule. The linked probe molecule may comprise the first nucleic acid probe linked to the second nucleic acid probe. The linked nucleic acid probe molecule may be hybridized to the nucleic acid molecule. The linked nucleic acid probe molecule hybridized to the nucleic acid molecule may be herein referred to as the probe-linked nucleic acid molecule.

In some examples, the RNA molecule may comprise a CRISPR spacer sequence. The RNA molecule may comprise a sequence configured to bind a CRISPR enzyme, such as a scaffold or backbone. The plasmid may comprise a long terminal repeat (LTR) sequence. The plasmid may comprise or be a vector.

The method provided herein may comprise processing a sample that may provide a barcoded nucleic acid molecule having linked probe molecules attached thereto. The method may comprise one or more ligation-mediated reactions. The method may comprise providing a sample comprising a nucleic acid molecule (e.g., a nucleic acid molecule comprising a CRISPR guide such as a guide RNA (sgRNA)) having first and second binding regions; a first probe having a first probe sequence that is complementary to the first binding region and a second probe sequence; and a second probe having a third probe sequence that is complementary to the second binding region. The first and third probe sequences may also comprise first and second reactive moieties, respectively. Upon hybridization of the first probe sequence of the first probe to the first binding region of the nucleic acid molecule, and hybridization of the third probe sequence of the second probe to the second binding region of the nucleic acid molecule, the reactive moieties may be adjacent to one another. Subsequent reaction between the adjacent reactive moieties under sufficient conditions may link the first and second probes to yield a probe-linked nucleic acid molecule. The probe-linked nucleic acid molecule may also be referred to as a probe-ligated nucleic acid molecule. The probe-linked nucleic acid molecule may then be barcoded with a barcode to provide a barcoded probe-linked nucleic acid molecule.

Barcoding may be achieved by hybridizing a binding sequence of the barcode to the second probe sequence of the first probe of the probe-linked nucleic acid molecule. The barcoded probe linked-nucleic acid molecule may be subjected to amplification reactions to yield an amplified product comprising the first and second binding regions and the barcode sequence or sequences complementary to these sequences. Accordingly, the method may provide amplified products without the use of reverse transcription. One or more processes may be performed within a partition such as a droplet or well.

Further provided herein are methods of processing a sample that provides a barcoded nucleic acid molecule having linked probe molecules attached thereto. The method may comprise one or more nucleic acid reactions. The method may comprise providing a sample comprising a nucleic acid molecule (e.g., an analyte nucleic acid molecule which may comprise a CRISPR guide molecule (e.g., nucleic acid molecule 2300)) having first and second binding regions on a same strand (e.g., adjacent or non-adjacent binding regions); a first probe having a first probe sequence that is complementary to the first binding region and a second probe sequence; and a second probe having a third probe sequence that is complementary to the second binding region. The third probe sequence may be known or degenerate (e.g., randomly generated).

An example analyte nucleic acid molecule may be nucleic acid molecule 2300 shown in FIG. 23. In some examples, nucleic acid 2300 may be a CRISPR guide molecule in a polyadenylated mRNA transcript. The nucleic acid molecule 2300 may comprise a CRISPR guide nucleic acid molecule (e.g., gRNA) spacer and two sequences (e.g., binding regions) flanking the spacer. Alternatively or in addition, the spacer may be a binding region. The first and third probe sequences may also comprise first and second reactive moieties, respectively. Where the nucleic acid molecule may have non-adjacent first and second binding regions, the nucleic acid molecule may comprise one or more gap regions between the first and second binding regions. Upon hybridization of the first probe sequence of the first probe to the first binding region of the nucleic acid molecule, and the third probe sequence of the second probe to the second binding region of the nucleic acid molecule, to yield a probe-associated nucleic acid molecule, the reactive moieties may be adjacent or non-adjacent to one another. Subsequent reaction between the adjacent or non-adjacent probes may generate a probe-linked nucleic acid molecule. The probe-linked nucleic acid molecule may also be referred to herein as a probe-ligated nucleic acid molecule. The probe-linked nucleic acid molecule may then be barcoded with a barcode to provide a barcoded probe-linked nucleic acid molecule. Barcoding may be achieved by hybridizing a binding sequence of the barcode to the second probe sequence of the first probe of the probe-linked nucleic acid molecule. Barcoding may also be achieved by hybridizing a binding sequence of a barcode to a nucleic acid adaptor sequence, where the nucleic acid adaptor sequence comprises a binding sequence that can hybridize to one or more nucleic acid probes. The barcoded probe linked-nucleic acid molecule may be subjected to amplification reactions to yield an amplified product comprising the first and second binding regions and the barcode sequence or sequences complementary to these sequences. Accordingly, the method may provide amplified products without the use of reverse transcription. One or more processes may be performed within a cell bead and/or a partition, such as a droplet or well. In some examples the method provided herein may comprise ligation-mediated analysis of nucleic acids. Examples of ligation-mediated analysis methods may be similar to methods described in WO Publication No. 2019/165318, which is incorporated by reference herein in its entirety for all purposes.

In an aspect, the present disclosure provides methods, systems, and kits comprising providing a sample comprising a nucleic acid molecule (i.e., analyte). In some examples the analyte nucleic acid molecule may be nucleic acid molecule 2300 shown in FIG. 23. The nucleic acid molecule (i.e., analyte) may comprise a binding region and a probe may comprise (i) a first probe sequence complementary to the sequence of the binding region of the nucleic acid molecule and (ii) a second probe sequence; attaching (e.g., hybridizing) the first probe sequence of the probe to the binding region of the nucleic acid molecule. The method may comprise providing a barcode comprising (i) a first binding sequence that is complementary to the second probe sequence, (ii) a barcode sequence, and (iii) a second binding sequence; attaching (e.g., hybridizing) the first binding sequence of the barcode to the second probe sequence of the probe; extending the probe from an end of the second probe sequence to an end of the second binding sequence of the barcode to form an extended nucleic acid molecule comprising both a sequence complementary to the barcode sequence and a sequence complementary to the binding region of the nucleic acid molecule. The method may comprise denaturing the extended nucleic acid molecule from the barcode and the binding region of the nucleic acid molecule to regenerate the barcode and the nucleic acid molecule. The method may further comprise duplicating the extended nucleic acid molecule. The extended nucleic acid molecule may be further amplified (e.g., using polymerase chain reactions (PCR) or linear amplification, as described herein) to facilitate the detection of the extended nucleic acid molecule or a complement thereof (e.g., an amplified product), for example by sequencing.

In some examples, the methods, systems, and kits described herein may facilitate gene expression profiling with single cell resolution using, for example, chemical ligation-mediated barcoding, amplification, and sequencing. The methods described herein may allow for gene expression analysis while avoiding the use of specialized imaging equipment and reverse transcription, which may be highly error prone and inefficient. For example, the methods may be used to analyze a pre-determined panel of target genes in a population of single cells in a sensitive and accurate manner. In some cases, the nucleic acid molecule analyzed by the methods described herein may be a fusion gene (e.g., a hybrid gene generated via translocation, interstitial deletion, or chromosomal inversion). In some examples, the nucleic acid molecule analyzed by the methods described herein may comprise or be a CRISPR guide molecule (e.g., sgRNA). The CRISPR guide molecule (e.g., nucleic acid molecule 2300 shown in FIG. 23) may be a transcript of a plasmid described herein. In some cases, the nucleic acid molecule to be analyzed may be a polymerase II transcript of a plasmid (e.g., plasmid 2400 shown in FIG. 24). As described in further detail elsewhere herein, the plasmid may encode the sequence of the CRISPR guide molecule. In some examples, the plasmid may be used to express the nucleic acid molecule in 2300 in a cell. The nucleic acid molecule (e.g., the CRISPR guide molecule) may comprise a spacer sequence which may be substantially complementary to a protospacer sequence with a target nucleic acid molecule in the cell. The method may comprise detecting the sequence of the spacer of the CRISPR guide molecule which may facilitate determining the sequence of the protospacer sequence of the target nucleic acid molecule in a cell or in a plurality of cells.

The methods of the present disclosure may facilitate analyzing the expression of CRISPR guide molecules and/or transcriptome responses in a cell or a plurality of cells, in some cases, in a large number of cells, such as thousands of individual cells. In some cases, the methods may facilitate analyzing the correlations and/or relationships between the expression of the CRISPR guide molecule and transcriptome responses in a cell of a plurality of cells. The methods and systems provided herein provide pooled CRISPR screens with single-cell transcriptome resolution and may have various applications. The methods, systems, and kits provided herein may facilitate high-throughput functional dissection of regulatory mechanisms and heterogeneous cell populations.

The methods, systems, and kits provided herein may facilitate generating a nucleic acid molecule comprising a CRISPR guide molecule (e.g., sgRNA) which may be transcribed from a plasmid by an enzyme such as an RNA polymerase II inside a cell. The cell or medium may further comprise a CRISPR enzyme (e.g., Cas9). In some cases, the CRISPR enzyme may form a complex with the CRISPR guide molecule. The CRISPR enzyme and CRISPR guide molecule may facilitate making a change to a target nucleic acid molecule. In some cases, the methods, systems, and kits may facilitate generating a library of different CRISPR guide nucleic acid molecules (e.g., guide RNAs) and directing one or more mutations, changes, or edits to one or more nucleic acid molecules in a cell.

The methods may comprise analyzing the nucleic acid molecule (i.e., analyte) comprising the CRISPR guide molecule (e.g., a nucleic acid molecule similar to molecule 2300 shown in FIG. 23) and detecting the sequence of the spacer of the CRISPR guide molecule and/or a sequence of a protospacer of a target thereof which may be complementary to the spacer sequence in a sample or a single cell in a sample. For example, the methods may comprise or be used in single cell RNA sequencing assays. In some cases, the spacer of the CRISPR guide (which can be used to identify the sequence of the protospacer of the target nucleic acid molecule for editing using the CRISPR guide molecule) is located in the 3' untranslated region (UTR) of the Pol-II transcript (e.g., 2300).

The methods, systems, and kits provided herein may provide a plasmid, such as the plasmid 2400 shown in FIG. 24 which may facilitate generating (e.g., encoding) nucleic acid molecule 2300 in a cell which can then be detected by a ligation-mediated analysis methods using one or more probes (e.g., two probes) configured to bind two binding regions on the nucleic acid molecule 2300, in some examples, two sequences flanking the spacer of the CRISPR guide molecule.

Plasmid 2400 shown in FIG. 24 may comprise a plasmid backbone 2410, a sequence 2322 encoding a long terminal repeat 2322' in the nucleic acid molecule 2300, a sequence 2326 encoding a CRISPR guide molecule 2326' in nucleic acid molecule 2300. The sequence 2326 may comprise a sequence 2320 encoding a scaffold 2320' in the nucleic acid molecule 2300. The sequence 2326 may further comprise a sequence 2318 encoding a spacer 2318' of the CRISPR guide molecule 2326' in the nucleic acid molecule 2300. The plasmid 2400 may further comprise a sequence 2316 encoding a promoter sequence (e.g., human U6, e.g., promoter 2316' of the nucleic acid molecule 2300). The plasmid may further comprise a sequence 2314 encoding a long terminal repeat (LTR 2314') in the nucleic acid molecule 2300. The plasmid 2400 may further comprise additional sequences such as sequence 2312 and sequence 2310 configured to encode sequences 2312' and sequence 2310' on the nucleic acid molecule 2300. Plasmid 2400 may further comprise promoter 2420 which may be a polymerase II promoter. In some cases, a separate reporter transcript can be encoded by plasmid 2400 such as a barcode that is expressed as part of the Polymerase II transcript 2300 and can be sequenced as a proxy for the guide sequence. In some aspects, the plasmid may include two copies of the guide sequence. For example, one copy of the guide sequence (or portion thereof) can be cloned into the 3' long terminal repeat (LTR) of the vector 2400. The guide sequence itself may be transcribed as part of the Polymerase II transcript and can therefore be sequenced directly, and a second copy of the guide expression cassette can be included in the 5' LTR during lentivirus positive strand synthesis prior to integration.

FIG. 25 shows and example of a plasmid 2400 provided herein. In some cases, an enzyme such as an RNA polymerase II may transcribe the plasmid 2400, thereby generating the nucleic acid molecule 2300. Alternatively or in addition, an RNA polymerase III enzyme may transcribe the plasmid 2400, thereby generating nucleic acid molecule 2500. Nucleic acid molecule 2300 and nucleic acid molecule 2500 may comprise a spacer sequence 2318 and a scaffold and/or backbone 2320. The scaffold or backbone may be configured to bind a CRISPR enzyme. In some examples, the systems and kits of the present disclosure may further comprise providing a CRISPR enzyme. The structure of nucleic acid molecule 2500 and the scaffold 2320 are schematically illustrated in structure 2520 shown in FIG. 25.

The nucleic acid molecule (i.e., analyte) provided herein and analyzed by the methods described herein may be a single-stranded or a double-stranded nucleic acid molecule. A double-stranded nucleic acid molecule may be completely or partially denatured to provide access to a binding region of a strand of the nucleic acid molecule. Denaturation may be achieved by, for example, adjusting the temperature or pH of a solution comprising the nucleic acid molecule; using a chemical agent such as formamide, guanidine, sodium salicylate, dimethyl sulfoxide, propylene glycol, urea, or an alkaline agent (e.g., NaOH); or using mechanical agitation (e.g., centrifuging or vortexing a solution including the nucleic acid molecule).

The nucleic acid molecule may be an RNA molecule. The RNA molecule may be, for example, a transfer RNA (tRNA) molecule, ribosomal RNA (rRNA) molecule, mitochondrial RNA (mtRNA) molecule, messenger RNA (mRNA) molecule, non-coding RNA molecule, synthetic RNA molecule, or another type of RNA molecule. For example, the RNA molecule may be an mRNA molecule. In some cases, the nucleic acid molecule may be a viral or pathogenic RNA. In some cases, the nucleic acid molecule may be a synthetic nucleic acid molecule previously introduced into or onto a cell. For example, the nucleic acid molecule may comprise a plurality of barcode sequences, and two or more barcode sequences may be binding regions of the nucleic acid molecule.

The nucleic acid molecule (e.g., RNA molecule) analyzed using the methods of the present disclosure may comprise one or more features selected from the group consisting of a 5' cap structure, an untranslated region (UTR), a 5' triphosphate moiety, a 5' hydroxyl moiety, a Kozak sequence, a Shine-Dalgarno sequence, a coding sequence, a codon, an intron, an exon, an open reading frame, a regulatory sequence, an enhancer sequence, a silencer sequence, a promoter sequence, and a poly(A) sequence (e.g., a poly(A) tail). For example, the nucleic acid molecule may comprise one or more features selected from the group consisting of a 5' cap structure, an untranslated region (UTR), a Kozak sequence, a Shine-Dalgarno sequence, a coding sequence, and a poly(A) sequence (e.g., a poly(A) tail).

Features of the nucleic acid molecule may have any useful characteristics. A 5' cap structure may comprise one or more nucleoside moieties joined by a linker such as a triphosphate (ppp) linker. A 5' cap structure may comprise naturally occurring nucleoside and/or non-naturally occurring (e.g., modified) nucleosides. For example, a 5' cap structure may comprise a guanine moiety or a modified (e.g., alkylated, reduced, or oxidized) guanine moiety such as a 7-methyl-guanylate ($m^7G$) cap. Examples of 5' cap structures include, but are not limited to, $m^7GpppG$, $m^7Gpppm^7G$, $m^7GpppA$, $m^7GpppC$, $GpppG$, $m^{2,7}GpppG$, $m^{2,2,7}GpppG$, and anti-reverse cap analogs such as $m^{7,2'Ome}GpppG$, $m^{7,2'd}GpppG$, $m^{7,3'Ome}GpppG$, and $m^{7,3'd}GpppG$. An untranslated region (UTR) may be a 5' UTR or a 3' UTR. A UTR may include any number of nucleotides. For example, a UTR may comprise at least 3, 5, 7, 10, 20, 30, 40, 50, 60, 70, 80, 90, 100, or more nucleotides. In some cases, a UTR may comprise fewer than 20 nucleotides. In other cases, a UTR may comprise at least 100 nucleotides, such as more than 200, 300, 400, 500, 600, 700, 800, 900, or 1000 nucleotides. Similarly, a coding sequence may include any number of nucleotides, such as at least 3, 5, 10, 20, 30, 40, 50, 60, 70, 80, 90, 100, or more nucleotides. A UTR, coding sequence, or other sequence of a nucleic acid molecule may have any nucleotide or base content or arrangement. For example, a sequence of a nucleic acid molecule may comprise any number or concentration of guanine, cytosine, uracil, and adenine bases. A nucleic acid molecule may also include non-naturally occurring (e.g., modified) nucleosides. A modified nucleoside may comprise one or more modifications (e.g., alkylations, hydroxylation, oxidation, or other modification) in its nucleobase and/or sugar moieties.

The nucleic acid molecule may comprise one or more binding regions. Binding regions may be region on the nucleic acid molecule on which a probe can hybridize. For example, a binding region may comprise a sequence which is substantially complementary with a sequence of a probe. In some cases, a binding region may correspond to a gene or a portion thereof. Each binding region may have the same or different sequences. For example, the nucleic acid molecule may comprise two binding regions having the same sequence located at different positions along a strand of the nucleic acid molecule. Alternatively, the nucleic acid molecule may comprise two or more binding regions having different sequences. Different binding regions may be interrogated by different probes. Binding regions may be located adjacent to one another or may be spatially separated along a strand of the nucleic acid molecule. As used herein with regard to two entities, "adjacent," may mean that the entities directly next to one other (e.g., contiguous) or in proximity to one another. For example, a first binding region may be directly next to a second binding region (e.g., having no other entity disposed between the first and second binding regions) or in proximity to a second binding region (e.g., having an intervening sequence or molecule between the first and second binding regions). In some cases, a double-stranded nucleic acid molecule may comprise a binding region in each strand that may be the same or different. For a nucleic acid molecule comprising multiple binding regions, the methods described herein may be performed for one or more binding regions at a time. For example, a single binding region of the multiple binding regions may be analyzed (e.g., as described herein) or two or more binding regions may be analyzed at the same time. Analyzing two or more binding regions may involve providing two or more probes, where a first probe has a sequence that is complementary to the first binding region, a second probe has a sequence that is complementary to the second binding region, etc. Each probe may further comprise one or more additional sequences (e.g., additional probe sequences, unique molecular identifiers (UMIs), or other sequences) that are different from one another such that each probe may bind to a different nucleic acid barcode molecule. In another example, where two binding regions are non-adjacent, a first binding region and a second binding region may be separated by one or more gap regions disposed between the first binding region and the second binding region. In some examples, the nucleic acid molecule (i.e., analyte) may be similar to nucleic acid molecule 2300, and the binding regions may be two sequences selected from the spacer 2318', the scaffold 2320', and the promoter 2316' sequences.

A binding region of the nucleic acid molecule may have one or more useful characteristics. For example, a binding region may have any useful length, base content, sequence, melting point, or other characteristic. A binding region may comprise, for example, at least 10 bases, such as at least 20, 25, 30, 35, 40, 45, 50, 60, 65, 70, 75, 80, 85, 90, 95, 100, 110, 120, 130, 140, 150, 160, 170, 180, 190, 200, 250, 300, 350, 400, 450, 500, or more bases. A binding region may have any useful base content and any useful sequence and combination of bases. For example, a binding region may comprise one or more adenine, thymine, uracil, cytosine, and/or guanine bases (e.g., natural or canonical bases). A binding region may also comprise one or more derivatives or modified versions of a natural or canonical base, such as an oxidized, alkylated (e.g., methylated), hydroxylated, or otherwise modified base. Similarly, a binding region may comprise ribose or deoxyribose moieties and phosphate moieties or derivatives or modified versions thereof.

In an example, a binding region may be part of a CRISPR guide molecule. For example, a binding region may be the scaffold 2320' of the CRISPR guide molecule (e.g., gRNA) 2326' of nucleic acid molecule 2300 shown in FIG. 23. In an example, a binding region may be a promoter sequence (e.g., promoter 2316') of the nucleic acid molecule 2300. The promoter sequence 2316' may be a human U6 sequence. In an example, a binding region may be the spacer sequence 2318'.

A binding region of the nucleic acid molecule may comprise one or more sequences or features, or portions thereof, of the nucleic acid molecule. For example, a binding region may comprise all or a portion of a UTR (e.g., a 3' UTR or a 5' UTR), a Kozak sequence, a Shine-Dalgarno sequence, a coding sequence, a polyA sequence (e.g., polyA tail), a cap structure, an intron, an exon, or any other sequence or feature of the nucleic acid molecule. In some examples, a nucleic acid may comprise a CRISPR guide molecule in its sequence. An example binding region may be a scaffold or backbone of the CRISPR guide molecule. Another example of a binding region may comprise a promoter sequence. In an example, a promoter sequence may comprise a U6 sequence (e.g., a human U6 sequence). An example of a nucleic acid molecule 2300 which can be analyzed according to the methods provided herein is shown in FIG. 23 and described in further detail elsewhere herein.

The nucleic acid molecule (e.g., DNA molecule, RNA molecule, such as an mRNA molecule or a nucleic acid molecule comprising a CRISPR guide molecule, e.g., nucleic acid molecule 2300 shown in FIG. 23) of a sample may be included within a cell. For example, the sample may comprise a cell comprising the nucleic acid molecule. The cell may comprise additional nucleic acid molecules that may be the same as or different from the analyte nucleic acid. In some cases, the sample may comprise a plurality of cells, and each cell may contain one or more nucleic acid molecules. The cell may be, for example, a human cell, an animal cell, or a plant cell. In some cases, the cell may be derived from a tissue or fluid, as described herein. The cell may be a prokaryotic cell or a eukaryotic cell. The cell may be a lymphocyte such as a B cell or T cell.

Access to a nucleic acid molecule included in a cell may be provided by lysing or permeabilizing the cell. Lysing the cell may release the nucleic acid molecule contained therein from the cell. A cell may be lysed using a lysis agent such as a bioactive agent. A bioactive agent useful for lysing a cell may be, for example, an enzyme (e.g., as described herein).

An enzyme used to lyse a cell may or may not be capable of carrying out additional functions such as degrading, extending, reverse transcribing, or otherwise altering a nucleic acid molecule. Alternatively, an ionic or non-ionic surfactant such as TritonX-100, Tween 20, sarcosyl, or sodium dodecyl sulfate may be used to lyse a cell. Cell lysis may also be achieved using a cellular disruption method such as an electroporation or a thermal, acoustic, or mechanical disruption method. Alternatively, a cell may be permeabilized to provide access to a nucleic acid molecule included therein. Permeabilization may involve partially or completely dissolving or disrupting a cell membrane or a portion thereof. Permeabilization may be achieved by, for example, contacting a cell membrane with an organic solvent (e.g., methanol) or a detergent such as Triton X-100 or NP-40.

A nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or a cell comprising the nucleic acid molecule or a derivative thereof (e.g., a cell bead) may be partitioned within a partition such as a well or droplet, e.g., as described herein. One or more reagents may be co-partitioned with a nucleic acid molecule or a derivative thereof or a cell comprising the nucleic acid molecule or a derivative thereof. For example, a nucleic acid molecule or a derivative thereof or a cell comprising the nucleic acid molecule or a derivative thereof may be co-partitioned with one or more reagents selected from the group consisting of lysis agents or buffers, permeabilizing agents, enzymes (e.g., enzymes capable of digesting one or more RNA molecules, extending one or more nucleic acid molecules, reverse transcribing an RNA molecule, permeabilizing or lysing a cell, or carrying out other actions), fluorophores, oligonucleotides, primers, probes, barcodes, nucleic acid barcode molecules (e.g., nucleic acid barcode molecules comprising one or more barcode sequences), buffers, deoxynucleotide triphosphates, detergents, reducing agents, chelating agents, oxidizing agents, nanoparticles, beads, and antibodies. In some cases, a nucleic acid molecule or a derivative thereof, or a cell comprising the nucleic acid molecule or a derivative thereof (e.g., a cell bead), may be co-partitioned with one or more reagents selected from the group consisting of temperature-sensitive enzymes, pH-sensitive enzymes, light-sensitive enzymes, reverse transcriptases, proteases, ligase, polymerases, restriction enzymes, nucleases, protease inhibitors, exonucleases, and nuclease inhibitors. For example, a nucleic acid molecule or a derivative thereof or a cell comprising the analyte nucleic acid molecule, or a derivative thereof may be co-partitioned with a polymerase and nucleotide molecules. Partitioning a nucleic acid molecule or a derivative thereof or a cell comprising the nucleic acid molecule or a derivative thereof and one or more reagents may comprise flowing a first phase comprising an aqueous fluid, the cell, and the one or more reagents and a second phase comprising a fluid that is immiscible with the aqueous fluid toward a junction. Upon interaction of the first and second phases, a discrete droplet of the first phase comprising the nucleic acid molecule or a derivative thereof or a cell comprising the nucleic acid molecule or a derivative thereof (e.g., a cell bead) and the one or more reagents may be formed. In some cases, the partition may comprise a single cell. The cell may be lysed or permeabilized within the partition (e.g., droplet) to provide access to the nucleic acid molecule of the cell.

In some embodiments, the cell may be lysed within the cell bead, and a subset of the intracellular contents may associate with the bead. In some cases, the cell bead may comprise thioacrydite-modified nucleic acid molecules that can hybridize with nucleic acids from the cell. For example, a poly-T nucleic acid sequence may be thioacrydite-modified and bound to the cell bead matrix. Upon cell lysis, the cellular nucleic acids (e.g., mRNA) may hybridize with the poly-T sequence. The retained intracellular contents may be released, for example, by addition of a reducing agent, e.g, DTT, TCEP, etc. The release may occur at any convenient step, such as before or after partitioning.

One or more processes may be carried out within a partition. For example, one or more processes selected from the group consisting of lysis, permeabilization, denaturation, hybridization, extension, ligation, duplication, and amplification of one or more components of a sample comprising the nucleic acid molecule may be performed within a partition. In some cases, multiple processes are carried out within a partition. The nucleic acid molecule or a cell comprising the nucleic acid molecule, may be co-partitioned with one or more reagents (e.g., as described herein) at any useful stage of the method. For example, the nucleic acid molecule contained within a cell may be co-partitioned with a probe and one or more additional reagents prior to hybridization of the probe with the binding region of the nucleic acid molecule. Similarly, the nucleic acid molecule or a cell comprising the nucleic acid molecule may be released from a partition at any useful stage of the method. For example, the nucleic acid molecule or a cell comprising the nucleic acid molecule may be released from the partition subsequent to hybridization of a binding sequence of a nucleic acid barcode molecule to a sequence of a probe hybridized to the binding region of the nucleic acid molecule. Alternatively, the nucleic acid molecule or a cell comprising the nucleic acid molecule, and/or another component of the sample comprising the same, may be released from the partition subsequent to denaturation of a complexed extended nucleic acid molecule that comprises a sequence complementary to the barcode sequence of a nucleic acid barcode molecule and a sequence complementary to the binding region of the nucleic acid molecule. Duplication and/or amplification of the extended nucleic acid molecule may then be carried out within a solution. In some cases, the solution may comprise additional extended nucleic acid molecules generated through the same process carried out in different partitions. Each extended nucleic acid molecule may comprise a different barcode sequence or a sequence complementary to a different barcode sequence. In this instance, the solution may be a pooled mixture comprising the contents of two or more partitions (e.g., droplets).

Hybridization of a probe sequence of a probe to a binding region of the nucleic acid molecule may be performed within or outside of a partition, or before partitioning. In some cases, hybridization may be preceded by denaturation of a double-stranded nucleic acid molecule to provide a single-stranded nucleic acid molecule or by lysis or permeabilization of a cell. In some cases, the hybridization may occur in a cell bead comprising a cell. The sequence of the probe that is complementary to the binding region may be situated at an end of the probe. Alternatively, this sequence may be disposed between other sequences such that when the probe sequence is hybridized to the binding region, additional probe sequences extend beyond the hybridized sequence in multiple directions. The probe sequence that hybridizes to the binding region of the nucleic acid molecule may be of the same or different length as the binding region. For example, the probe sequence may be shorter than the binding region and may only hybridize to a portion of the binding region. Alternatively, the probe sequence may be longer than the binding region and may hybridize to the entirety of the binding region and extend beyond the binding region in one or more directions. In addition to a probe sequence complementary to a binding region of the nucleic acid molecule, the probe may comprise one or more additional probe sequences. For example, the probe may comprise the probe sequence complementary to the binding region and a second probe sequence. The second probe sequence may have any useful length and other characteristics. The probe may comprise one or more additional sequences, such as one or more barcode sequences or unique molecule identifier (UMI) sequences. In some cases, one or more probe sequences of the probe may comprise a detectable moiety such as a fluorophore or a fluorescent moiety. After hybridization of one or more probes to the binding region(s) of the nucleic acid molecule, subsequent reactions including extension and/or ligation may be performed within or outside of a partition, or before partitioning.

A probe sequence of the probe may be capable of hybridizing with a sequence of a nucleic acid barcode molecule (e.g., barcode). A nucleic acid barcode molecule may comprise a first binding sequence that is complementary to a probe sequence of the probe (e.g., a second probe sequence), a barcode sequence, and a second binding sequence. A nucleic acid barcode molecule may also comprise one or more additional functional sequences selected from the group consisting of primer sequences, primer annealing sequences, and immobilization sequences. The binding sequences may have any useful length and other characteristics. In some cases, the binding sequence that is complementary to a probe sequence of the probe may be the same length as the probe sequence. Alternatively, the binding sequence may be a different length of the probe sequence. For example, the binding sequence may be shorter than the probe sequence and may only hybridize to a portion of the probe sequence. Alternatively, the binding sequence may be longer than the probe sequence and may hybridize to the entirety of the probe sequence and extend beyond the probe sequence in one or more directions. The terms nucleic acid barcode molecule and barcode may be used interchangeably.

The barcode sequence of a nucleic acid barcode molecule may have any useful length and other characteristics (e.g., as described herein). The nucleic acid barcode molecule may be attached to a support. For example, the support can be a bead such as a gel bead (e.g., as described herein). The bead may be co-partitioned with the nucleic acid molecule or the cell comprising the nucleic acid molecule. The support (e.g., bead) may comprise a plurality of nucleic acid barcode molecules that may be the same or different. The support (e.g., bead) may comprise at least 10,000 nucleic acid barcode molecules attached thereto. For example, the support (e.g., bead) may comprise at least 100,000, 1,000,000, or 10,000,000 nucleic acid barcode molecules attached thereto. In some cases, each nucleic acid barcode molecule of the plurality of nucleic acid barcode molecules may comprise a common barcode sequence. The nucleic acid barcode molecules may further comprise an additional barcode sequence that may be different for each nucleic acid barcode molecule attached to the bead. The plurality of nucleic acid barcode molecules may be releasably attached to the support (e.g., bead). The plurality of nucleic acid barcode molecules may be releasable from the support (e.g., bead) upon application of a stimulus. Such a stimulus may be selected from the group consisting of a thermal stimulus, a photo stimulus, and a chemical stimulus. For example, the stimulus may be a reducing agent such as dithiothreitol Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead. In some cases, one or more nucleic acid barcode molecules may be released from the support (e.g., bead) prior to hybridization of a binding sequence of a nucleic acid barcode molecule to a probe sequence of the probe hybridized to the nucleic acid molecule of interest. The one or more nucleic acid barcode molecules may be released from the bead within a partition including the bead and the nucleic acid molecule (or a cell comprising the nucleic acid molecule) and the probe. Releasing may take place before, after, or during hybridization of a probe sequence to a binding region of the nucleic acid molecule.

Following hybridization of a binding sequence of the nucleic acid barcode molecule to a probe sequence of the probe hybridized to the binding region of the nucleic acid molecule, the probe may be extended from an end of the probe to an end of the nucleic acid barcode molecule. Extension may comprise the use of an enzyme (e.g., a polymerase) to add one or more nucleotides to the end of the probe. Extension may provide an extended nucleic acid molecule comprising sequences complementary to the binding region of the nucleic acid molecule of interest, the barcode sequence, and one or more additional sequences of the nucleic acid barcode molecule such as one or more binding sequences. Appropriate conditions and or chemical agents (e.g., as described herein) may then be applied to denature the extended nucleic acid molecule from the nucleic acid barcode molecule and the binding nucleic acid molecule. In some cases, one or more processes may involve the use of thermosensitive agents. For example, in some cases, probes may be annealed or hybridized under one set of temperature conditions, and extension may occur under a different set of temperature conditions. In some cases, a Warm or Hot Start polymerase may be used. The nucleic acid barcode molecule and the nucleic acid molecule may then undergo further analysis. For example, a second probe that may be identical to the first probe and comprise a probe sequence that is complementary to the binding region of the nucleic acid molecule may hybridize to the binding region, and the nucleic acid barcode molecule may hybridize to an additional probe sequence of the second probe. In some cases, hybridization of the nucleic acid barcode molecule to the probe may precede hybridization of the probe to the binding region of the nucleic acid molecule. The extended nucleic acid molecule that has been released from the nucleic acid barcode molecule and the binding nucleic acid molecule may be duplicated or amplified by, for example, one or more amplification reactions. The amplification reactions may comprise polymerase chain reactions (PCR) and may involve the use of one or more primers or polymerases. The extension, denaturation, and/or amplification processes may take place within a partition. Alternatively, materials may be released from a partition prior to extension, denaturation, or amplification. For example, materials may be released from a partition between the extension and denaturation processes. Denaturation may then take place within a solution comprising the extended nucleic acid molecule, nucleic acid barcode molecule, and analyte nucleic acid molecule. Alternatively, materials may be released from a partition subsequent to denaturation and prior to amplification. In some cases, the extended nucleic acid molecule may be duplicated or amplified within a partition to provide an amplified product. The extended nucleic acid molecule, or a complement thereof (e.g., an amplified product), may be detected via sequencing (e.g., as described herein).

The presently disclosed method may be applied to a single nucleic acid molecule or a plurality of nucleic acid molecules. A method of analyzing a sample comprising a nucleic acid molecule may comprise providing a plurality of nucleic acid molecules (e.g., for gene editing, such as a nucleic acid encoding sgRNA and/or other CRISPR component), where each nucleic acid molecule comprises one or more probe binding region(s), and a plurality of probes. In some cases, the binding region of nucleic acid molecules of the plurality of nucleic acid molecules may comprise the same sequence (e.g., a constant upstream and downstream binding region). The plurality of probes may each comprise a first probe sequence complementary to a sequence of a binding region of a nucleic acid molecule (e.g., a constant upstream binding region) of the plurality of nucleic acid molecules as well as a second probe sequence. One or more probes may comprise the same first probe sequence. A first probe sequence of a probe of the plurality of probes may be hybridized to a binding region of a nucleic acid molecule of the plurality of nucleic acid molecules. A binding sequence of a nucleic acid barcode molecule of a plurality of nucleic acid barcode molecules may hybridize to the second probe sequence of a probe of the plurality of probes that is hybridized to a binding region of a nucleic acid molecule of a plurality of nucleic acid molecules. Each nucleic acid barcode molecule of the plurality of nucleic acid barcode molecules may comprise a barcode sequence and a second binding sequence. The barcode sequence of each nucleic acid barcode molecule of the plurality of nucleic acid barcode molecules may be the same or different. Following hybridization of a binding sequence of a nucleic acid barcode molecule of the plurality of nucleic acid barcode molecules to a probe sequence of a probe of the plurality of probes that is hybridized to a binding region of a nucleic acid molecule of the plurality of nucleic acid molecules, each probe of the plurality of hybridized probes may then be extended from an end of the probe to an end of the nucleic acid barcode molecule to which it is hybridized (e.g., an end of the second binding sequence of the nucleic acid barcode molecule). A plurality of extended nucleic acid molecules may thereby be created, where each extended nucleic acid molecule of the plurality of extended nucleic acid molecules comprises a sequence complementary to a binding region of a nucleic acid molecule of the plurality of nucleic acid molecules and a sequence complementary to a barcode sequence of a nucleic acid barcode molecule of the plurality of nucleic acid barcode molecules.

In some cases, one or more processes described herein may be performed within a partition. For example, each nucleic acid molecule of the plurality of nucleic acid molecules may be provided within a different partition. This may be achieved by partitioning a plurality of cells comprising the plurality of nucleic acid molecules within a plurality of separate partitions, where each cell comprises a binding nucleic acid molecule and each partition of a plurality of different partitions of the plurality of separate partitions comprises a single cell. Access to a binding nucleic acid molecule contained within a cell in a partition may be provided by lysing or permeabilizing the cell (e.g., as described herein). Nucleic acid barcode molecules provided within each partition of the plurality of different partitions of the plurality of separate partitions may be provided attached to beads. For example, each partition of the plurality of different partitions of the plurality of separate partitions may comprise a bead comprising a plurality of nucleic acid barcode molecules attached thereto (e.g., as described herein). The plurality of nucleic acid barcode molecules attached to each bead may comprise a different barcode sequence, such that each partition of the plurality of different partitions of the plurality of separate partitions comprises a different barcode sequence. Upon release of components from the plurality of different partitions of the plurality of separate partitions (e.g., following extension of each probe), each extended nucleic acid molecule may comprise a sequence complementary to a different barcode sequence, such that each extended nucleic acid molecule can be traced to a given partition and, in some cases, a given biological particle (e.g., a cell).

Chemical Ligation Methods

In another aspect, the present disclosure provides a method comprising providing a sample comprising a nucleic acid molecule (e.g., a nucleic acid molecule comprising a CRISPR guide molecule or that can be associated with the CRISPR guide molecule, such as nucleic acid molecule 2300 shown in FIG. 23) having a first binding region and a second binding region. The first binding region may be adjacent to the second binding region a first nucleic acid probe and a second nucleic acid probe. The first probe may comprise a first probe sequence and a second probe sequence, where the first probe sequence of the first probe is complementary to the first binding region of the nucleic acid molecule. The second probe may comprise a third probe sequence that is complementary to the second binding region of the nucleic acid molecule. The first probe sequence may also comprise a first reactive moiety, and the third probe sequence may comprise a second reactive moiety. The sample may be subjected to conditions sufficient to hybridize (i) the first probe sequence of the first probe to the first binding region of the nucleic acid molecule and (ii) the third probe sequence of the second probe to the second binding region of the nucleic acid molecule such that the first reactive moiety of the first probe sequence is adjacent to the second reactive moiety of the third probe sequence. The reactive moieties may then be subjected to conditions sufficient to cause them to react to yield a probe-linked nucleic acid molecule comprising the first probe linked to the second probe. The probe-linked nucleic acid molecule may then be barcoded (e.g., within a partition) to provide a barcoded probe-linked nucleic acid molecule. Barcoding may comprise hybridizing a binding sequence of a nucleic acid barcode molecule to the second probe sequence of the first probe. The first probe of the barcoded probe-linked nucleic acid molecule may subsequently be extended from an end of the first probe to an end of the nucleic acid barcode molecule to which it is hybridized to provide an extended nucleic acid molecule. The extended nucleic acid barcode molecule may comprise the first probe, the second probe, a sequence complementary to the barcode sequence of the nucleic acid barcode molecule, and a sequence complementary to another sequence (e.g., another binding sequence) of the nucleic acid barcode molecule. The extended nucleic acid molecule may be denatured from the nucleic acid barcode molecule and the nucleic acid molecule of interest and then duplicated or amplified (e.g., using polymerase chain reactions (PCR) or linear amplification) to facilitate detection of the extended nucleic acid molecule or a complement thereof (e.g., an amplified product) by, e.g., sequencing. One or more of the methods described herein may allow for genomic, transcriptomic, or exomic profiling with higher sensitivity. One or more of the methods described herein may allow for profiling of non-polyadenylated analytes (e.g., non-poly-A RNAs), splice junctions, single nucleotide polymorphism s (SNPs), fixed cells, etc. One or more of the methods described herein may be compatible for multiplexed analysis, as described elsewhere herein or in PCT Application Pub. No. WO2019/157529, which is incorporated herein by reference in its entirety. In some aspects, the multiplexed analysis may include one or more labelling agents.

In the methods and systems described herein, one or more labelling agents capable of binding to or otherwise coupling to one or more cell features may be used to characterize cells and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In a particular example, a library of potential cell feature labelling agents may be provided associated with nucleic acid reporter molecules, e.g., where a different reporter oligonucleotide sequence is associated with each labelling agent capable of binding to a specific cell feature. In some aspects, different members of the library may be characterized by the presence of a different oligonucleotide sequence label, e.g., an antibody capable of binding to a first type of protein may have associated with it a first known reporter oligonucleotide sequence, while an antibody capable of binding to a second protein (i.e., different than the first protein) may have a different known reporter oligonucleotide sequence associated with it. Prior to partitioning, the cells may be incubated with the library of labelling agents, that may represent labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a bead, such as a gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. In this way, different samples or groups can be independently processed and subsequently combined together for pooled analysis (e.g., partition-based barcoding as described elsewhere herein). See, e.g., U.S. Pat. Pub. 20190323088, which is hereby incorporated by reference its entirety.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some cases, partitioning and steps to generate (e.g., via a nucleic acid reaction, such as nucleic acid extension or ligation) a barcoded nucleic acid molecule comprising cell (e.g., partition specific) barcode sequence (or a reverse complement thereof) and reporter barcode sequence (or a reverse complement thereof) can be performed. Nucleic acid molecules derived from a cell (such as RNA molecules) can be similarly processed to append a cell (e.g., partition-specific) barcode sequence to these molecules or derivatives thereof (e.g., cDNA molecules). For example, in some embodiments, a nucleic acid barcode molecule may comprise a sequence complementary to a sequence associated with a reporter oligonucleotide or derivative thereof. Barcoded nucleic acid molecules can then be optionally processed as described elsewhere herein, e.g., to amplify the molecules and/or append sequencing platform specific sequences to the fragments. See, e.g., U.S. Pat. Pub. 20180105808, which is hereby incorporated by reference in its entirety. Barcoded nucleic acid molecules, or derivatives generated therefrom, can then be sequenced on a suitable sequencing platform.

The methods described herein may facilitate gene expression profiling with single cell resolution using, for example, chemical ligation-mediated barcoding, amplification, and sequencing. The methods described herein may allow for gene expression analysis while avoiding the use of enzymatic ligation, specialized imaging equipment, and reverse transcription, which may be highly error prone and inefficient. For example, the methods may be used to analyze a pre-determined panel of target genes in a population of single cells in a sensitive and accurate manner. In some cases, the nucleic acid molecule analyzed by the methods described herein may be a fusion gene (e.g., a hybrid gene generated via translocation, interstitial deletion, or chromosomal inversion).

The nucleic acid molecule analyzed by the method may be a single-stranded or double-stranded nucleic acid molecule (e.g., as described herein). The nucleic acid molecule may be an DNA molecule (e.g., a vector or plasmid). The nucleic acid molecule may be an RNA molecule such as an mRNA molecule. In some cases, the nucleic acid molecule may be a viral or pathogenic RNA. In some cases, the nucleic acid molecule may be a synthetic nucleic acid molecule previously introduced into or onto a cell. For example, the nucleic acid molecule may comprise a plurality of barcode sequences, and two or more barcode sequences may be binding regions of the nucleic acid molecule.

In some examples, the nucleic acid molecule may comprise one or more features selected from the group consisting of a 5' cap structure, an untranslated region (UTR), a 5' triphosphate moiety, a 5' hydroxyl moiety, a Kozak sequence, a Shine-Dalgarno sequence, a coding sequence, a codon, an intron, an exon, an open reading frame, a regulatory sequence, an enhancer sequence, a silencer sequence, a promoter sequence, and a poly(A) sequence (e.g., a poly(A) tail). Features of the nucleic acid molecule may have any useful characteristics. Additional details of nucleic acid molecules are provided in the preceding section.

The nucleic acid molecule may comprise two or more binding regions. In some cases, a binding region may correspond to a gene or a portion thereof. Each region may have the same or different sequences. For example, the nucleic acid molecule may comprise two binding regions having the same sequence located at adjacent positions along a strand of the nucleic acid molecule. Alternatively, the nucleic acid molecule may comprise two or more binding regions having different sequences at adjacent positions along a strand of the nucleic acid molecule. The nucleic acid molecule may comprise two or more binding regions flanking in between the binding regions, a variable region (e.g., a sequence encoding a CRISPR molecule or a barcode that can be used to identify the CRISPR guide molecule which may be variable among a plurality of nucleic acid molecules). As used herein with regard to two entities, "adjacent," may mean that the entities directly next to one other (e.g., contiguous) or in proximity to one another. For example, a first binding region may be directly next to a second binding region (e.g., having no other entity disposed between the first and second binding regions) or in proximity to a second binding region (e.g., having an intervening sequence or molecule between the first and second binding regions). In some cases, the nucleic acid molecule may comprise additional binding regions disposed at different locations along the same or a different strand of the nucleic acid molecule. For example, a double-stranded nucleic acid molecule may comprise one or more binding regions in each strand that may be the same or different. Different binding regions may be interrogated by different probes. For example, a first binding region may be interrogated by a first probe having a first probe sequence that is complementary to the first binding region, and a second binding region may be interrogated by a second probe having a second probe sequence that is complementary to the second binding region. The first binding region may be the constant upstream binding region and the second binding region may be the constant downstream binding region of the nucleic acid molecule, or vice versa. One or both probes may further comprise one or more additional sequences (e.g., additional probe sequences, unique molecular identifiers (UMIs), or other sequences). For example, the first probe may further comprise a second probe sequence. The second probe sequence of the first probe may undergo hybridization with a binding sequence of a nucleic acid barcode molecule. The second probe may also comprise an additional probe sequence. This sequence may be different from the second barcode sequence of the first probe so that the first and second probes may hybridize to different nucleic acid barcode molecules. The binding regions of the nucleic acid molecule may have any useful characteristics (e.g., as described in the preceding section).

The nucleic acid molecule (e.g., nucleic acid molecule 2300 shown in FIG. 23 and/or nucleic acid molecule 2400 shown in FIG. 24) of a sample may be included within a biological particle (e.g., a cell) (e.g., as described in the preceding section). For example, the sample may comprise a cell comprising the nucleic acid molecule that may be, for example, a human cell, an animal cell, or a plant cell. In some cases, the nucleic acid molecule may have been introduced into the cell, transduced the cell, penetrated the cells, transcribed in the cell, and/or expressed in the cell. For example, plasmid 2400 may be introduced in the cell which may encode and/or generate the nucleic acid molecule 2300 according to the descriptions provided elsewhere herein. Access to a nucleic acid molecule included in a cell may be provided by lysing or permeabilizing the cell (e.g., as described in the preceding section).

Hybridization of a probe sequence of a probe to a binding region of the nucleic acid molecule may be performed within or outside of a cell, partition, and/or container. In some cases, a cell may be lysed within a cell bead and a subset of the intracellular contents (e.g., nucleic acid molecule 2300 shown in FIG. 23) may be retained in the cell bead, as described elsewhere herein. In such cases, hybridization of a probe sequence of a probe to a binding region of the nucleic acid may occur prior to partitioning. In some cases, hybridization may be preceded by denaturation of a double-stranded nucleic acid molecule to provide a single-stranded nucleic acid molecule or by lysis or permeabilization of a cell. The sequence of a probe that is complementary to a binding region may be situated at an end of the probe. Alternatively, this sequence may be disposed between other sequences such that when the probe sequence is hybridized to a binding region, additional probe sequences extend beyond the hybridized sequence in multiple directions. A probe sequence that hybridizes to a binding region of the nucleic acid molecule may be of the same or different length as the binding region. For example, a probe sequence may be shorter than a binding region and may only hybridize to a portion of the binding region. Alternatively, a probe sequence may be longer than a binding region and may hybridize to the entirety of the binding region and extend beyond the binding region in one or more directions. In addition to a probe sequence complementary to a binding region of the nucleic acid molecule, a probe may comprise one or more additional probe sequences. For example, a probe may comprise a probe sequence complementary to a binding region and a second probe sequence. The second probe sequence may have any useful length and other characteristics. In an example, the first probe comprises a first probe sequence capable of hybridizing to the first binding region of the nucleic acid molecule of interest and a second probe sequence, and the second probe comprises a third probe sequence capable of hybridizing to the second binding region of the nucleic acid molecule of interest. In some cases, the second probe may further comprise a fourth binding sequence. Both the first probe and the second probe may comprise one or more additional sequences, such as one or more barcode sequences or unique molecule identifier (UMI) sequences. In some cases, one or more probe sequences of a probe may comprise a detectable moiety such as a fluorophore or a fluorescent moiety.

A probe may comprise a reactive moiety. For example, a probe sequence of a first probe capable of hybridizing to a first binding region of a nucleic acid molecule may comprise a first reactive moiety, and a probe sequence of a second probe capable of hybridizing to a second binding region of the nucleic acid molecule may comprise a second reactive moiety. When the first and second probes are hybridized to the first and second binding regions of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phorphorothioate), acids, amines, and phosphates. For example, the first reactive moiety of a first probe may comprise an azide moiety, and a second reactive moiety of a second probe may comprise an alkyne moiety. The first and second reactive moieties may react to form a linking moiety. A reaction between the first and second reactive moieties may be, for example, a cycloaddition reaction such as a strainpromoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone. Reaction between a first reactive moiety of a first probe sequence of a first probe hybridized to a first binding region of the nucleic acid molecule and a second reactive moiety of a third probe sequence of a second probe hybridized to a second binding region of the nucleic acid molecule may link the first probe and the second probe to provide a probe-linked nucleic acid molecule. Upon linking, the first and second probes may be considered ligated. Accordingly, reaction of the first and second reactive moieties may comprise a chemical ligation reaction such as a copper-catalyzed 5' azide to 3' alkyne "click" chemistry reaction to form a triazole linkage between two probes. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond.

Figures 15A, 15B, 15C, 15D, 15E:
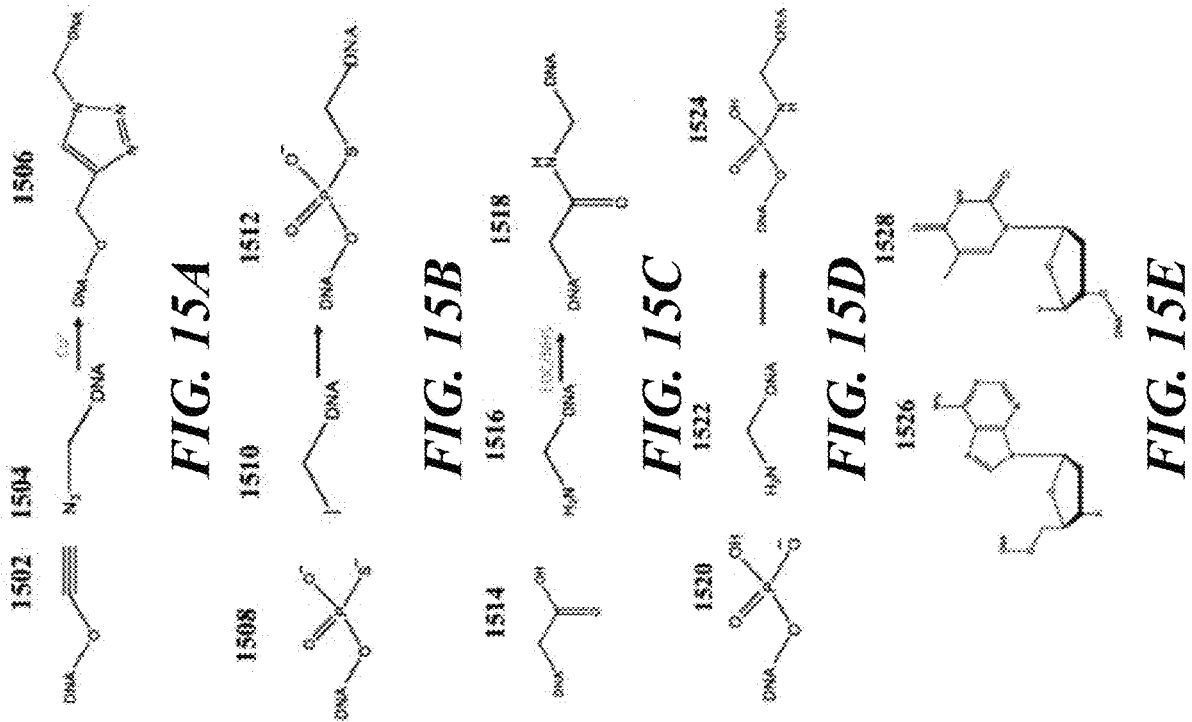
FIGS. 15A-15E shows various approaches for chemically-mediated nucleic acid ligation.

FIGS. 15A-15E illustrates examples of representative reactions. FIG. 15A shows a chemical ligation reaction of an alkyne moiety 1502 and an azide moiety 1504 reacting under copper-mediated cycloaddition to form a triazole linkage 1506. FIG. 15B shows a chemical ligation reaction of a phosphorothioate group 1508 with an iodide group 1510 to form a phosphorothioate linkage 1512. FIG. 15C shows a chemical ligation reaction of an acid 1514 and amine 1516 to form an amide linkage 1518. FIG. 15D shows a chemical ligation reaction of a phosphate moiety 1520 and an amine moiety 1522 to form a phosphoramidate linkage 1524. FIG. 15E shows a conjugation reaction of two species 1526 and 1528.

In some instances, the first and second probes are hybridized to the first and second binding regions of the nucleic acid molecule (e.g., the constant upstream binding region and the constant downstream binding region), and the first and second reactive moieties may be adjacent to one another. In some cases, the probes do not comprise reactive moieties and may be subjected to a nucleic acid reaction, providing a probe-linked nucleic acid molecule. For example, the probes may be subjected to an enzymatic ligation reaction, using a ligase (e.g., SplintR ligase and/or T4 or T4 ligase). Following the enzymatic ligation reaction, the first and second probes may be considered ligated. In one embodiment, the first and second probes are both present in a linear nucleic acid molecule. In another embodiment, the linear nucleic acid molecule is a molecular inversion probe.

In other instances, the first and second probes are hybridized to the first and second binding regions of the nucleic acid molecule (e.g., the constant upstream binding region and the constant downstream binding region), and the first and second reactive moieties may not be adjacent to one another. (e.g., comprise a gap region between the first and second probes). The first probe and the second probe may be positioned on (i.e., hybridized to) the nucleic acid molecule (e.g., mRNA) one or more nucleotides apart. For example, the first probe and the second probe may be spaced at least about 2, 3, 4, 5, 6, 7, 8, 9, 10, 11,12,13,14, 15, 16, 17, 18, 19, 20, 30, 40, 50,60, 70, 80, 90, 100, 200, 300, 400, 500, 600, 700, 800, 900, 1000 or more nucleotides apart. In some embodiments, the non-adjacent first and second probes may be ligated to form a probe-linked nucleic acid molecule. The probes may be subjected to an enzymatic ligation reaction, using a ligase, e.g., SplintR ligases, T4 ligases, PBCV1 enzymes. Gaps between the probes may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, ribonucleotides are ligated between the first and second probes. In some embodiments, deoxyribonucleotides are ligated between the first and second probes. In one embodiment, the first and second probes are both present in a linear nucleic acid molecule. In another embodiment, the linear nucleic acid molecule may form a circularized nucleic acid molecule upon hybridization to binding regions. The circularized nucleic acid molecule may then be subjected to conditions sufficient for ligation of its ends to form a circular probe-linked nucleic acid molecule.

In some alternative embodiments, the probes comprising sequences that hybridize with binding regions of the nucleic acid molecule (e.g., the constant upstream binding region and the constant downstream binding region), may be a padlock probe. A padlock probe may have a sequence complementary to at least a portion of the constant upstream binding region and have a sequence complementary to at least a portion of the constant downstream binding region. In some examples, the sequences for hybridizing with the binding regions of the nucleic acid molecule are part of the same nucleic acid molecule. For example, a first nucleic acid probe configured to hybridize to the upstream binding region of the nucleic acid molecule, and a second nucleic acid probe configured to hybridize to the downstream binding region of the nucleic acid molecule can be part of the same padlock probe molecule. Upon hybridization of the sequences of the probe that is complementary to the binding regions on the nucleic acid molecule, a circularized nucleic acid molecule may be formed. In one aspect, the methods of analysis provided can be configured to process and/or analyze specific sequences (e.g., sequences encoding a CRISPR guide molecule or a barcode sequence that identifies the CRISPR guide molecule) with a padlock probe.

A probe sequence of a probe may be capable of hybridizing with a sequence of a nucleic acid barcode molecule. In other cases, a probe may comprise a barcode molecule. A nucleic acid barcode molecule may comprise a first binding sequence that is complementary to a probe sequence of a probe (e.g., a second probe sequence), a barcode sequence, and a second binding sequence. In some cases, the binding sequence of a probe, a barcode nucleic acid molecule, or both, may be known and may bind to an analyte nucleic acid molecule (e.g., nucleic acid molecule 2300). In some cases, the binding sequence may be degenerate (i.e., randomly generated). Employing degenerate or known sequences may be used in whole transcriptome or exome analysis or for targeted RNA sequencing, respectively. A nucleic acid barcode molecule may also comprise one or more additional functional sequences selected from the group consisting of primer sequences, primer annealing sequences, and immobilization sequences. The binding sequences may have any useful length and other characteristics. In some cases, the binding sequence that is complementary to a probe sequence of a probe may be the same length as the probe sequence. Alternatively, the binding sequence may be a different length of the probe sequence. For example, the binding sequence may be shorter than the probe sequence and may only hybridize to a portion of the probe sequence. Alternatively, the binding sequence may be longer than the probe sequence and may hybridize to the entirety of the probe sequence and extend beyond the probe sequence in one or more directions.

In some cases, the barcode nucleic acid molecule may hybridize to a binding sequence of one or more probes or adapters in a specific orientation. In some embodiments, a barcode may be configured to bind to the 3' end of a probe, an adapter, or an adapter-ligated probe. In some instances, binding of a probe to a barcode molecule is direct (e.g., through direct hybridization) or indirect, e.g., using a splint sequence as described elsewhere herein (e.g., FIG. 20). In some instances, probes and/or barcode molecules may comprise one or more ribonucleotides to facilitate binding and ligation. In one non-limiting example, a binding sequence of a probe may comprise a pair of 3' terminal ribonucleotides. A barcode nucleic acid molecule may be phosphorylated at the 5' end and may associate with the ribonucleotides via a splint molecule. The barcode nucleic acid molecule may then be ligated to the 3' end of the probe. Hybridization and ligation of a barcode nucleic acid molecule at the 3' end of a probe may be advantageous as this process may minimize downstream amplification artifacts, minimize barcode exchange, and may be compatible with removal of un-ligated probes.

In some cases, a first probe with a first probe sequence capable of hybridizing with a first binding region of the nucleic acid molecule may comprise a second probe sequence capable of hybridizing with a sequence of a nucleic acid barcode molecule, and a second probe capable of hybridizing with a second binding region of the nucleic acid molecule may not comprise a sequence capable of hybridizing with a nucleic acid barcode molecule. In other cases, the second probe may also comprise a probe sequence capable of hybridizing with a sequence of a nucleic acid barcode molecule. The first nucleic acid barcode molecule to which a first probe hybridizes may be different from a second nucleic acid barcode molecule to which a second probe hybridizes. For example, the first and second nucleic acid barcode molecules may comprise one or more different binding sequences and/or different barcode sequences.

In some cases, a first probe with a first probe sequence capable of hybridizing with a first binding region of the nucleic acid molecule may comprise a second probe sequence capable of hybridizing with a first sequence of a nucleic acid adaptor molecule. The nucleic acid adaptor molecule may comprise this first sequence, or a complement thereof, and a second sequence that can hybridize with a first sequence of a nucleic acid barcode molecule. The nucleic acid adaptor molecule may also comprise a third sequence such as a primer region for downstream PCR (e.g., sequencing primer sequence), a barcode sequence, etc. The nucleic acid adaptor molecule may have any combination and derivatives or variants of the abovementioned sequences. In an example, the nucleic acid adaptor molecule may comprise a first sequence that enables hybridization of the nucleic acid adapter molecule to the first probe and a second sequence that enables hybridization of the nucleic acid adapter molecule to a nucleic acid barcode molecule. The nucleic acid barcode molecule may hybridize to the adapter molecule. In some embodiments, the nucleic acid barcode molecule can comprise additional functional sequences, such as a barcode sequence, sequencing primer sequence, a UMI, a spacer sequence, and a plurality of ribo-nucleotides.

In some examples, the barcode nucleic acid molecule may comprise a splint nucleic acid sequence. The barcode nucleic acid molecule may be partially double-stranded and comprise a binding sequence and a barcode sequence. In some cases, the binding sequence may be complementary to a portion of the first nucleic acid probe, the second nucleic acid probe, or both probes. Hybridization of the binding sequence to the first nucleic acid probe or second nucleic acid probe or both probes may occur in a partition or outside of a partition. The nucleic acid barcode molecule may then be ligated to the first nucleic acid probe, the second nucleic acid probe, or both, using, for example, chemical or enzymatic ligation.

The barcode sequence of a nucleic acid barcode molecule may have any useful length and other characteristics (e.g., as described herein). The nucleic acid barcode molecule may be attached to a support. For example, the nucleic acid barcode molecule may be attached to a bead such as a gel bead (e.g., as described herein). The bead may be co-partitioned with the nucleic acid molecule or the cell comprising the nucleic acid molecule. The bead may comprise a plurality of nucleic acid barcode molecules that may be the same or different. The bead may comprise at least 10,000 nucleic acid barcode molecules attached thereto. For example, the bead may comprise at least 100,000, 1,000, 000, or 10,000,000 nucleic acid barcode molecules attached thereto. In some cases, each nucleic acid barcode molecule of the plurality of nucleic acid barcode molecules may comprise a common barcode sequence. The nucleic acid barcode molecules may further comprise an additional barcode sequence that may be different for each nucleic acid barcode molecule attached to the bead. The plurality of nucleic acid barcode molecules may be releasably attached to the bead. The plurality of nucleic acid barcode molecules may be releasable from the bead upon application of a stimulus. Such a stimulus may be selected from the group consisting of a thermal stimulus, a photo stimulus, and a chemical stimulus. For example, the stimulus may be a reducing agent such as dithiothreitol. Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead. In some cases, one or more nucleic acid barcode molecules may be released from the bead prior to hybridization of a binding sequence of a nucleic acid barcode molecule to a probe sequence of the probe hybridized to the nucleic acid molecule of interest. The one or more nucleic acid barcode molecules may be released from the bead within a partition including the bead and the nucleic acid molecule (or a cell comprising the nucleic acid molecule) and the probe. Releasing may take place before, after, or during hybridization of a probe sequence to a binding region of the nucleic acid molecule.

Figures 10A, 10B, 10C, 10D:
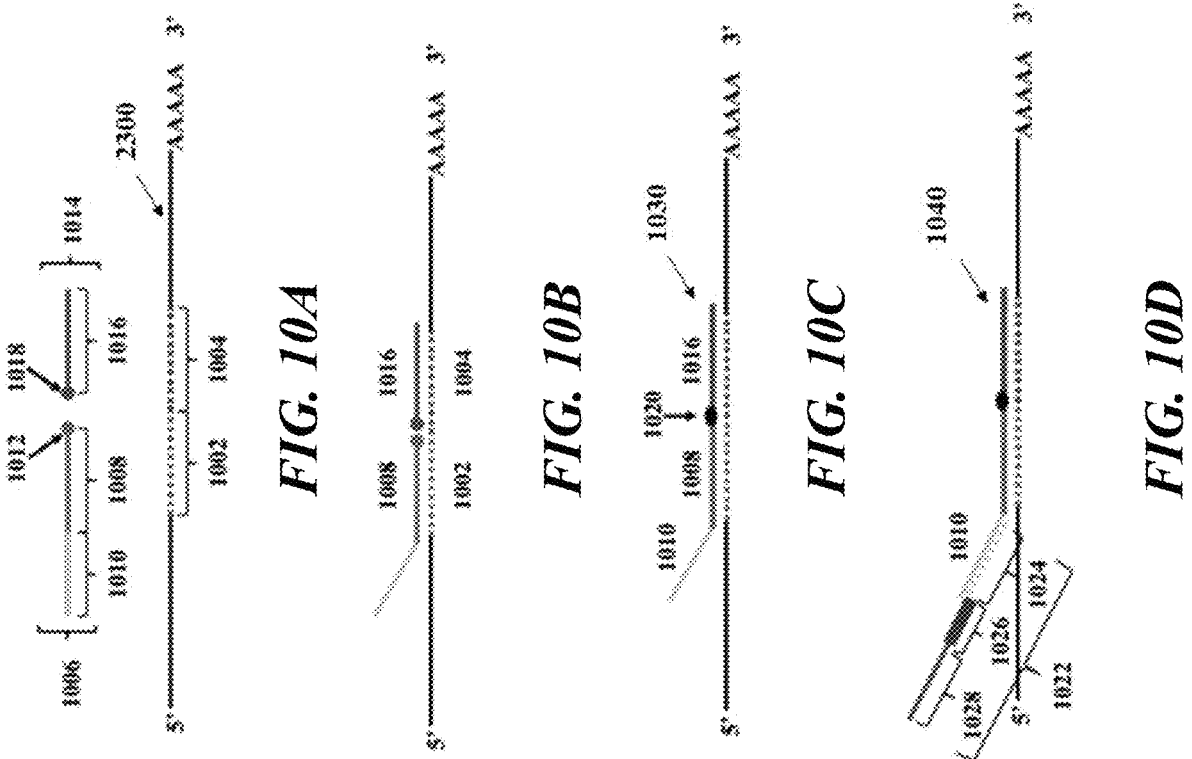
FIGS. 10A-10D schematically illustrate a method for analyzing a nucleic acid molecule.

FIGS. 10A-10D schematically illustrates a representative method of analyzing a nucleic acid molecule. FIG. 10A shows a nucleic acid molecule 2300 (e.g., nucleic acid molecule 2300 shown in FIG. 23 or another nucleic acid molecule) comprising binding regions 1002 and 1004. For example, binding region 1004 may be the scaffold 2320'. The binding region 1002 may be the spacer 2318'. In some instances, binding regions 1002 and 1004 are adjacent to one another such as shown in FIG. 10A. For example, in nucleic acid molecule 2300, the scaffold 2320' is adjacent to the spacer 2318'. In an example, a probe may be hybridized to the spacer, and another probe may be hybridized to the scaffold. Probe 1006 comprises probe sequence 1008, binding sequence 1010, and reactive moiety 1012. Probe 1014 comprises probe sequence 1016 and reactive moiety 1018. Probe sequence 1008 of probe 1006 may complementary to binding region 1002 (e.g., spacer 2318' of nucleic acid molecule 2300). Similarly, probe sequence 1016 of probe 1014 may be complementary to binding region 1004 (e.g., scaffold 2320' of nucleic acid molecule 2300). FIG. 10B shows probe sequence 1008 of probe 1006 hybridized to binding region 1002 and probe sequence 1016 of probe 1014 hybridized to binding region 1004.

In some instances, reactive moiety 1012 of probe 1006 and reactive moiety 1018 of probe 1014 are adjacent to one another. FIG. 10C shows linking moiety 1020 produced through a reaction of reactive moieties 1012 and 1018. In some cases, moieties 1012 and 1018 are ligated chemically (e.g., click chemistry), and in other cases, enzymatically (e.g., a ligase, such as SplintR or T4 ligase). Linked probes 1006 and 1014 comprise a probe-linked nucleic acid molecule 1030 comprising sequences 1010, 1008, and 1016. FIG. 10D shows nucleic acid barcode molecule 1022 comprising adapter sequence 1028, barcode sequence 1026 (which optionally may comprise a UMI sequence), and binding sequence 1024, which is complementary to binding sequence 1010. Adapter sequence 1028 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Nucleic acid barcode molecule 1022 is then hybridized to binding sequence 1010 of the probe-linked nucleic acid molecule 1030. A barcoded probe-linked nucleic acid molecule 1040 is then generated using, e.g., a nucleic acid extension reaction and/or ligation reaction as described in, e.g., FIG. 9C. In some cases, probe 1014 may comprise an additional binding sequence 1017 (not shown). Probe sequence 1017 may hybridize to another nucleic acid barcode molecule or primer with comprising a sequence complementary to probe sequence 1017. In some cases, moieties 1012 and 1018 may not be reactive and can be ligated using an enzyme (e.g., a ligase, such as SplintR, T4 ligase, etc.).

In some instances, where binding regions 1002 and 1004 are not adjacent to one another, probe 1006 and/or 1014 may be extended in a nucleic acid extension reaction and ligated together as described elsewhere herein. For example, the binding regions may be the scaffold sequence 2320' and the promoter sequence 2316' of nucleic acid molecule 2300 shown in FIG. 23. In this case, the binding regions are not adjacent to one another, and probe 1006 and/or 1014 may be extended in a nucleic acid extension reaction and ligated together as described elsewhere herein, for example in FIGS. 16A-16D, and FIGS. 25B-25E.

In some instances, following hybridization of a binding sequence 1024 of the nucleic acid barcode molecule 1022 to a binding sequence 1010 of a probe (e.g., probe-linked nucleic acid molecule 1030) hybridized to a binding region of the nucleic acid molecule 2300, the probe may be extended in a nucleic acid extension reaction to generate barcoded probe-linked nucleic acid molecule 1040. Extension may comprise the use of an enzyme (e.g., a polymerase) to add one or more nucleotides to the end of the probe and/or nucleic acid barcode molecule. Extension may provide a barcoded probe-linked nucleic acid molecule 1040 comprising sequences complementary to: (i) the first 1002 and second 1004 binding regions of the nucleic acid molecule of interest 2300, (ii) the barcode sequence, and (iii) one or more additional sequences of the nucleic acid barcode molecule such as one or more adapter sequences (e.g., adapter sequence 1028). In some instances, the barcoded probe-linked nucleic acid molecule 1040 is single stranded. In other instances, the barcoded probe-linked nucleic acid molecule 1040 is double stranded. In some instances, where the barcoded probe-linked nucleic acid molecule 1040 is single stranded, appropriate conditions and or chemical agents (e.g., as described herein) may then be applied to denature the extended nucleic acid molecule from the nucleic acid molecule. The nucleic acid molecule may then undergo further analysis. For example, another set of probes may hybridize to the binding regions of the nucleic acid molecule, and a nucleic acid barcode molecule may be appended to a probe sequence of one of the additional probes. In some cases, hybridization of the nucleic acid barcode molecule to the first probe may precede hybridization of the first and second probes to the binding region of the nucleic acid molecule. The barcoded probe-linked nucleic acid molecule 1040 may be duplicated or amplified by, for example, one or more amplification reactions, which may in some instances be isothermal. The amplification reactions may comprise polymerase chain reactions (PCR) and may involve the use of one or more primers or polymerases. The one or more primers may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), etc.) and may facilitate addition of said one or more functional sequences to the extended nucleic acid molecule. The barcoded probe-linked nucleic acid molecule 1040, or a derivative thereof, may be detected via nucleic acid sequencing (e.g., as described herein).

In some examples, nucleic acid molecule 2300 may be included in or introduced into a cell. For instance, in some examples, a cell (which may be optionally fixed) may comprise nucleic acid molecule 2300 and probes 1006 and 1014 which may hybridize to regions 1002 and 1004 (e.g., two binding regions selected from the scaffold 2320', the promoter 2316', and the spacer 2318' in nucleic acid molecule 2300 shown in FIG. 23) as described above. For example, the nucleic acid molecule 2300 may be delivered into the cell by a delivery vehicle such as a vector. In an example, a plasmid may be provided (e.g., constructed) which may be configured to express the nucleic acid molecule 2300 inside the cell according to the methods and systems described in further detail elsewhere herein. The probes may further penetrate and enter the cell, such as by cell permeabilization. Therefore, the nucleic acid molecule 2300 and the probes may become available inside the cell. The probes may hybridize to the binding regions and construct the probe-linked nucleic acid molecule.

Unbound probes may be washed away (and/or enzymatically digested) and the probes enzymatically or chemically linked together as described elsewhere herein. In some cases, the cell may then be lysed to release probe-linked nucleic acid molecule 1030 (which, in some instances, may still be hybridized to nucleic acid molecule 2300) for barcoding as described above. Alternatively, nucleic acid barcode molecule 1022 may be allowed to enter the cell for barcoding as described above.

In some examples, nucleic acid barcode molecule 1022 may be attached to a support (e.g., a bead) as described elsewhere herein. For example, nucleic acid barcode molecule 1022 may be releasably attached to a bead (e.g., via labile bond as described herein). In some instances, the bead may be a gel bead as described herein, e.g., a degradable gel bead. In some examples, a permeabilized cell comprising nucleic acid molecule 2300 may be incubated with probes 1006 and 1014 and the cell may be partitioned into a partition (e.g., a droplet or well) with nucleic acid barcode molecule 1022 (e.g., attached to a bead, such as a single bead) for barcoding. In some instances, a cell comprising nucleic acid molecule 2300, probes 1006 and 1014, and nucleic acid barcode molecule 1022 (e.g., attached to a bead, such as a single bead) may be partitioned into a partition (e.g., a droplet or well) for probe-binding and barcoding.

In some instances, the methods described herein may comprise contacting a plurality of permeabilized cells (or permeabilized nuclei or cell beads) with one or more probes (e.g., probes 1006 and 1014) targeted to one or more binding regions (e.g., 1002 and 1004 such as two sequences selected from the scaffold 2320', the promoter 2316', and the spacer 2318') within one or more nucleic acid molecules (e.g., nucleic acid molecule 2300 shown in FIG. 23 which may be encoded and/or expressed by plasmid 2400).

After probe binding and removal of excess probe, the plurality of cells and a plurality of beads (e.g., gel beads) comprising nucleic acid barcode molecules (e.g., releasably attached barcode molecules) may then be partitioned into a plurality of partitions (e.g., a plurality of droplets or a plurality of wells, e.g., in a microwell array) such that at least some partitions of the plurality of partitions comprise a single cell and a single bead. Nucleic acid probes (e.g., 1030) may then be barcoded as generally described above. Barcoded nucleic acid molecules or derivatives thereof may then be optionally further processed and analyzed by any suitable technique, including nucleic acid sequencing (e.g., Illumina sequencing).

Figures 12A, 12B, 12C, 12D, 12E:
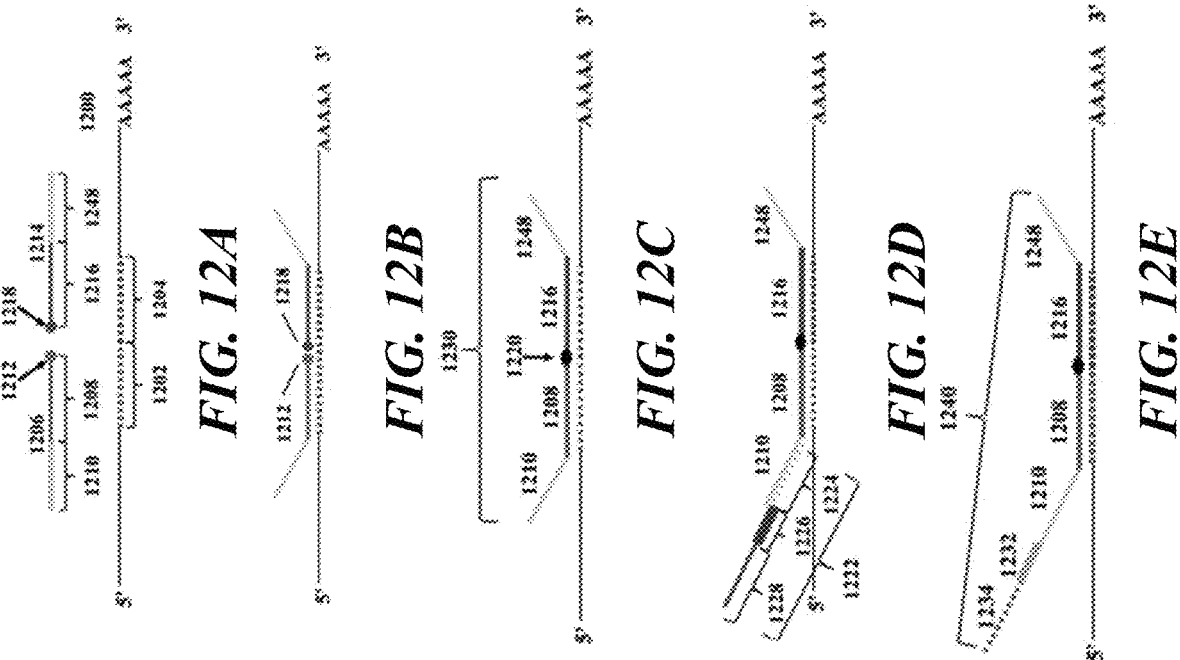
FIGS. 12A-12E schematically illustrates a method of analyzing a nucleic acid molecule.

FIGS. 12A-12E schematically illustrate a representative method of analyzing a nucleic acid molecule. The method may be used to process and/or analyze a nucleic acid molecule similar to nucleic acid molecule 2300 shown in FIG. 23 or other nucleic acid molecules. In some examples, the methods may be used to detecting a sequence of a CRISPR guide molecule, a spacer thereof, or a barcode sequence that permits identification of the CRISPR guide molecule. FIG. 12A shows a nucleic acid molecule 1200 (e.g., a mRNA molecule, the nucleic acid molecule 2300 shown in FIG. 23, or another nucleic acid molecule) comprising binding regions 1202 and 1204. In some examples, the nucleic acid molecule 1200 to be analyzed may be the same or similar to nucleic acid molecule 2300 shown in FIG. 23 and the binding regions of the nucleic acid molecule may be two sequences selected form the scaffold 2320', the spacer 2318', and the promoter 2316' sequences. In some instances, binding regions 1202 and 1204 are adjacent to one another. For example, the binding regions may be the scaffold 2320' and the spacer 2318' sequence which are adjacent to one another on nucleic acid molecule 2300 shown in FIG. 23. In other examples, the binding regions may not be adjacent to one another. For example, a binding region may be the scaffold 2320' and another binding region may be the promoter 2316'.

Probe 1206 comprises probe sequence 1208, binding sequence 1210 and reactive moiety 1212. Probe 1214 comprises probe sequences 1216, adapter sequence 1248, and reactive moiety 1216. Probe sequence 1208 of probe 1206 is complementary to binding region 1202. Similarly, probe sequence 1216 of probe 1214 is complementary to binding region 1204. FIG. 12B shows probe sequence 1208 of probe 1206 hybridized to binding region 1202 and probe sequence 1216 of probe 1214 hybridized to binding region 1204. In some instances, reactive moiety 1212 of probe 1206 and reactive moiety 1218 of probe 1214 are adjacent to one another.

FIG. 12C shows linking moiety 1220 produced through a reaction of reactive moieties 1212 and 1218. In some cases, moieties 1212 and 1218 are ligated chemically (e.g., click chemistry), and in other cases, enzymatically (e.g., a ligase, such as SplintR or T4 ligase). Linked probes 1206 and 1214 comprise a probe-linked nucleic acid molecule 1230 comprising sequences 1210, 1208, 1216, and 1248. FIG. 12D shows nucleic acid barcode molecule 1222 comprising binding sequence 1224, barcode sequence 1226 (which optionally may comprise a UMI sequence), and binding sequence 1228, which is complementary to binding sequence 1210. Adapter sequence 1228 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Nucleic acid barcode molecule 1222 is then hybridized to binding sequence 1210 of the probe-linked nucleic acid molecule 1230. A barcoded probe-linked nucleic acid molecule 1240 is then generated using, e.g., a nucleic acid extension reaction and/or ligation reaction as described previously (see, e.g., FIG. 9C). The barcoded probe-linked nucleic acid molecule 1240 may comprise sequences 1248, 1216, 1208, 1210, 1232 (complementary to barcode sequence 1226) and 1234 (complementary to adapter sequence 1228). In some instances, the barcoded probe-linked nucleic acid molecule 1240 is single stranded (e.g., only 1230 or 1222 is extended). In other instances, the barcoded probe-linked nucleic acid molecule 1240 is double stranded (e.g., both 1230 and 1222 are extended). In some instances, where the barcoded probe-linked nucleic acid molecule 1240 is single stranded, appropriate conditions and or chemical agents (e.g., as described herein) may then be applied to denature the extended nucleic acid molecule from the analyte nucleic acid molecule. The barcoded probe-linked nucleic acid molecule 1240 may be duplicated or amplified by, for example, one or more amplification reactions, which may in some instances be isothermal.

The amplification reactions may comprise polymerase chain reactions (PCR) and may involve the use of one or more primers or polymerases. The one or more primers may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), etc.) and may facilitate addition of said one or more functional sequences to the extended nucleic acid molecule. The barcoded probe-linked nucleic acid molecule 1040, or a derivative thereof, may be detected via nucleic acid sequencing (e.g., as described herein).

In some examples, nucleic acid molecule 1200 is present in a cell. In an example, the nucleic acid molecule 1200 may be similar to or the same as nucleic acid molecule 2300 shown and described in FIG. 23. In some cases, the nucleic acid molecule may be introduced into the cell, penetrate the cell, generated in the cell, expressed in the cell, or transcribed in the cell. For example, a plasmid similar to plasmid 2400 may be configured to express nucleic acid molecule 2300 in a cell. Nucleic acid molecule 2300 may be further processed according to the methods provided herein, such as using the scheme illustrated in FIG. 12. For instance, in some examples, a cell (which may in some cases be optionally fixed) comprising nucleic acid molecule 1200 (e.g., nucleic acid molecule 2300) may be permeabilized and probes 1206 and 1214 may enter the cell and hybridize to binding regions 1202 and 1204 as described above. Binding regions 1202 and 1204 may be two sequences selected from the scaffold 2320', the spacer 2318', and the promoter 2316', described in further detail elsewhere herein. The binding regions may be adjacent to one another such as shown in FIG. 12. Alternatively, the binding regions of the nucleic acid molecule (e.g., nucleic acid molecule 2300) may not be adjacent to one another, such as provided in FIGS. 16A-16D and 25B-25E.

In some examples, unbound probes may be washed away (and/or enzymatically digested) and the probes enzymatically or chemically linked together as described elsewhere herein. The cell may be lysed to release probe-linked nucleic acid molecule 1230 (which, in some instances, may still be hybridized to nucleic acid molecule 1200 or nucleic acid molecule 2300) for barcoding as described above. Alternatively, nucleic acid barcode molecule 1222 may be allowed to enter the permeabilized cell for barcoding as described above. In some embodiments, nucleic acid barcode molecule 1222 is attached to a bead as described elsewhere herein. For example, nucleic acid barcode molecule 1222 may be releasably attached to a bead (e.g., via labile bond as described herein). In some instances, the bead may be a gel bead as described herein, e.g., a degradable gel bead. In some embodiments, a permeabilized cell comprising nucleic acid molecule 1200 is incubated with probes 1206 and 1214 and the cell is then partitioned into a partition (e.g., a droplet or well) with nucleic acid barcode molecule 1222 (e.g., attached to a bead, such as a single bead) for barcoding. In other instances, a cell comprising nucleic acid molecule 1200 or nucleic acid molecule 2300, probes 1206 and 1214, and nucleic acid barcode molecule 1222 (e.g., attached to a bead, such as a single bead) are partitioned into a partition (e.g., a droplet or well) for probe-binding and barcoding. Nucleic acid barcode molecules and probes may be designed in any suitable 5' to 3' configuration. For example, a nucleic acid barcode molecule attached to a support (e.g., a bead) may be attached to the support at the 3' end of the nucleic acid barcode molecule or at the 5' end of the nucleic acid barcode molecule.

In some instances, the methods described herein comprise contacting a plurality of permeabilized cells (or permeabilized nucleic or cell beads) with one or more probes (e.g., probes 1206 and 1214) targeted to one or more regions (e.g., 1202 and 1204) within one or more nucleic acid molecules (e.g., nucleic acid molecule 2300). The binding regions of the nucleic acid molecule 2300 may be two sequences selected from the scaffold 2320', the spacer 2318', and the promoter 2316'.

After probe binding and removal of excess probe, the plurality of cells and a plurality of beads (e.g., gel beads) comprising nucleic acid barcode molecules (e.g., releasably attached barcode molecules) may then be partitioned into a plurality of partitions (e.g., a plurality of droplets or a plurality of wells, e.g., in a microwell array) such that at least some partitions of the plurality of partitions comprise a single cell and a single bead. Probes (e.g., 1230) may then be barcoded as generally described above. Barcoded nucleic acid molecules (e.g., 1240) or derivatives thereof may then be optionally further processed and analyzed by any suitable technique, including nucleic acid sequencing (e.g., Illumina sequencing).

Figures 20A, 20B, 20C, 20D:
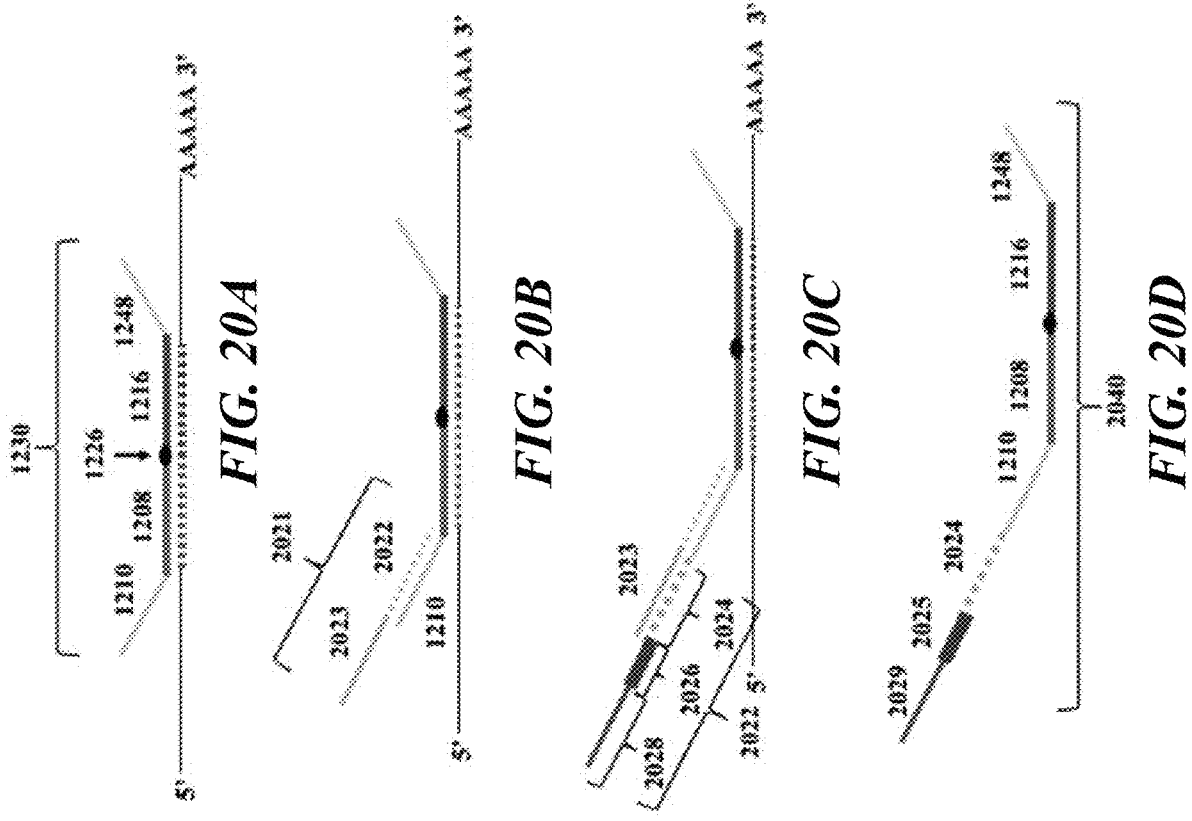
FIGS. 20A-20D schematically illustrates a method of analyzing a nucleic acid molecule.

In some cases, a nucleic acid barcode molecule (e.g., 1222) may be linked to the probe-linked nucleic acid molecule (e.g., 1230) via an adapter molecule. FIG. 20 schematically illustrates a representative method of analyzing a nucleic acid molecule using such adapter molecules. FIG. 20A shows a probe-linked nucleic acid molecule, such as those described in, e.g., FIG. 9 (e.g., 904), FIG. 10 (e.g., 1030), and FIG. 12 (e.g., 1230). FIG. 20B shows splint molecule 2021, which comprises a binding sequence 2022 complementary to a sequence of an adapter (e.g., 908, 1010, 1210, etc.) in a probe linked nucleic acid molecule (e.g., 904, 1030, 1230, etc.). The splint molecule 2021 may also comprise a binding sequence 2023. In some embodiments, the binding sequence 2023 may comprise or more ribonucleotides, such as ribo-guanines or ribo-cytosines. In some instances, the one or more ribonucleotides are present at the end (e.g., 5' terminus or 3' terminus) of the adapter sequence. In some instances, the splint molecule 2021 is a single stranded, or a partially double stranded molecule. FIG. 20C shows hybridization of a barcode nucleic acid molecule 2022 to splint molecule 2021. The barcode nucleic acid molecule 2022 comprises a adapter sequence 2028, barcode sequence 2026, and binding sequence 2024, which is complementary to binding sequence 2023 of splint molecule 2021. Adapter sequence 2028 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). In some cases, the binding sequence 2024 of the barcode nucleic acid molecule 2022 comprises a plurality of ribonucleotides, such as ribo-cytosines or ribo-guanines. In some instances, the one or more ribonucleotides are present at the end (e.g., 5' terminus or 3' terminus) of the barcode nucleic acid molecule 2022. Following hybridization of the barcode nucleic acid molecule 2022, ligation (e.g., chemically or enzymatically) of the splinted, probe-linked nucleic acid molecule and barcode molecule 2022 may occur, to form, e.g., barcoded nucleic acid molecule 2040 as shown in FIG. 20D. The barcoded probe-linked nucleic acid molecule 2040 may comprise sequences 1248, 1216, 1208, 1210, 2024 (complementary to binding sequence 2023), 2025 (complementary to barcode sequence 2026) and 1229 (complementary to adapter sequence 2028). Alternatively, the splinted, probe-linked nucleic acid molecule hybridized to the nucleic acid barcode molecule may be barcoded using a nucleic acid extension reaction as previously described. In some embodiments, a splint is not utilized, but instead the nucleic acid barcode molecule is partially double stranded and comprises a single stranded portion comprising, e.g., sequence 2022 to facilitate hybridization to probe linked molecule 2030. In some instances, the barcoded probe-linked nucleic acid molecule is single stranded. In other instances, the barcoded probe-linked nucleic acid molecule is double stranded. The extended nucleic acid molecule may subsequently be subjected to one or more amplification reactions and/or further processing, such as those described in, e.g., FIG. 12. Splint molecule 2021 may be a DNA molecule or may be an RNA molecule.

In some instances, splint molecule 2021 is pre-hybridized to the barcode nucleic acid molecule 2022 to form a splint nucleic acid molecule. The splint nucleic acid molecule may be used in, e.g., FIG. 20C to hybridize to the probe-linked nucleic acid molecule.

Figures 21A, 21B, 21C, 21D, 21E:
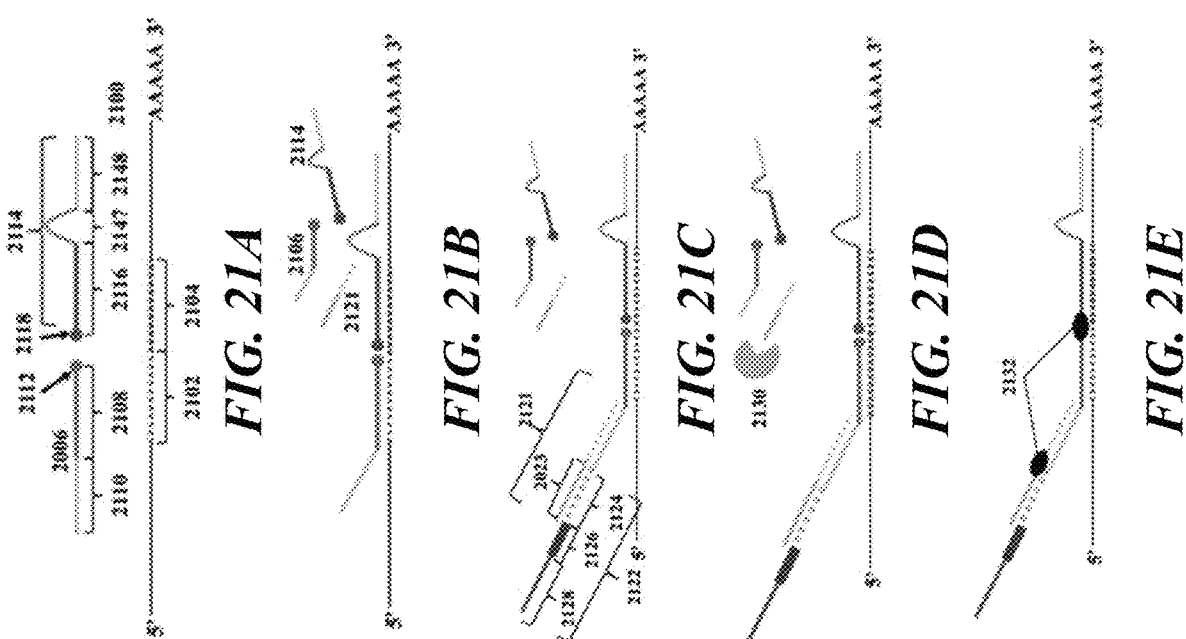
FIGS. 21A-21E schematically illustrates a method of analyzing a nucleic acid molecule.

FIG. 21 schematically illustrates a representative method of analyzing a nucleic acid molecule using first and second nucleic acid probe molecules, an adapter molecule, and a barcode nucleic acid molecule. FIG. 21A shows a nucleic acid molecule 2100 comprising adjacent binding regions 2102 and 2104. Nucleic acid molecule 2100 is an mRNA molecule comprising a polyA sequence at its 3' end. Probe 2106 comprises probe sequences 2108 and 2110 and probe 2114 comprises probe sequences 2116 and 2148 and loop sequence 2147. Probe sequence 2108 of probe 2106 is complementary to binding region 2102 and comprises reactive moiety 2112. Similarly, probe sequence 2116 of probe 2114 is complementary to binding region 2104 and comprises reactive moiety 2118. FIG. 21B shows probe sequence 2108 of probe 2106 hybridized to binding region 2102 and probe sequence 2116 of probe 2114 hybridized to binding region 2104. Reactive moiety 2112 of probe 2106 and reactive moiety 2118 of probe 2114 are adjacent to one another. An adapter molecule 2121 may also be introduced with probes 2106 and 2114. FIG. 21C shows hybridization of an adapter molecule 2121 and barcode molecule 2122. The adapter molecule 2121 comprises a binding sequence that may hybridize with probe sequence 2110 of probe 2106. The adapter molecule 2121 may also comprise a spacer sequence 2123. In some embodiments, the spacer sequence 2123 may comprise a plurality of ribonucleotides, such as ribo-guanines or ribo-cytosines. FIG. 21D shows hybridization of a barcode nucleic acid molecule 2122 to the adapter molecule 2121. The barcode nucleic acid molecule 2122 comprises a primer sequence 2128 (e.g., sequencing primer sequence), barcode sequence 2126, and binding sequence 2124, which is complementary to the spacer sequence 2123 of adapter molecule 2121. In some cases, the binding sequence 2124 of the barcode nucleic acid molecule 2122 comprises a plurality of ribonucleotides, such as ribo-cytosines or ribo-guanines. Following hybridization of the barcode nucleic acid molecule 2122. FIG. 21D illustrates digestion of excess probe molecules. An exonuclease (e.g., a 3' exonuclease) 2130 may be used to digest unhybridized probe molecules 2106, 2114 and adapter molecules 2121. FIG. 21E shows ligation of the barcode molecule and the probes. Linking moiety 2132 may be produced through a reaction of reactive moieties 2112 and 2118. In some cases, moieties 2112 and 2118 are ligated using click chemistry, and in other cases, an enzyme (e.g., SplintR, T4 ligase) may be used. Ligation of the probe molecules can produce a probe-linked molecule. Similarly, the barcode molecule 2122 may be linked by a linking moiety 2132 to one of the probes or the probe-linked molecule, generating a barcoded, probe-linked molecule. Further, extension of the linked probes of the probe-linked nucleic acid molecule may occur, to form an extended nucleic acid molecule similar to that shown in FIG. 12.

As will be appreciated, one or more processes described herein may occur inside a partition (e.g., well or droplet) or outside a partition (e.g., in bulk). One or more processes may occur in any convenient or useful order. For example, in some embodiments, a first probe may be hybridized to the nucleic acid molecule. The first probe may then be barcoded, e.g., using an adapter molecule and a barcode molecule, a splinted barcode molecule, or any combination or derivatives thereof. The barcode molecule and the probe may be ligated (e.g., using click chemistry or enzymatically). In some cases, the unhybridized probes may then be digested (e.g., using an exonuclease). Subsequently, a second probe molecule may be introduced, which may hybridize to the nucleic acid molecule, adjacent to the barcoded probe molecule. The second probe molecule may then be ligated (e.g. using click chemistry or enzymatically) to form a barcoded probe-linked nucleic acid molecule. In some cases, the barcoding may occur prior to, during, or following partitioning. Similarly, ligation and/or digestion may occur in a partition or outside of a partition.

Figures 16A, 16B, 16C, 16D:
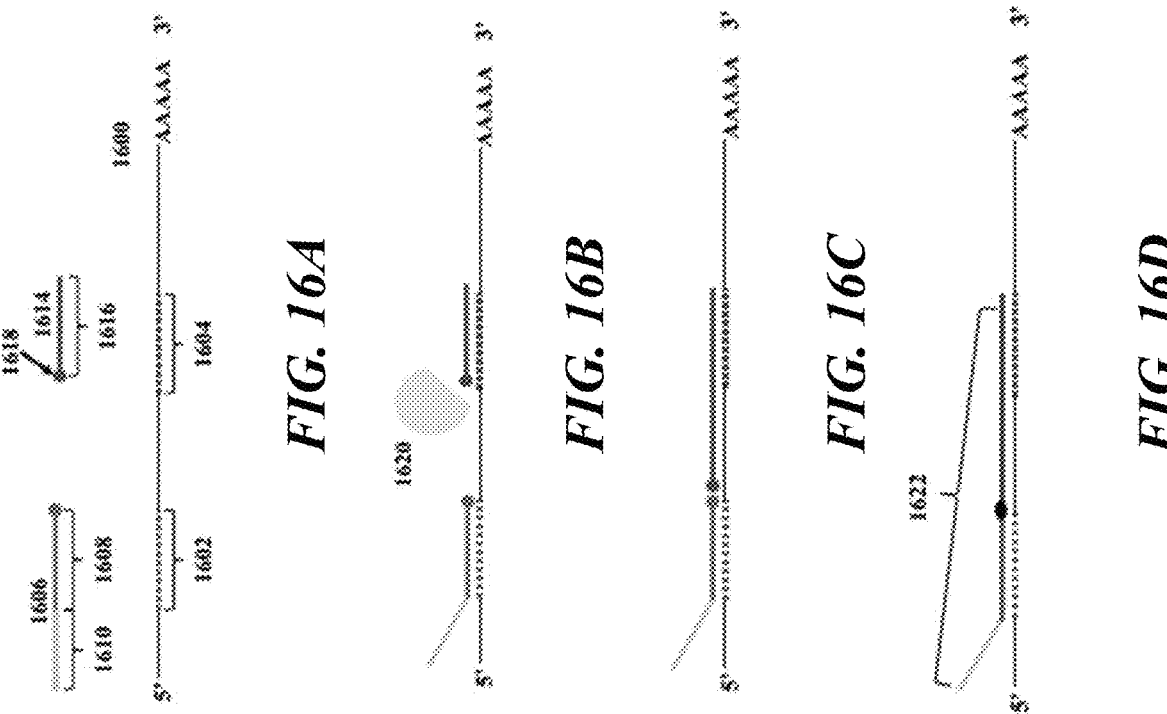
FIGS. 16A-16D shows a method for analyzing a nucleic acid molecule.

FIGS. 16A-16D schematically illustrates a method of ligating non-adjacent probes to form a probe-linked nucleic acid molecule. FIG. 16A shows a nucleic acid molecule 1600 comprising non-adjacent binding regions 1602 and 1604. In some examples, nucleic acid molecule 1600 may be an mRNA molecule comprising a polyA sequence at its 3' end. In an example, nucleic acid molecule 1600 may be the same or similar to nucleic acid molecule 2300 shown in FIG. 23. The nucleic acid molecule 1600 may comprise two binding regions 1602 and 1604 each may have a sequence complementary to a probe and configured to be hybridized to the probe. In this example, the binding regions are not adjacent to one another. The binding regions may be, for example, the scaffold 2320 and the promoter 2316' sequences of the nucleic acid molecule 2300 shown in FIG. 23 which are not adjacent to one another. The scaffold 2320' and the promoter 2316' are flanking the spacer sequence 2318'. Stated a different way, the scaffold 2320' and the promoter sequence 2316' may be two known sequences adjacent to and at the two ends of the spacer sequence 2318' which may be configured to hybridize to two probes as shown in FIG. 16, facilitating the detection of the spacer sequence 2318' using the methods and systems provided herein.

Probe 1606 comprises probe sequences 1608 and 1610 and probe 1614 comprises probe sequences 1616 and 1618. Probe sequence 1608 of probe 1606 is complementary to binding region 1602 (e.g., promoter sequence 2316 of nucleic acid molecule 2300 shown in FIG. 23). Similarly, probe sequence 1616 of probe 1614 is complementary to binding region 1604 (e.g., scaffold 2320 of nucleic acid molecule 2300 shown in FIG. 23) and comprises a moiety 1618 onto which a polymerase may bind.

FIG. 16B shows probe sequence 1608 of probe 1606 hybridized to binding region 1602 and probe sequence 1616 of probe 1614 hybridized to binding region 1604. A polymerase 1620, such as Mu polymerase or DNA polymerase, extends probe 1616 by adding complementary ribonucleotides (e.g., ribonucleoside tri-phosphate (rNTP)) or deoxyribonucleotides (e.g., deoxyribonucleotide triphosphate (dNTP)), respectively. FIG. 16C shows probes 1606 and extended probe 1614 as adjacent to one another. FIG. 16D shows a ligation reaction of probe 1606 and extended probe 1614. Ligation may occur enzymatically, for example, by using a T4RNA ligase or a PBCV1 ligase, to form a probe-linked nucleic acid molecule 1622. Downstream analysis may subsequently be performed, such as barcoding and amplification, similar to as shown in FIG. 12D-12F.

Figures 17A, 17B, 17C:
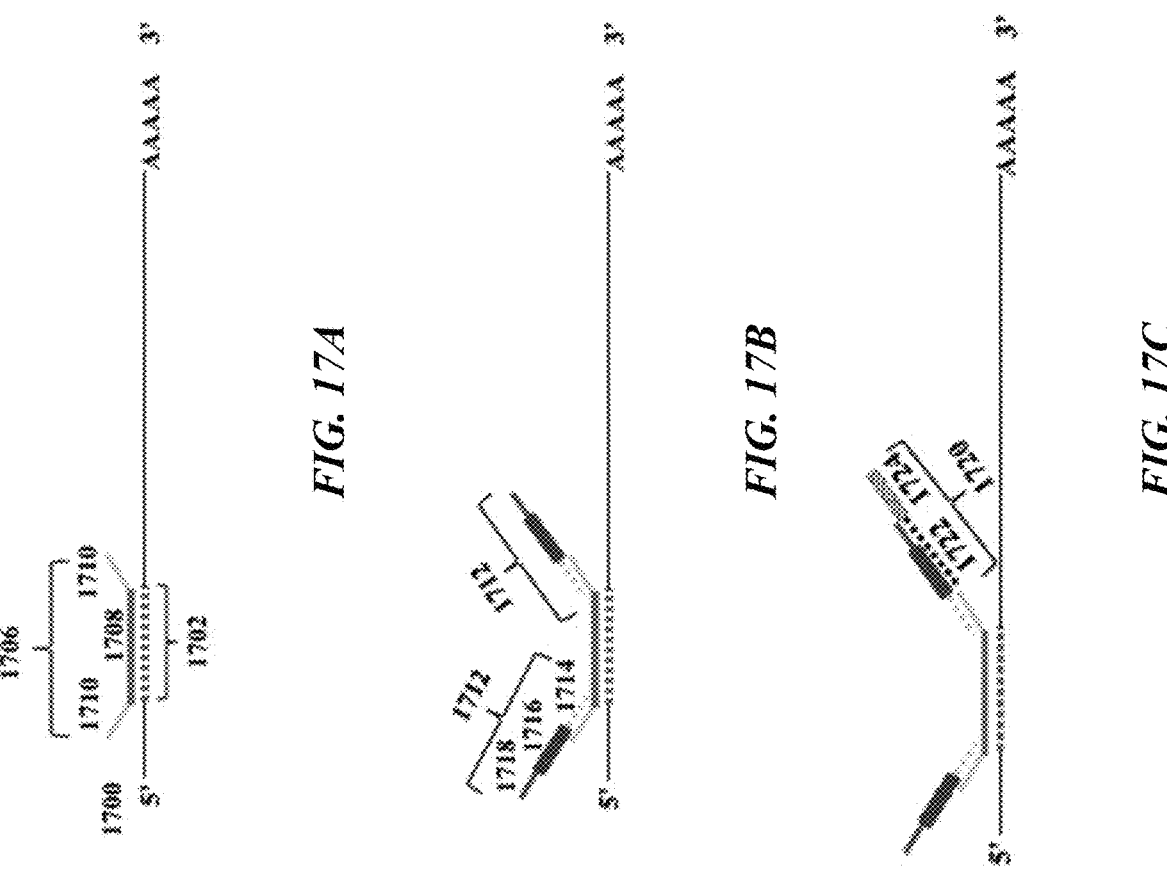
FIGS. 17A-17C illustrates a method for analyzing a nucleic acid molecule.

FIGS. 17A-17C schematically shows an alternative method barcoding nucleic acid probes using adaptor nucleic acid molecules. FIG. 17A shows a nucleic acid molecule 1700 comprising a binding region 1702. Nucleic acid molecule 1700 may be an mRNA molecule comprising a polyA sequence at its 3' end. Probe 1706 comprises probe sequences 1708 and adaptor sequences 1710. Probe sequence 1708 of probe 1706 is complementary to binding region 1702. FIG. 17B shows probe sequence 1708 of probe 1706 hybridized to binding region 1702. An adaptor nucleic acid molecule 1712 comprises a sequence 1714 that hybridizes with the adaptor sequence 1710 of the nucleic acid probe 1706, and modular sequences 1716, 1718. Modular sequences 1716, 1718 may comprise, for example, a PCR primer sequence, a barcode, a constant sequence, and/or any variants or derivatives thereof. FIG. 17C schematically shows a method of barcoding the probe nucleic acid 1706. A barcode nucleic acid molecule 1720 comprises a hybridization sequence 1722 that hybridizes with the adaptor nucleic acid molecule 1712 and a barcode sequence 1724. Hybridization of the barcode nucleic acid molecule may occur prior to or during partitioning. Following hybridization, other nucleic acid reactions may be performed, such as extension using DNA polymerase, to generate double-stranded, barcoded, nucleic acid probes (not shown). Subsequent amplification and sequencing may be performed. While FIGS. 10A-10D, 11A-11D, 12A-12E, 13A-13E, 20A-20D, and 21A-21E depict the first probe and the second probe as adjacent, it will be appreciated that these are for illustrative purposes only and are not meant to be limiting. In certain embodiments, the first probe and the second probe may not be adjacent, as depicted in FIGS. 16A-16D. Thus, any of the processes, components, reagents, variations and derivatives of FIGS. 10A-10D, 11A-11D, 12A-12E, 13A-13E, 20A-20D, and 21A-21E may also apply to probes that are non-adjacent. Similarly, any of the processes, components, reagents, variations, and derivatives of FIGS. 16A-16D may also be applicable to those schemes depicted in FIGS. 10A-10D, 11A-11D, 12A-12E, 13A-13E, 20A-20D, and 21A-21E.

In some cases, nucleic acid probe molecules that attach to the same nucleic acid molecule may be linked to one another. For example, a single probe molecule may comprise (i) a first probe moiety at a first end that comprises a sequence complementary to a first binding region of a nucleic acid molecule and (ii) a second probe moiety at a second end that comprises a sequence complementary to a second binding region of the nucleic acid molecule that is adjacent to the first binding region. A single probe molecule may comprise additional sequences, such as a sequencing primer binding site, or a primer site for downstream processing, e.g., rolling circle amplification. In some examples, the first probe and/or the second probe may comprise a cleavable linker. In some cases, the cleavable linker may comprise a restriction site and may be cleaved upon addition of a biological stimulus (e.g., restriction enzyme). In some examples, the cleavable linker may be cleaved upon the addition of a stimulus, e.g., a chemical, thermal, or photo stimulus. Upon hybridization of the first and second probe moieties to the binding nucleic acid molecule, the first and second probe moieties may be adjacent and the probe molecule and binding nucleic acid molecule may form a circular nucleic acid product. The circular nucleic acid product may then be subjected to conditions sufficient for ligation of the nucleic acid product, forming a circular probe-linked nucleic acid molecule. In some examples, the probe-linked nucleic acid molecule may be circularized. In some cases, linking of probes may occur before circularization or alternatively, linking of probes may occur simultaneously or subsequently to circularization. In some embodiments, circularization may occur via a splint nucleic acid, such as a circularization nucleic acid molecule. In such an embodiment, a circularization nucleic acid molecule may hybridize to a sequence on the first probe and a sequence on the second probe to form a circular nucleic acid product. In some embodiments, the first and second probe moieties may be connected as a single probe moiety. In some embodiments, the single probe moiety may be a circular nucleic acid product. In some embodiments, the single probe moiety may comprise single-stranded sequences that may be connected via a splint nucleic acid, such as a circularization nucleic acid molecule. Hybridization kinetics of a circular nucleic acid product may be substantially different from those of a corresponding linear product involving two disconnected probes. In some cases, the use of a single probe molecule comprising two probe moieties may result in enhanced sensitivity of a binding region of a nucleic acid molecule. For example, the use of a single probe molecule comprising two probe moieties may result in an increased number of binding nucleic acid molecules having two probe moieties attached thereto relative to the use of two disconnected probes. Circularization of nucleic acid moieties may also facilitate removal of unwanted nucleic acid species and unhybridized probes by permitting the use of exonucleases without affecting ligation products. In some cases, unwanted nucleic acid species and unhybridized probes may be removed from a solution or partition including a circular nucleic acid product subsequent to its formation. For example, a circular nucleic acid product may be formed in a solution, and unwanted and unhybridized materials removed from the solution prior to barcoding or other processing. In such an example, the circular nucleic acid product may then be partitioned with one of more materials including one or more nucleic acid barcode molecules (e.g., coupled to a bead, as described herein) or nucleic acid binding molecules to undergo further processing. Alternatively, a circular nucleic acid product may be formed within a partition and hybridize with a nucleic acid barcode molecule and/or nucleic acid binding molecule within the partition to generate a barcoded circular nucleic acid product. The barcoded circular nucleic acid product may then be released from the partition to undergo further processing. A circular nucleic acid product may be opened at any useful time. For example, the circular nucleic acid product may be open following removal of unwanted and unhybridized materials. Alternatively, the circular nucleic acid product may be opened subsequent to hybridization of a nucleic acid barcode molecule and/or nucleic acid binding molecule to the circular nucleic acid product to generate a barcoded circular nucleic acid product. In some embodiments, the circular nucleic acid product may comprise a labile or cleavable linker. For example, the circular nucleic acid product may comprise a restriction site that is recognized by one or more restriction enzymes. Addition of one or more restriction enzymes may open the nucleic acid product. In another example, the circular nucleic acid product may comprise a photo- or thermal-sensitive linker that may be cleaved upon addition of light or heat. In some cases, a circular nucleic acid product may be amplified by rolling circle amplification (RCA) prior or subsequent to partitioning of the circular nucleic acid product. The use of RCA may increase efficiency of a barcoding process by generating multiple targets from the same original ligation event. An RCA product may be less susceptible to loss prior to partitioning due to its large size. An RCA product may be digested within a partition prior to a barcoding process by hybridization of a complementary probe and a restriction enzyme or other targeted endonuclease. RCA may be used in combination with or as an alternative to PCR.

In some examples, a first nucleic acid probe or a second nucleic acid probe may comprise a sequence that allows for further processing. In some cases, the first probe or the second probe may comprise a site. In some cases, the first probe and the second probe may be connected (e.g., the first probe and the second probe are parts of the same probe) and may comprise a transposition site. In some cases, the first probe and the second probe may form a circular nucleic acid product that comprises a transposition site. In some embodiments, a transposase may be used to add sequences to the first probe or the second probe or the circular nucleic acid product. For example, a transposase may be loaded with a transposase loop sequence. The transposase loop sequence may comprise sequences that may be used for further processing. For example, the transposase loop sequence may comprise a primer sequencing site, a barcode sequence, a sequencing primer sequence, a restriction site, a UMI sequence, a spacer sequence, an adapter sequence, and any combinations, variations, or derivatives thereof. In some cases, the transposase may introduce the transposase loop sequence into the first probe, the second probe, or the circular nucleic acid molecule. In some cases, the transposase may also introduce nicks or gaps in the first probe, the second probe, or the circular nucleic acid molecule. In such cases, the nicks or gaps may be filled, e.g., using one or more enzymes (e.g., polymerase, ligase). Further processing, e.g., amplification, rolling circle amplification may generate double-stranded probe molecules. In some cases, the double-stranded probe molecules may comprise a restriction site sequence and a barcode sequence and may be cleaved, e.g., upon addition of a restriction enzyme, to generate barcoded nucleic acid fragments. Further processing may be performed, such as an amplification reaction, to generate a sequencing library.

A transposase generally refers to an enzyme that is configured to bind a nucleic acid molecule, cleave the nucleic acid molecule and insert a nucleic acid sequence into the nucleic acid molecule (and optionally fragment the molecule, e.g., a tagmentation reaction). In some cases, a transposase can be configured to bind to a specific site on the nucleic acid molecule. In some cases, a transposase can be configured to bind to a random site on the nucleic acid molecule. Moreover, in some cases, a transposase can be configured to bind and optionally fragment open chromatin (e.g., euchromatin). Non-limiting examples of transposases include: a Tn transposase (e.g., Tn3, Tn5, Tn7, Tn10, Tn552, Tn903), a MuA tranposase, a Vibhar transposase (e.g., from *Vibrio harveyi*), a prokaryotic transposase, any member of the hAT superfamily of transposases (e.g., Hermes), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnIO, and Tyl. In some cases, the transposase may be derived from any of the above, such as a transposase including one or more mutations or modifications. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. Action of a transposase (e.g., insertion) may be facilitated and/or triggered by addition of one or more cations, such as one or more divalent cations (e.g., $Ca^{2+}$, $Mg^{2+}$, or $Mn^{2+}$) In a particular aspect, the transposase is a hyperactive transposase, such as Tn5.

Figures 13A, 13B, 13C:
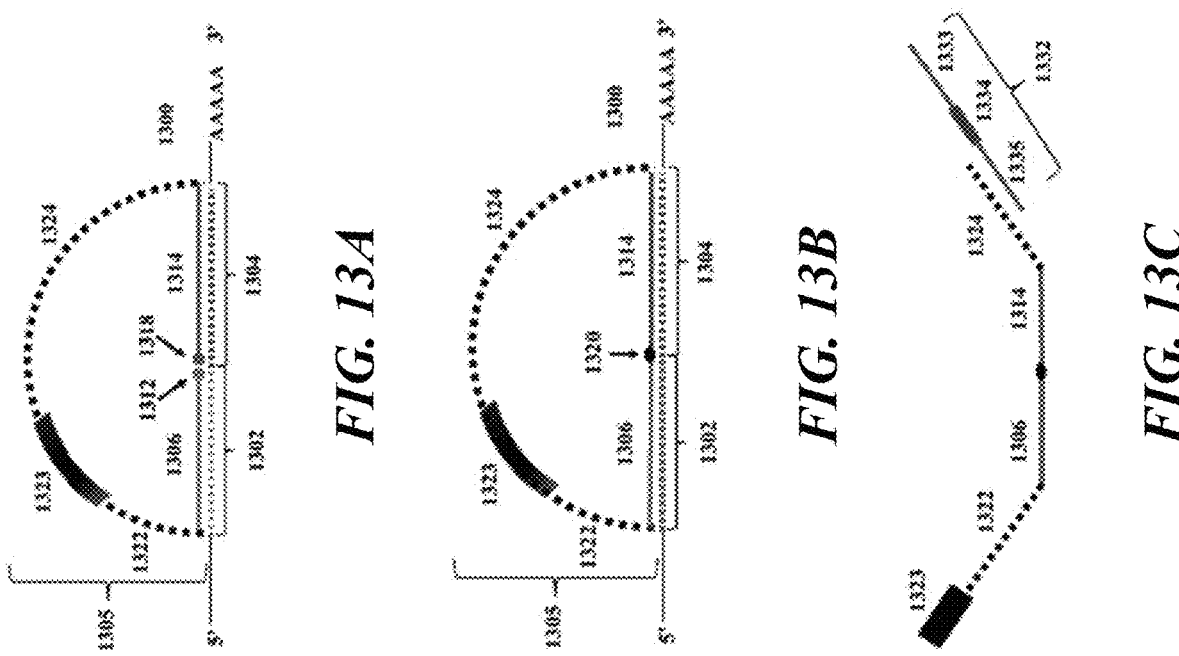
FIGS. 13A-13E schematically illustrate a method of analyzing a target nucleic acid molecule using a molecular inversion probe.

FIGS. 13A-13E schematically illustrates a representative example of nucleic acid molecule analysis. FIG. 13A shows probe molecule 1305 (e.g., a molecular inversion probe) comprising probe moiety 1306 at a first end and probe moiety 1314 at a second end. Probe moiety 1306 has a sequence complementary to binding region 1302 of nucleic acid molecule 1300 (e.g., an mRNA molecule or nucleic acid molecule 2300 shown in FIG. 23), while probe moiety 1314 has a sequence complementary to binding region 1304 of nucleic acid molecule 1300. Probe moiety 1308 may comprise reactive moiety 1312, and probe moiety 1316 may comprise reactive moiety 1318. In an example, the method shown in FIG. 13 may be used to analyze the nucleic acid molecule 2300 shown in FIG. 23. The binding regions of nucleic acid molecule 1300 may be adjacent to one another. For example, the nucleic acid molecule 1300 may be nucleic acid molecule 2300, binding region 1304 may be scaffold 1320, and binding region 1302 may be the spacer 2318'. Alternatively, binding region 1304 may be spacer 2318', and binding region 1302 may be the promoter 2316 sequence.

When probe moieties 1306 and 1314 are hybridized to nucleic acid molecule 1300 (e.g., nucleic acid molecule 2300 as described above), reactive moieties 1312 and 1318 may be adjacent. Probe moieties 1306 and 1314 are linked by a linking sequence 1330. In some instances, the linking sequence 1330 comprises adapter sequence 1322, cleavable moiety 1323, and binding sequence 1324. Adapter sequence 1322 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Linking sequence 1330 may also comprise one or more nucleic acid sequences and/or other moieties (amino acids, peptides, proteins, PEG moieties, hydrocarbon chains, or other linkers). In some embodiments, the linking sequence 1330 may comprise cleavable moiety 1323, such as a moiety comprising a thermolabile, photocleavable, or enzymatically cleavable bond. When probe moieties 1306 and 1314 are hybridized to nucleic acid molecule 1300, reactive moieties 1312 and 1318 may be adjacent.

FIG. 13B shows ligation (e.g., chemical ligation, such as using a click chemistry reaction, or enzymatic ligation such as using a ligase) of reactive moieties 1312 and 1318 to form a linking moiety 1320, thereby circularizing probe 1305. As described elsewhere herein, linking moiety 1320 may comprise a triazole moiety generated by reaction of an alkyne moiety and an azide moiety. The ligation reaction of reactive moieties 1312 and 1318 may involve the use of a catalyst such as a copper species or a strained alkene and may take place within or outside of a partition. In some embodiments, the circular nucleic acid product may be cleaved and linearized by addition of a stimulus, e.g., biological, chemical, thermal or photo-stimulus. In one non-limiting example, linking sequence 1330 may comprise a restriction site and application of a restriction enzyme cleaves site 1323, thereby linearizing 1305. In some instances, prior to barcoding, circularized probe 1305 is subjected to rolling circle amplification to generate multiple copies of probe sequence 1305. The concatemer of 1305 can be resolved to molecules suitable for barcoding by, e.g., cleaving cleavable moiety 1323. In some instances, cleavable moiety 1323 is a restriction site and the rolling circle amplification product can be cleaved by digesting the concatemer with a restriction enzyme specific of the restriction site. In some embodiments, adapter sequence 1322 comprises a UMI such that digested products from rolling circle amplification will each comprise a UMI to identify the probe 1305 of origin.

FIG. 13C shows hybridization of sequence 1335 of nucleic acid barcode molecule 1332 to binding sequence 1324. Following hybridization, linearized probe 1305 (which may or may not have been subjected to rolling circle amplification and digestion) may be barcoded by, e.g., nucleic acid extension and/or ligation as previously described herein (e.g., FIG. 9, FIGS. 10A-10D, FIGS. 12A-12e, or other methods or examples shown anywhere herein.). The barcoding reaction may be facilitated through use of a splint molecule as described elsewhere herein (e.g., FIGS. 20A-20D).

Figures 13D, 13E:
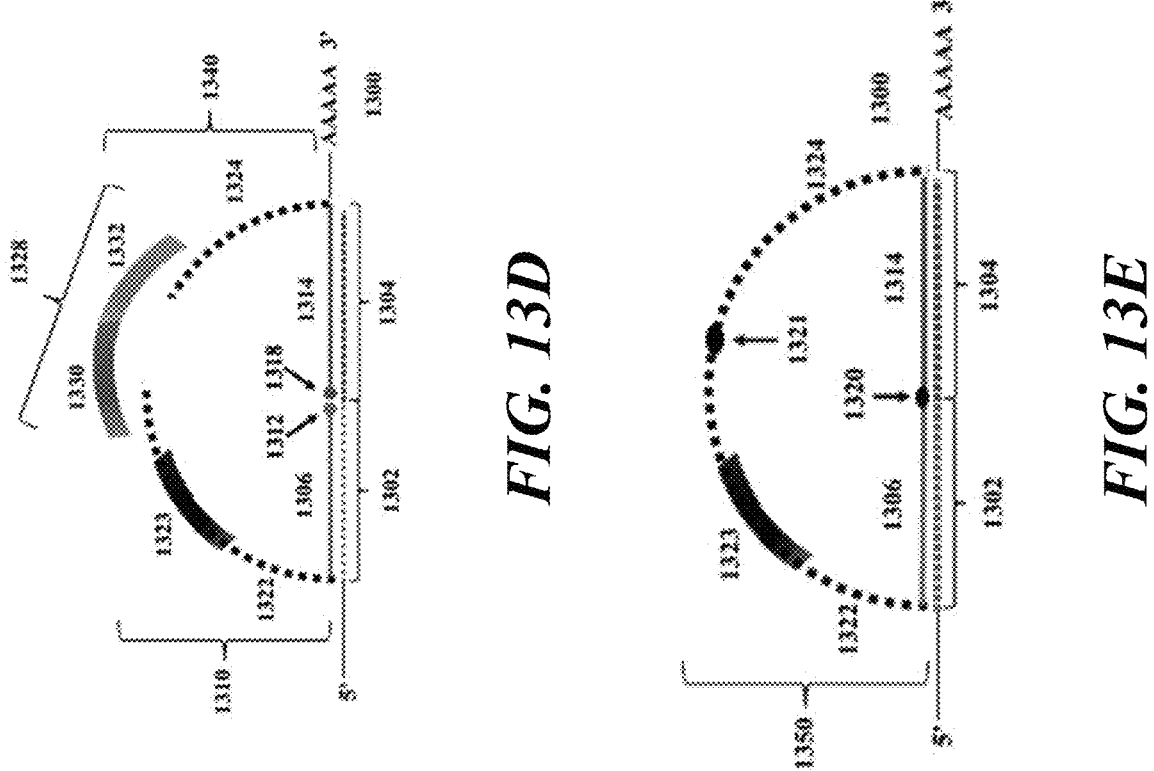

FIG. 13D shows probe molecule 1310 and probe molecule 1340 bound to nucleic acid molecule 1300. Probe molecule 1310 comprises a probe sequence 1306, adapter sequence 1322, cleavable moiety 1323 (e.g., as described above), and reactive moiety 1312. Probe sequence 1306 is complementary to binding region 1302 of nucleic acid molecule 1300 (e.g., a mRNA molecule). Probe molecule 1340 comprises probe sequence 1314, binding sequence 1324, and reactive moiety 1318. Probe sequence 1314 is complementary to binding region 1304 of nucleic acid molecule 1300 (e.g., nucleic acid molecule 2300). The binding regions on the nucleic acid molecule 2300 which can be used in this method may be two adjacent sequences selected from the spacer 2318', the scaffold 2320', and the promoter 2316', such as described elsewhere herein.

Probe molecules 1310 and 1340 may also comprise one or more additional nucleic acid sequences and/or other moieties (amino acids, peptides, proteins, PEG moieties, hydrocarbon chains, or other linkers). A circularization nucleic acid molecule 1328 may be used to connect probe molecules 1305 and 1307. The circularization nucleic acid molecule 1328 may comprise sequences 1330 and 1332. Sequence 1330 of the circularization nucleic acid molecule may be capable of hybridizing with a sequence of probe molecule 1310, and sequence 1332 of the circularization nucleic acid molecule may be capable of hybridizing with a sequence (e.g., 1324) of probe molecule 1340. After hybridization of the circularization nucleic acid molecule with probe molecules 1310 and 1340, the two molecules may be ligated together at 1321. The ligation may be chemical or enzymatic as described elsewhere herein. When probe moieties 1306 and 1314 are hybridized to nucleic acid molecule 1300, reactive moieties 1312 and 1318 may be adjacent. Probe moieties 1306 and 1314 are linked by a linking sequence

1330. The ligation of 1306 to 1314 may be chemical or enzymatic as described elsewhere herein. As described elsewhere herein, the linking moiety (e.g., 1320 or 1321) may comprise a triazole moiety generated by reaction of an alkyne moiety and an azide moiety. The ligation reaction of reactive moieties 1312 and 1318 may involve the use of a catalyst such as a copper species or a strained alkene and may take place within or outside of a partition. In some cases, moieties 1312 and 1318 may be adjacent and may not comprise reactive moieties. In such cases, moieties 1312 and 1318 may be ligated enzymatically (e.g., using a ligase). In some instances, 1310 is ligated to 1350 at 1321 prior to ligation at 1320. In some instances, 1310 is ligated to 1350 at 1320 prior to ligation at 1321. In some instances, 1310 is ligated to 1350 at 1321 and 1320 simultaneously or substantially simultaneously. The circularized molecule 1350 may be barcoded as described in previously in FIGS. 13A-13C. Barcoded molecules or derivatives thereof may then be analyzed by, e.g., nucleic acid sequencing.

One or more processes of the presently disclosed method may be carried out within a partition (e.g., as described herein). For example, one or more processes selected from the group consisting of lysis, permeabilization, denaturation, hybridization, extension, ligation, duplication, and amplification of one or more components of a sample comprising the nucleic acid molecule may be performed within a partition. In some cases, multiple processes are carried out within a partition.

The nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or a cell comprising the nucleic acid molecule or a derivative thereof (e.g., a cell bead), as well as additional components (e.g., probes, nucleic acid barcode molecules, and reagents), may be provided within a partition. In some cases, the probes may be hybridized to the binding regions of the nucleic acid molecule and linked or ligated to one another inside a partition. Alternatively, the probes may be hybridized to the binding regions of the nucleic acid molecule and linked or ligated to one another outside of a partition. For example, the nucleic acid molecule or a cell comprising the nucleic acid molecule may be provided in a container other than a partition and undergo hybridization of the probes within the initial container or another container that is not a partition. In some cases, a cell may be permeabilized (e.g., as described herein) to provide access to the nucleic acid molecule of interest therein and hybridization of the probes to the binding regions of the nucleic acid molecule of interest may take place within the cell. Ligation of the probes hybridized to the binding regions of the nucleic acid molecule may then be initiated (e.g., under suitable conditions and through introduction of an appropriate catalyst) to provide a probe-linked nucleic acid molecule. For example, reaction between a first probe comprising an azide moiety and a second probe comprising an alkyne moiety may be catalyzed by a copper catalyst. Excess probes and catalyst may then be washed away and the cell may be partitioned (e.g., as described herein) for further analysis and processing. In another example, ligation of the hybridized probes may take place within a partition. Extension, denaturation, and/or amplification processes may also take place within a partition.

The nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or the cell comprising the nucleic acid molecule or a derivative thereof (e.g., a cell bead) may be co-partitioned with one or more reagents (e.g., as described herein) at any useful stage of the method. For example, the nucleic acid molecule or a derivative thereof contained within a cell may be co-partitioned with one or more reagents following generation of the probe-linked nucleic acid molecule. Similarly, the nucleic acid molecule or a derivative thereof or a cell comprising the nucleic acid molecule or a derivative thereof may be released from a partition at any useful stage of the method. For example, the nucleic acid molecule or a derivative thereof or a cell comprising the nucleic acid molecule or a derivative thereof may be released from the partition subsequent to hybridization of a binding sequence of a nucleic acid barcode molecule to a probe-linked nucleic acid molecule (e.g., to a sequence of a probe hybridized to the binding region of the nucleic acid molecule) to provide a barcoded probe-linked nucleic acid molecule. In another example, release from the partition may take place subsequent to extension of the barcoded probe-linked nucleic acid molecule to provide an extended nucleic acid molecule that comprises a sequence complementary to the barcode sequence of a nucleic acid barcode molecule and one or more sequences complementary to one or more binding regions of the nucleic acid molecule. Alternatively, the nucleic acid molecule or a derivative thereof or a cell comprising the nucleic acid molecule or a derivative thereof may be released from a partition subsequent to denaturation of an extended nucleic acid molecule from the nucleic acid molecule and the nucleic acid barcode molecule. Duplication and/or amplification of the extended nucleic acid molecule may then be carried out within a solution. In some cases, such a solution may comprise additional extended nucleic acid molecules and/or complements thereof generated through the same process carried out in different partitions. Each extended nucleic acid molecule or complement thereof (e.g., amplified product) may comprise a different barcode sequence or a sequence complementary to a different barcode sequence. In this instance, the solution may be a pooled mixture comprising the contents of two or more partitions (e.g., droplets).

One or more additional components such as one or more reagents may be co-partitioned with a nucleic acid molecule or derivative thereof or a cell comprising a nucleic acid molecule or a derivative thereof (e.g., as described in the preceding section).

In some cases, the methods described herein may be used to facilitate gene expression analysis. For example, a nucleic acid molecule comprising a hybrid gene may be contacted by a plurality of different probes. One or more probes of the plurality of probes may have a sequence complementary to a first portion of the hybrid gene (e.g., a first binding region), and one or more probes of the plurality of probes may have a sequence complementary to a second portion of the hybrid gene (e.g., a second binding region) in proximity to the first portion of the hybrid gene. The two probes may each comprise a reactive moiety such that, upon hybridization to the hybrid gene and exposure to appropriate reaction conditions, the two probes may ligate to one another. The solution including the probe-ligated hybrid gene may undergo processing to remove unhybridized probes and may be partitioned with one or more reagents including one or more nucleic acid barcode molecules. A nucleic acid barcode molecule included within the partition including the probe-ligated hybrid gene may have a sequence complementary to a sequence of a probe hybridized to the hybrid gene and may hybridize thereto to generate a barcoded probe-ligated hybrid gene. Subsequent extension and amplification may take place within or outside of the partition. Following amplification to generate an amplified product comprising sequences of portions of the hybrid gene, or complements thereof, the amplified product may be detected using sequencing. Resultant sequence reads may be used to determine the components of the hybrid gene.

The presently disclosed method may be applied to a single nucleic acid molecule or a plurality of nucleic acid molecules. A method of analyzing a sample comprising a nucleic acid molecule may comprise providing a plurality of nucleic acid molecules (e.g., a nucleic acid molecule encoding or comprising a CRISPR guide RNA), where each nucleic acid molecule comprises a first binding region and a second binding region, a plurality of first nucleic acid probes, and a plurality of second nucleic acid probes. In some cases, one or more binding regions of nucleic acid molecules of the plurality of nucleic acid molecules may comprise the same sequence (e.g., constant binding regions). The first and second binding regions of a nucleic acid molecule of the plurality of nucleic acid molecules may be adjacent to one another. The plurality of first probes may each comprise a first probe sequence complementary to the sequence of a first binding region of a nucleic acid molecule of the plurality of nucleic acid molecules as well as a second probe sequence. A first probe sequence of a first probe of the plurality of first probes may comprise a first reactive moiety. One or more first probes of the plurality of first probes may comprise the same first probe sequence and/or the same second probe sequence. The plurality of second probes may each comprise a third probe sequence complementary to the sequence of a second binding region of a nucleic acid molecule of the plurality of nucleic acid molecules. The plurality of second probes may further comprise a fourth probe sequence. A third probe sequence of a second probe of the plurality of second probes may comprise a second reactive moiety. One or more probes of the second probes of the plurality of second probes may comprise the same third probe sequence and/or, if present, the same fourth probe sequence. A first probe sequence of a first probe of the plurality of first probes may hybridize to first binding region of a nucleic acid molecule of the plurality of nucleic acid molecules. A third probe sequence of a second probe of the plurality of second probes may hybridize to the second binding region of a nucleic acid molecule of the plurality of nucleic acid molecules. The first and third probe sequences hybridized to the first and second binding regions, respectively, of a nucleic acid molecule of the plurality of nucleic acid molecules may be adjacent to one another such that a first reactive moiety of the first probe sequence is adjacent to a second reactive moiety of the third probe sequence. The first and second reactive moieties of the first and second probes hybridized to nucleic acid molecules of the plurality of nucleic acid molecules may react to provide a plurality of probe-linked nucleic acid molecules. A binding sequence of a nucleic acid barcode molecule of a plurality of nucleic acid barcode molecules may hybridize to the second probe sequence of a first probe of the plurality of first probes that is hybridized to a first binding region of a nucleic acid molecule of a plurality of nucleic acid molecules or a probe-linked nucleic acid molecule of the plurality of probe-linked nucleic acid molecules. Each nucleic acid barcode molecule of the plurality of nucleic acid barcode molecules may comprise a barcode sequence and a second binding sequence. The barcode sequence of each nucleic acid barcode molecule of the plurality of nucleic acid barcode molecules may be the same or different. Following hybridization of a binding sequence of a nucleic acid barcode molecule of the plurality of nucleic acid barcode molecules to a second probe sequence of a first probe of the plurality of first probes that is hybridized to a first binding region of a nucleic acid molecule of the plurality of nucleic acid molecules or a probe-linked nucleic acid molecule of the plurality of probe-linked nucleic acid molecules, each first probe of the plurality of hybridized probes may then be extended from an end of the probe to an end of the nucleic acid barcode molecule to which it is hybridized (e.g., an end of the second binding sequence of the nucleic acid barcode molecule). A plurality of extended nucleic acid molecules may thereby be created, where each extended nucleic acid molecule of the plurality of extended nucleic acid molecules comprises a sequence complementary to the first binding region of a nucleic acid molecule of the plurality of nucleic acid molecules, a sequence complementary to the second binding region of a nucleic acid molecule of the plurality of nucleic acid molecules, a second probe sequence of a first probe of the plurality of first probes, a sequence complementary to a barcode sequence of a nucleic acid barcode molecule of the plurality of nucleic acid barcode molecules, and one or more sequences complementary to one or more additional sequences (e.g., binding or barcode sequences) of a nucleic acid barcode molecule of the plurality of nucleic acid barcode molecules.

In some aspects, one or more nucleic acid molecules may be analyzed including a nucleic acid molecule related to gene editing, such as a nucleic acid encoding sgRNA and/or other CRISPR component(s) and other molecules. In some cases, one or more analyte types may be barcoded and analyzed without the need for reverse transcription, including e.g., molecules for analyzing gene expression (targeted RNA) and molecules for gene editing.

In some cases, one or more processes described above may be performed within a partition. For example, each nucleic acid molecule of the plurality of nucleic acid molecules may be provided within a different partition. This may be achieved by partitioning a plurality of cells comprising the plurality of nucleic acid molecules within a plurality of separate partitions, where each cell comprises a nucleic acid molecule and each partition of a plurality of different partitions of the plurality of separate partitions comprises a single cell. The plurality of cells may be partitioned prior or subsequent to hybridization of probes to binding regions of the nucleic acid molecules of interest included therein and linking of the probes to provide probe-linked nucleic acid molecules. Access to a nucleic acid molecule or derivative thereof (e.g., as described herein) contained within a cell in a partition may be provided by lysing or permeabilizing the cell (e.g., as described herein). Nucleic acid barcode molecules provided within each partition of the plurality of different partitions of the plurality of separate partitions may be provided attached to beads. For example, each partition of the plurality of different partitions of the plurality of separate partitions may comprise a bead comprising a plurality of nucleic acid barcode molecules attached thereto (e.g., as described herein). The plurality of nucleic acid barcode molecules attached to each bead may comprise a different barcode sequence, such that each partition of the plurality of different partitions of the plurality of separate partitions comprises a different barcode sequence. Upon release of components from the plurality of different partitions of the plurality of separate partitions (e.g., following extension of each probe), each extended nucleic acid molecule may comprise a sequence complementary to a different barcode sequence, such that each extended nucleic acid molecule can be traced to a given partition and, in some cases, a given cell.

Figure 14:
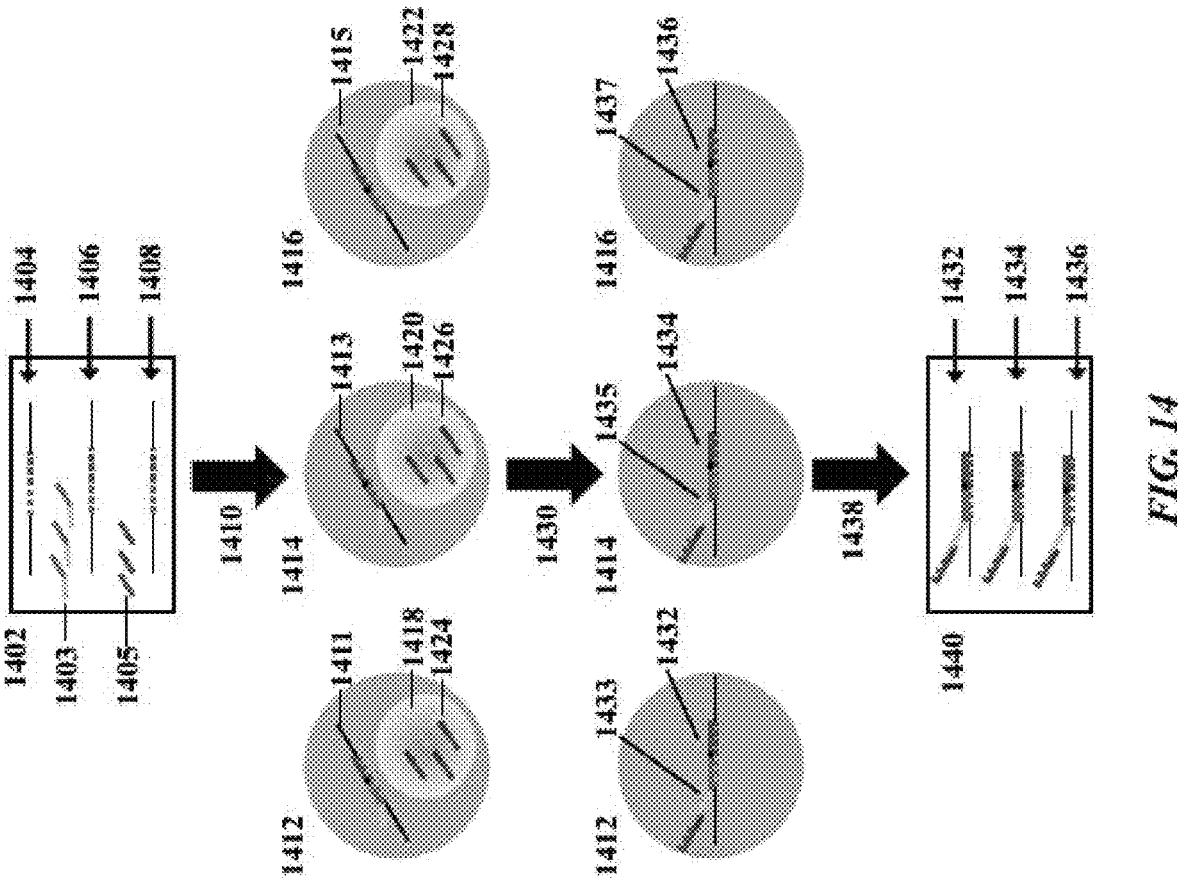
FIG. 14 shows an example workflow for analysis of a plurality of nucleic acid molecules involving co-partitioning nucleic acid molecules with barcoded beads within droplets.

FIG. 14 illustrates a sample workflow for a method of analyzing a plurality of nucleic acid molecules comprising chemical-ligation mediated amplification. Nucleic acid molecules 1404, 1406, and 1408 are provided within container 1402. Each nucleic acid molecule comprises a first binding region and a second binding region indicated by dashed lines. The first binding regions of each nucleic acid molecule may be the same or different. Similarly, the second binding regions of each nucleic acid molecule may be the same or different. In an example, the nucleic acid molecule 1404 may be the same or similar to nucleic acid molecule 2300 shown in FIG. 23. In some examples, the two binding regions may not be adjacent to one another. For example, a binding region may be scaffold 2320 and another binding region may be promoter 2316. The two binding regions may be flanking the spacer sequence 2318'. In other examples, the two binding regions may be adjacent to one another and may include the spacer sequence 2318'. The two binding regions may be two sequences selected from the scaffold 2320', spacer 2318', and the promoter 2316' according to the methods described anywhere herein.

A plurality of first probes 1403 and a plurality of second probes 1405 may be provided in container 1402. First probes of the plurality of first probes 1403 may comprise a first probe sequence that is complementary to the first binding region of nucleic acid molecule 1404, 1406, and/or 1408 and a second probe sequence. First probe sequences of the plurality of first probes 1403 may comprise a first reactive moiety. Second probes of the plurality of second probes 1405 may comprise a third probe sequence that is complementary to the second binding region of nucleic acid molecule 1404, 1406, and/or 1408. Third probe sequences of the plurality of second probes 1405 may comprise a second reactive moiety. A first probe sequence of first probes of the plurality of first probes 1403 may hybridize to the first binding regions of nucleic acid molecules 1404, 1406, and 1408. Similarly, a second probe sequence of second probes of the plurality of second probes 1405 may hybridize to the second binding regions of nucleic acid molecules 1404, 1406, and 1408. The first and second reactive moieties of the first and third probe sequences may then react to provide probe-linked nucleic acid molecules 1411, 1413, and 1415.

In process 1410, probe-linked nucleic acid molecules 1411, 1413, and 1415 may be co-partitioned with beads 1418, 1420, and 1422 into separate droplets 1412, 1414, and 1416 such that each droplet includes a single probe-linked nucleic acid molecule and a single bead. Each bead may comprise a plurality of nucleic acid barcode molecules attached thereto. Bead 1418 comprises nucleic acid barcode molecule 1424, bead 1420 comprises nucleic acid barcode molecule 1426, and bead 1422 comprises nucleic acid barcode molecule 1428. Nucleic acid barcode molecules 1424, 1426, and 1428 each comprise first and second binding sequences and a barcode sequence. The barcode sequences of nucleic acid barcode molecules 1424, 1426, and 1428 are different such that each droplet comprises a different barcode sequence.

In process 1430, nucleic acid barcode molecules 1424, 1426, and 1428 are released from their respective beads (e.g., by application of a stimulus that degrades or dissolves the bead) within their respective droplets. A binding sequence of nucleic acid barcode molecules 1424, 1426, and 1428 hybridizes to the second probe sequence of probe-linked nucleic acid molecules 1411, 1413, and 1415, respectively, to provide a barcoded probe-linked nucleic acid molecule within each droplet. The barcoded probe-linked nucleic acid molecule within each droplet then undergoes extension to provide complexed extended nucleic acid molecules 1432, 1434, and 1436 comprising extended nucleic acid molecules 1433, 1435, and 1437. Extended nucleic acid molecules 1433, 1435, and 1437 comprise sequences complementary to a barcode sequence and the sequences of the binding regions of the nucleic acid molecule from which they derive. For example, extended nucleic acid molecule 1433 comprises sequences complementary to the sequences of the binding regions of nucleic acid molecule 1404 and a sequence complementary to the barcode sequence of nucleic acid barcode molecule 1424.

In process 1438, the contents of droplets 1412, 1414, and 1416 are pooled to provide a pooled mixture 1440 comprising complexed extended nucleic acid molecules 1432, 1434, and 1436. Complexed extended nucleic acid molecules 1432, 1434, and 1436 may then be denatured from the nucleic acid molecule and nucleic acid barcode molecule to which they are hybridized to provide extended nucleic acid molecules 1433, 1435, and 1437. Extended nucleic acid molecules 1433, 1435, and 1437 may then be amplified to provide amplified products corresponding to each extended nucleic acid molecule. The amplified products will comprise sequences that are the same or substantially the same as the barcode sequence and sequences of the binding regions of the nucleic acid molecule from which they derive. For example, the amplified product corresponding to extended nucleic acid molecule 1433 comprises sequences that are the same or substantially the same as the sequences of the binding regions of nucleic acid molecule 1404 and a sequence that is the same or substantially the same as the barcode sequence of nucleic acid barcode molecule 1424. Because each extended nucleic acid molecule and each amplified product comprises a different barcode sequence or complement thereof, the extended nucleic acid molecules and amplified products can be traced back to particular nucleic acid molecules and, in some cases, to particular cells. This barcoding method may therefore facilitate rapid analysis of nucleic acid molecules through, for example, sequencing without the need for reverse transcription In one aspect, the present invention provides methods of analysis that are configured to process and/or analyze specific sequences (e.g., RNA sequences) with a molecular inversion probe. In one embodiment, the molecular inversion probe can form a circularized nucleic acid molecule upon hybridization to target-specific sequences.

Figure 18:
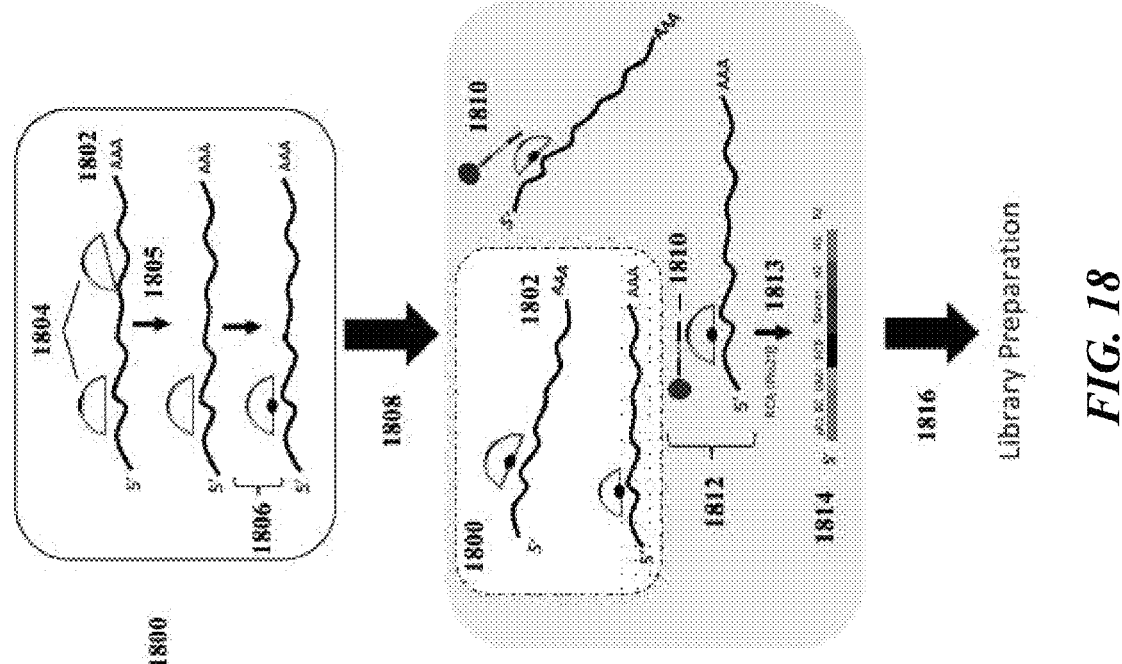
FIG. 18 schematically shows a method of analyzing a nucleic acid molecule.

FIG. 18 illustrates an example workflow for a method of analyzing a plurality of nucleic acid molecules comprising enzymatic ligation-mediated amplification. Cell 1800 may be a fixed and permeabilized cell comprising nucleic acid molecules 1802. Each nucleic acid molecule 1802 comprises a first binding region and a second binding region. The first binding regions of each nucleic acid molecule may be the same or different. Similarly, the second binding regions of each nucleic acid molecule may be the same or different. The first and second binding regions of each nucleic acid molecule may be adjacent to one another. The nucleic acid molecule 1802 may be nucleic acid molecule 2300 shown in FIG. 23 and the binding regions of nucleic acid molecule 2300 may be according to the descriptions provided anywhere herein.

A plurality of first probes 1804 comprising first and second probe sequences that hybridize with the first and second binding regions, respectively, may be introduced into the cell 1800. The probes 1804 may be provided as linear molecules and may comprise adapter sequences such as a PCR primer region, a sequencing site primer region, and/or a spacer region, as described elsewhere herein. The first probe sequence of the plurality of probes 1804 may hybridize to the first binding regions of nucleic acid molecules 1802 (e.g., nucleic acid molecule 2300). Upon hybridization of the probes to the binding regions, a circularized nucleic acid molecule may be formed. Similarly, the second probe sequence of the plurality of probes 1804 may hybridize to the second binding regions of nucleic acid molecules 1802. In some cases, the first probe sequence and the second probe sequence are adjacent to each other. In some cases, they are non-adjacent and may be ligated using polymerases, e.g., Mu polymerase, as described elsewhere herein. In some cases, the first and second probe sequences of probes 1804 comprise reactive moieties. Following hybridization, excess, unhybridized probes may be removed via a wash step 1805. The first and second probe sequences may then be connected via introduction of enzymes (e.g., polymerases, ligases) or through a chemical reaction (e.g., click chemistry of reactive moieties), generating a probe-linked nucleic acid molecule 1806.

In process 1808, probe-linked nucleic acid molecules 1806 within cell 1800 may be co-partitioned with barcode nucleic acid molecules 1810. The barcode nucleic acid molecules may comprise adaptor regions including, but not limited to, a unique molecular identifier sequence, a PCR primer sequence, a spacer sequence, and sequencing site primer region. The barcode nucleic acid molecules may be attached to beads (not shown). Each bead may comprise a plurality of nucleic acid barcode molecules attached thereto. A binding sequence of nucleic acid barcode molecule 1810 hybridizes to a sequence of the probe 1804 of the probe-linked nucleic acid molecules 1806, to provide a barcoded probe-linked nucleic acid molecule 1812. The barcoded probe-linked nucleic acid molecule 1812 then undergoes a nucleic acid reaction 1813 such as amplification, e.g., Phi29-based rolling circle amplification, to provide barcoded amplicons of interest 1814, which comprise sequences complementary to the sequences of the binding regions of nucleic acid molecule 1802, a sequence complementary to the barcode sequence of nucleic acid barcode molecule 1810, and any adaptor sequences of probe 1804.

In process 1816, the contents of the one or more partitions are pooled. Barcoded amplicons of interest 1814 may then be subjected to conditions sufficient for library preparation. In some cases, the barcoded amplicons of interest may be subjected to nucleic acid reactions, such as amplification (e.g., PCR). The amplified products will comprise sequences that are the same or substantially the same as the barcode sequence and sequences of the binding regions of the nucleic acid molecule from which they derive. The amplified products can be traced back to particular nucleic acid molecules and, in some cases, to particular cells. This barcoding method may therefore facilitate rapid analysis of nucleic acid molecules through, for example, sequencing without the need for reverse transcription.

Figure 19:
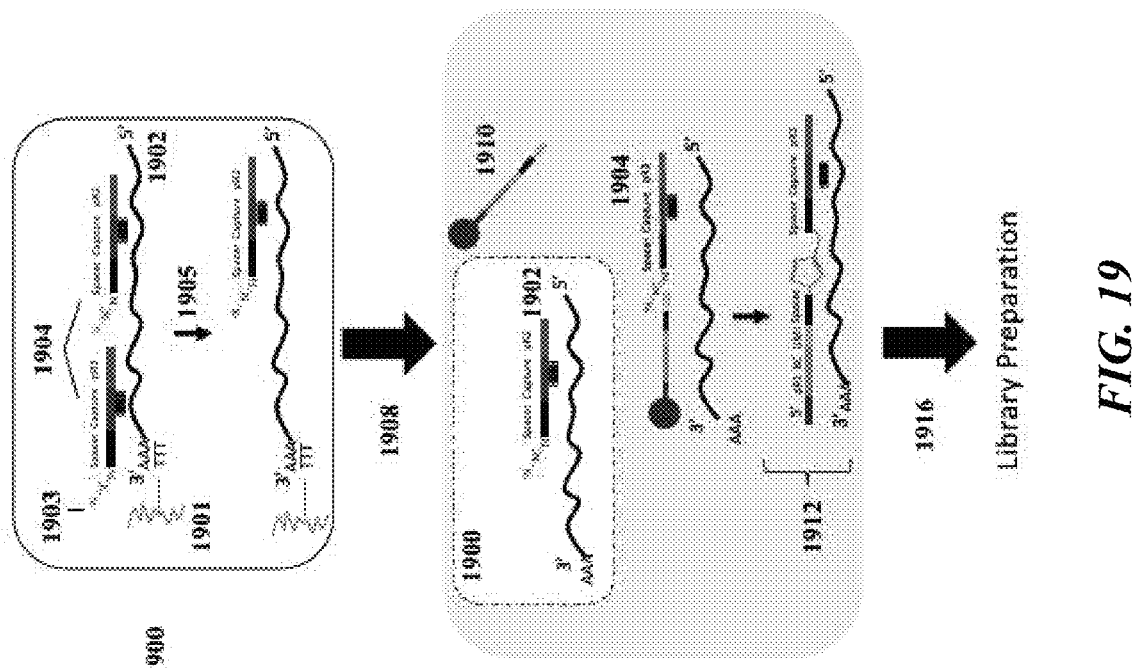
FIG. 19 schematically shows another example method of analyzing a nucleic acid molecule.

FIG. 19 illustrates an example workflow for a method of analyzing a plurality of nucleic acid molecules comprising chemical ligation-mediated amplification of nucleic acids in cell beads. Cell 1900 may be a cell bead comprising dissolvable nucleic acid molecule capture moieties 1901. These moieties may comprise or be thioacrydite-conjugated nucleic acid molecules that may be bound to the gel bead matrix. Within the cell bead are nucleic acid molecules 1902 (e.g., nucleic acid molecule 2300), which comprise a binding region. A plurality of first probes 1904 comprising a probe sequence that hybridizes with the binding region, respectively, may be introduced into the cell bead 1900. The probes 1904 may additionally comprise adapter sequences such as a PCR primer region, a sequencing site primer region, and/or a spacer region, as described elsewhere herein. The probes 1904 may also comprise a reactive moiety 1903. Following hybridization, excess, unhybridized probes may be removed via a wash step 1905.

In process 1908, the cell bead 1900 comprising nucleic acid molecules 1902 (e.g., nucleic acid molecule 2300) is co-partitioned with barcode nucleic acid molecules 1910 which comprise a reactive moiety. The partition comprises conditions sufficient to release the nucleic acid molecules 1902 from the cell bead matrix. In some cases, a reducing agent such as DTT may be used to release the nucleic acid molecules from the cell bead into the partition. The barcode nucleic acid molecules may be attached to beads (not shown). Each bead may comprise a plurality of nucleic acid barcode molecules attached thereto. The partition may comprise conditions sufficient to release the nucleic acid barcode molecules from the beads into the partition. The barcode nucleic acid molecule 1910 may associate with the probe 1904 that is hybridized to the nucleic acid molecule 1902. The barcode nucleic acid molecule 1910 and the probe 1904 may then be ligated, e.g., via click chemistry of the reactive moieties on the barcode nucleic acid molecule and the reactive moiety on the probe 1904, to provide a barcoded, probe-linked nucleic acid molecule 1912. Reaction yield may be enhanced, for example, by incorporating splint nucleic acid sequences that hybridize with the spacer adapter sequences. For example, the barcode nucleic acid molecule 1910 may comprise a sequence (e.g., overhang sequence, not shown) that may hybridize with an adapter sequence (e.g., spacer sequence) on the probe 1904. Following hybridization, the reactive moieties on the barcode nucleic acid molecule 1910 and the reactive moiety on the probe 1904 may be ligated to provide a barcoded, probe-linked nucleic acid molecule. In other non-limiting examples, the barcode nucleic acid molecule 1910 may be partially double-stranded and comprise a sequence (e.g., overhang sequence) to form a splint nucleic acid sequence that can partially hybridize with the probe 1904 and be ligated to provide a barcoded, probe-linked nucleic acid molecule that is partially double-stranded.

In process 1916, the contents of the one or more partitions are pooled. The barcoded probe-linked nucleic acid molecules 1912 may then be subjected to conditions sufficient for library preparation. In some cases, the barcoded probe-linked nucleic acid molecules are cleaned up. In a non-limiting example of cleanup, samples may be enriched or purified via a magnetic-based pulldown assay of the of nucleic acid molecules. In some cases, the cleanup process may allow for size selection of nucleic acid molecules. In some cases, the cleanup process comprises removing DNA-templated ligation products. In other cases, the cleanup process comprises RNAse to cleave the RNA strand, e.g., in a DNA-RNA duplex. In some cases, the cleanup process comprises a pulldown assay (e.g., biotin pulldown of a ligation handle). In some cases, the cleanup process comprises post-ligation exonuclease treatment. In some cases, the cleanup process comprises, blocking free 3' ends on nucleic acid molecules, which may render them non-extendable by polymerase. In some cases, the probe-linked nucleic acid molecules may be subjected to nucleic acid reactions, such as amplification (e.g., PCR). The amplified products will comprise sequences that are the same or substantially the same as the barcode sequence and sequences of the binding regions of the nucleic acid molecule from which they derive. The amplified products can be traced back to particular nucleic acid molecules and, in some cases, to particular cells. This barcoding method may therefore facilitate rapid analysis of nucleic acid molecules through, for example, sequencing without the need for reverse transcription.

Also provided herein are methods that may involve cell multiplexing. Cells may be processed, partitioned, and labeled. Processed cells may be pooled and nucleic acid molecules from the cells may be further processed. One or more of the processes may involve a nucleic acid reaction, barcoding, partitioning, and/or any combinations or derivatives thereof. One or more of the methods disclosed herein may allow for cell multiplexing without the use of staining reagents and may result in improved occupancy of partitions. One or more of the processes may involve hybridizing a probe to a binding region of a nucleic acid molecule of interest, barcoding the resultant complex, and performing an extension, denaturation, and amplification processes to provide nucleic acid molecules comprising a sequence the same or substantially the same as or complementary to that of the binding region of the nucleic acid molecule of interest.

A multiplexing method may comprise hybridizing a first probe and a second probe to first and second binding regions (e.g., constant upstream and downstream binding regions) of the nucleic acid molecule, linking the first and second probes to provide a probe-linked nucleic acid molecule, and barcoding the probe-linked nucleic acid molecule. One or more processes of the methods provided herein may be performed within a partition such as a droplet or well.

In other cases, a multiplexing method may comprise hybridizing a first probe to a first binding region of a nucleic acid molecule, barcoding the first probe within a first partition with a first barcode sequence, recovering the barcoded first probe from the partition, partitioning the first probe hybridized to the first binding region of the nucleic acid molecule within a second partition, hybridizing a second probe to a second binding region of the nucleic acid molecule within the second partition, and barcoding the first or second probe hybridized to the nucleic acid molecule with a second barcode sequence. In some cases, the first probe may comprise the first barcode sequence and barcoding with a first barcode sequence within the first partition may be simultaneous with hybridizing the first probe to the first binding region. In some cases, the second probe may comprise the second barcode sequence and barcoding with a second barcode sequence may be simultaneous with hybridizing the second probe to the second binding region. In some cases, the first probe may be linked to the second probe (e.g., via a chemical or enzymatic ligation process, as described herein). The first and second probes may be linked to one another within the second partition or outside of the second partition. This process may be repeated for a plurality of nucleic acid molecules (e.g., nucleic acid molecules included within cells, such as fixed cells or cell beads) across a plurality of first partitions and a plurality of second partitions. Each first partition of the plurality of first partitions may comprise a different first barcode sequence of a plurality of first barcode sequences, and each second partition of the plurality of second partitions may comprise a different second barcode sequence of a plurality of second barcode sequences. First barcode sequences may be components of first nucleic acid barcode molecules coupled to a first plurality of beads, while second barcode sequences may be components of second nucleic acid barcode molecules coupled to a second plurality of beads (e.g., as described herein). The plurality of first partitions may be wells, while the second plurality of partitions may be droplets (e.g., as described herein).

In an aspect, a multiplexing method provided herein comprises, (i) fixing a plurality of cells or cell beads, (ii) performing a first partitioning of the plurality of cells or cell beads, (iii) barcoding a plurality of nucleic acid molecules within the plurality of cells or cell beads to provide a plurality of labeled cells or cell beads comprising barcoded nucleic acid molecules, (iv) pooling the plurality of labeled cells or cell beads comprising the barcoded nucleic acid molecules, (v) performing a second partitioning of said plurality of labeled cells or cell beads comprising the barcoded nucleic acid molecules, and (vi) performing a second barcoding of the barcoded nucleic acid molecules to produce multiplexed barcoded nucleic acid molecules.

In some embodiments, the cell or cell bead may be processed to barcode the cell. The cell bead may comprise a cell. In some embodiments, the cell may be alive. In some embodiments, the cell may be fixed using a fixative agent such as paraformaldehyde, formaldehyde, ethanol, methanol, etc. In some cases, the fixed cell may also be permeabilized. In some embodiments, a plurality of cells (e.g., fixed, permeabilized cells) may be partitioned among a plurality of partitions. In some cases, a cell (e.g., a fixed cell) is permeabilized within a partition. Within the plurality of partitions, the plurality of cells (e.g., fixed, permeabilized cells) may be barcoded. In some embodiments, nucleic acid molecules within the plurality of cells (e.g., fixed, permeabilized cells) may be barcoded.

In some cases, the method may comprise providing a sample comprising a nucleic acid molecule (e.g., nucleic acid molecule 2300 shown in FIG. 23) having first and second binding regions; a first probe having a first probe sequence that is complementary to the first binding region and a second probe sequence; and a second probe having a third probe sequence that is complementary to the second binding region. The first and third probe sequences may also comprise first and second reactive moieties, respectively. Upon hybridization of the first probe sequence of the first probe to the first binding region of the nucleic acid molecule, and hybridization of the third probe sequence of the second probe to the second binding region of the nucleic acid molecule, reaction between the adjacent reactive moieties under sufficient conditions may link the first and second probes to yield a probe-linked nucleic acid molecule. The probe-linked nucleic acid molecule may also be referred to as a probe-linked or probe-ligated nucleic acid molecule.

The probe-linked nucleic acid molecule may then be barcoded with a barcode sequence of a nucleic acid barcode molecule to provide a barcoded probe-linked nucleic acid molecule. Barcoding may be achieved by hybridizing a binding sequence of the nucleic acid barcode molecule to the second probe sequence of the first probe of the probe-linked nucleic acid molecule. In some cases, the first probe or the second probe may comprise a barcode sequence. In some cases, both the first probe and the second probe comprise a barcode sequence. In some cases, the first probe and the second probe may be parts of the same probe and may be connected. In some cases, the first probe and the second probe may be parts of a linear probe that forms a circularized nucleic acid product upon hybridization of the first probe and the second probe with the nucleic acid molecule (i.e., analyte). The barcoded nucleic acid molecule may be subjected to amplification reactions to yield an amplified product comprising the first and second binding regions and the barcode sequence or sequences complementary to these sequences. One or more processes may be performed within a partition such as a droplet or well.

In some cases, the method may comprise providing a sample comprising a nucleic acid molecule (e.g., nucleic acid molecule 2300) having first and second binding regions; a first probe having a first probe sequence that is complementary to the first binding region and a second probe sequence; and a second probe having a third probe sequence that is complementary to the second binding region. The first and second binding regions may be adjacent to one another. Alternatively, the first and second binding regions may be separated by a gap region of at least one nucleotide, such as at least 1, 10, 50, 100, or more nucleotides. The first probe sequence of the first probe may hybridize to the first binding region of the nucleic acid molecule, and the third probe sequence of the second probe may hybridize to the second binding region of the nucleic acid molecule to provide a probe-associated nucleic acid molecule. Subsequent to hybridization of the first probe sequence of the first probe to the first binding region of the nucleic acid molecule, and hybridization of the third probe sequence of the second probe to the second binding region of the nucleic acid molecule, the first and second probes may be linked to one another (e.g., via a chemical or enzymatic ligation process, as described herein). For example, the first probe may comprise a first reactive moiety and the second probe may comprise a second reactive moiety, and the first and second reactive moieties may react under sufficient conditions which may link the first and second probes to yield a probe-linked nucleic acid molecule.

The probe-linked nucleic acid molecule may also be referred to as a probe-ligated nucleic acid molecule. The probe-linked nucleic acid molecule may then be barcoded with a barcode sequence of a nucleic acid barcode molecule to provide a barcoded probe-linked nucleic acid molecule. Alternatively, the probe-associated nucleic acid molecule may be barcoded to provide a barcoded probe-associated nucleic acid molecule. Barcoding may be achieved by hybridizing a binding sequence of the nucleic acid barcode molecule to the second probe sequence of the first probe of the probe-linked nucleic acid molecule. In some cases, the first probe or the second probe may comprise a barcode sequence. In some cases, both the first probe and the second probe comprise a barcode sequence. In some cases, the first probe and the second probe may be parts of the same probe and may be connected (e.g., by one or more linking sequences, as described herein). In some cases, the first probe and the second probe may be parts of a linear probe that forms a circularized nucleic acid product upon hybridization of the first probe and the second probe with the nucleic acid molecule. The barcoded nucleic acid molecule may be subjected to amplification reactions to yield an amplified product comprising the first and second binding regions and the barcode sequence or sequences complementary to these sequences. One or more processes may be performed within a partition such as a droplet or well.

In some cases, a second barcoding operation may be performed to generate multiplexed barcoded nucleic acid molecules. The operation may comprise (i) pooling a plurality of cells, wherein a cell of the plurality of cells comprises a barcoded nucleic acid molecule, (ii) partitioning the plurality of cells, and (iii) barcoding the barcoded nucleic acid molecule to produce a multiplexed barcoded nucleic acid molecule. One or more processes may be performed within a partition such as a droplet or well. In some cases, pooling of the cells comprising the barcoded nucleic acid molecule may be performed in a container, such as a vessel or a tube. The pooled cells may then be further partitioned. The partition may comprise conditions sufficient to barcode the barcoded nucleic acid molecule to generate a multiplexed barcoded nucleic acid molecule. In some cases, the conditions comprise a barcode molecule and an enzyme. In some cases, the conditions comprise a barcode molecule, an adapter molecule, and an enzyme. The enzyme may be a ligase, polymerase, or any other suitable enzyme or combinations of enzymes. In one non-limiting example, a cell comprising a barcoded nucleic acid molecule may be partitioned with an adapter molecule comprising a probe-binding sequence and a barcode-binding sequence. In some cases, the partition also comprises a barcode molecule and an enzyme. In some cases, the probe-binding sequence of the adapter molecule may hybridize with a sequence on the barcoded nucleic acid molecule. In some cases, the barcode-binding sequence of the adapter molecule may hybridize with a sequence of the barcode molecule. The barcode molecule may then be adjacent to the barcoded nucleic acid molecule. The barcode molecule may then be ligated (e.g., using an enzyme) to the barcoded nucleic acid molecule, generating a multiplexed barcoded nucleic acid molecule. The multiplexed barcoded nucleic acid molecules may be used to determine cellular occupancy in a partition and may provide a method for improved cellular loading, increased occupancy, determination of multiply-occupied partitions, and may obviate the need for cell staining reagents.

Figures 22A, 22B, 22C, 22D:
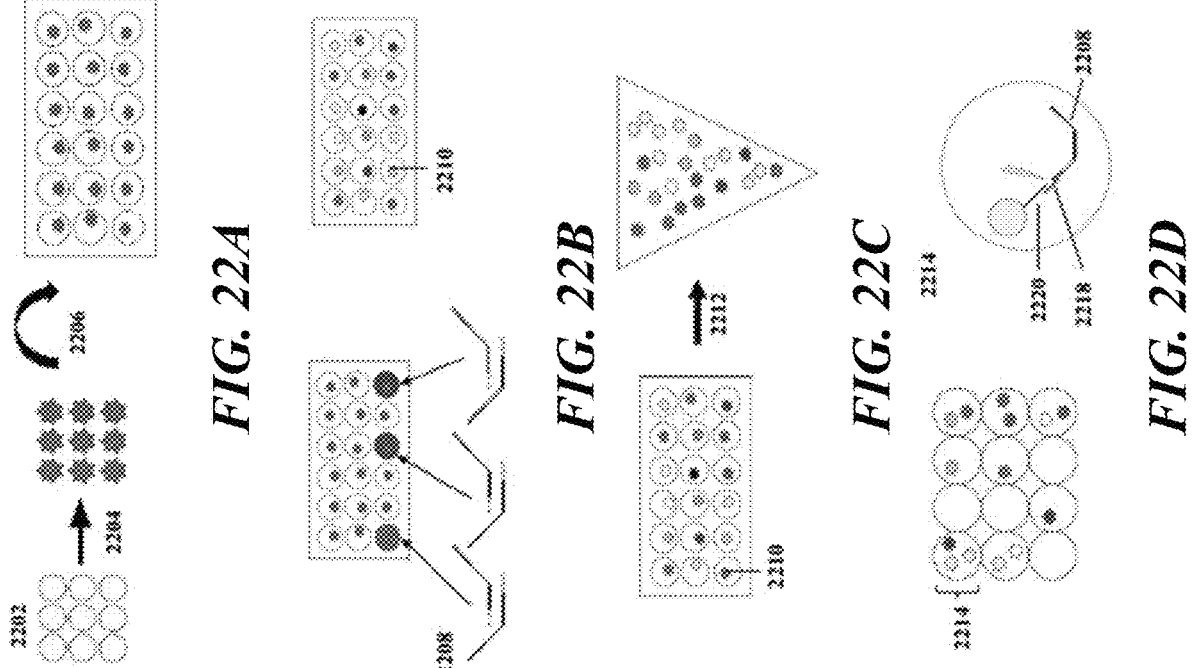
FIGS. 22A-22D illustrates a method for multiplexed barcoding.

FIGS. 22A-22D illustrate an example method for processing nucleic acid molecules in a cell. FIG. 22A illustrates schematically a first partitioning of processed cells. A plurality of cells 2202 may be fixed in process 2204. Alternatively, cells 2202 may not be fixed.

In some cases, process 2204 may comprise introducing plasmid 2400 into the cell and generating (e.g., encoding or expressing) nucleic acid molecule 2300 inside the cell, according to the methods described in further detail elsewhere herein. For example, plasmid 2400 may comprise a guide RNA 2326. An enzyme (e.g., RNA polymerase III) may transcribe the plasmid 2400 and generate nucleic acid molecule 2300 which may comprise the guide RNA 2326. The guide RNA 2326 may comprise a spacer sequence 2318 and a backbone or scaffold 2320. The nucleic acid molecule 2300 may further comprise a promoter sequence 2316. Nucleic acid molecule 2300 may further comprise additional sequences described elsewhere herein. The nucleic acid molecule 2300 may comprise two binding regions (e.g., binding sequences). In some examples, the binding regions (e.g., binding sequences) of nucleic acid molecule 2300 may be two sequences selected from the scaffold 2320', spacer 2318', and promoter 2316'. For example, in a method in which the binding regions are not adjacent to one another, the binding regions may be the scaffold 2320' and the promoter 2316'. In some examples, when using a method in which the binding regions are adjacent to one another, the binding regions may comprise the spacer 2318' and a sequence adjacent to it (e.g., scaffold 2320' or promoter 2316'). Process 2204 may further comprise internalizing one or more probes (e.g., two probes) into the cells, such as by permeabilizing the cells.

In process 2206, the plurality of cells 2202 may be partitioned, e.g., in a multiwell plate. Panel B shows barcoding of the cells. For example, within a partition, the cells may be barcoded using a nucleic acid barcode molecule 2208. In some cases, the cell membrane may be barcoded. In some cases, nucleic acid molecules within the cell may be barcoded. Barcoding may be achieved by hybridizing a barcode nucleic acid molecule 2208 with a nucleic acid molecule in the cell. In some examples, the barcode nucleic acid molecule may comprise a ribonucleic acid molecule. In some cases, the barcode nucleic acid molecule may hybridize with one or more RNA molecules in the cell to generate a barcoded nucleic acid molecule. The cell may then also be considered as a barcoded cell 2210. Each partition may comprise a unique barcode nucleic acid molecule.

FIG. 22C illustrates schematically pooling of barcoded cells. The barcoded cells 2210 may be removed from the partitions and pooled in process 2212. FIG. 22D illustrates schematically a second partitioning, wherein the barcoded cells 2210 are partitioned, e.g., in droplets. The partition 2214 may comprise reagents sufficient for barcoding the barcoded cells. In one example, the partition 2214 may comprise lysis reagents for lysis and release of the barcoded nucleic acid molecules from the barcoded cell 2210, as well as adapter molecules 2218, and barcode molecules 2220. In some cases, the barcode molecules 2220 may be releasably attached to a bead, which may be a gel bead, as described elsewhere herein. The partition 2214 may comprise conditions sufficient to release the barcode molecule 2220 from the bead. In other embodiments, the barcode molecule 2220 may be retained on the bead. In such cases, the bead may subsequently be used for purification, enrichment, and/or collection of the barcode molecules. Within the partition 2214, the adapter molecule 2218 may comprise a probe-binding sequence, which may hybridize with a sequence on the barcoded nucleic acid molecule 2208. The adapter molecule 2218 may also comprise a barcode-binding sequence, which may hybridize with a sequence of the barcode molecule 2220. The barcode molecule 2220 may then be adjacent to the barcoded nucleic acid molecule 2208. The partition 2214 may comprise conditions sufficient to ligate the barcode molecule 2220 to the barcoded nucleic acid molecule 2208, to generate a multiplexed barcoded nucleic acid molecule.

Figures 11A, 11B, 11C, 11D:
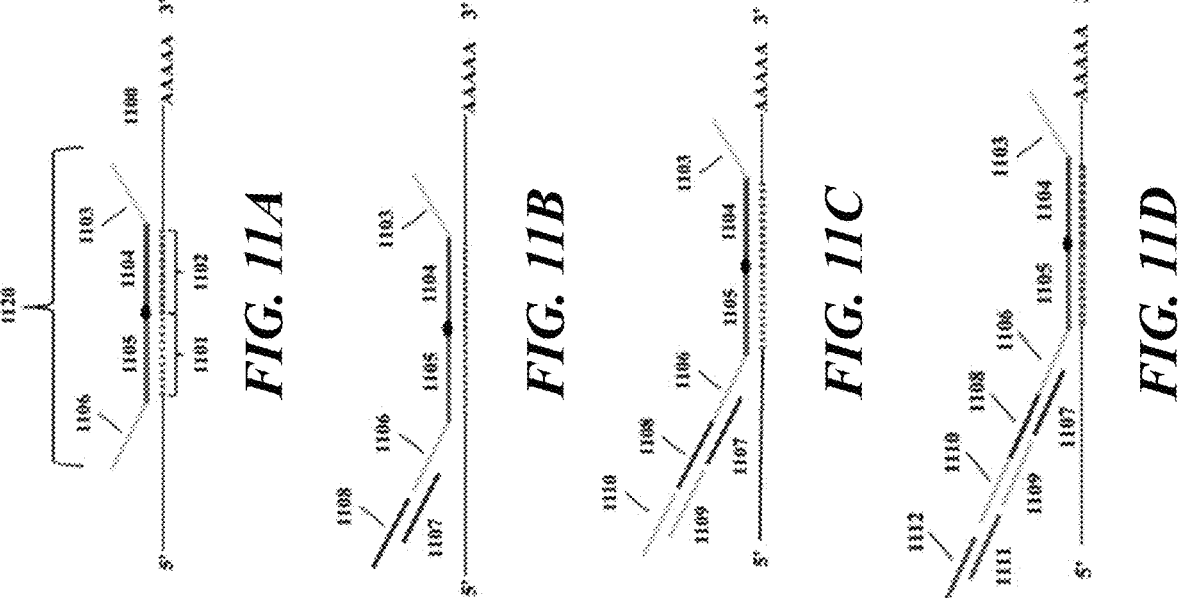
FIGS. 11A-11D illustrate a barcoding scheme using a split-pool approach.

FIGS. 11A-11D show an example of a split-pool barcoding approach which may be used to barcode nucleic acid molecules of the present disclosure. In some examples, a target-specific probe (e.g., the probe-linked molecules described herein) hybridized to a sample nucleic acid molecule (e.g., nucleic acid molecule 2300) may be barcoded through combinatorial assembly of barcode segments using, e.g., a split-pool approach. For example, a plurality of permeabilized cells (or permeabilized nuclei or cell beads) may be contacted with one or more target-specific probes as described herein. FIG. 11A depicts a target-specific probe hybridized to an analyte nucleic acid molecule 1100. In some examples, the analyte nucleic acid molecule may be nucleic acid molecule 2300 described in further detail elsewhere herein. The target-specific probe(s) (e.g., analyte-specific probe) may be configured using any suitable methodology described elsewhere herein (see, e.g., FIGS. 10A-10D, 11A-11D, 12A-12E, 14, 16A-16D, 17A-17C, molecular inversion probes, or other methods and systems). For example, in some instances, a first probe comprising binding sequence 1105 and adapter sequence 1106 and a second probe comprising binding sequence 1103 and adapter sequence 1104 is hybridized to nucleic acid molecule 1100 (e.g., nucleic acid molecule 2300) and the two probes may be linked using, e.g., the enzymatic and/or chemical ligation schemes described elsewhere herein to generate a probe linked nucleic acid molecule 1120.

Binding sequence 1105 may be configured to hybridize to binding region 1101 of nucleic acid molecule 1100 (e.g., nucleic acid molecule 2300) while binding sequence 1104 is configured to hybridize to binding region 1102 of nucleic acid molecule 1100. The binding regions of nucleic acid molecule 2300 are described in detail elsewhere herein. Adapter sequences 1106 and 1103 may each optionally comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences).

Probe-linked nucleic acid molecule 1120 may then be barcoded using a combinatorial assembly of barcode sequence segments (i.e., barcode subunits). For example, in some examples, probe-linked nucleic acid molecule 1120 may be combinatorially barcoded using a split pool approach. In some examples, probe-linked nucleic acid molecule 1120 may be combinatorially barcoded by successive addition of barcode sequence segments. A combinatorial barcode sequence may be synthesized by various methods including, for example, ligation, hybridization, nucleotide polymerization, or a combination thereof.

FIG. 11B shows addition of a first barcode sequence segment to probe-linked nucleic acid molecule 1120. A partially double-stranded nucleic acid barcode molecule 1130 comprising (i) a first strand 1108 comprising a first barcode sequence segment 1131 and an adapter sequence 1132 and (ii) a second strand 1107 comprising a binding sequence 1133 is hybridized to probe-linked nucleic acid molecule 1120. Binding sequence 1133 is complementary to at least a portion of adapter sequence 1106 such that nucleic acid barcode molecule 1130 hybridizes to probe-linked nucleic acid molecule 1120. Sequence 1108 is then attached to probe-linked nucleic acid molecule 1120 (e.g., using ligation and/or nucleic acid extension) to add the first barcode sequence segment 1131.

FIG. 11C shows addition of a second barcode sequence segment to probe-linked nucleic acid molecule 1120 comprising barcode 1108. A partially double-stranded nucleic acid barcode molecule 1140 comprising (i) a first strand 1110 comprising a first barcode sequence segment 1141 and an adapter sequence 1142 and (ii) a second strand 1109 comprising a binding sequence 1143 is hybridized to probe-linked nucleic acid molecule 1120 comprising barcode 1108. Binding sequence 1143 is complementary to at least a portion of adapter sequence 1132 such that nucleic acid barcode molecule 1140 hybridizes to probe-linked nucleic acid molecule 1120 comprising barcode 1108. Sequence 1110 is then attached to probe-linked nucleic acid molecule 1120 comprising barcode 1108 (e.g., using ligation and/or nucleic acid extension) to add the second barcode sequence segment 1141.

FIG. 11D shows addition of a third barcode sequence segment to probe-linked nucleic acid molecule 1120 comprising barcode segments 1108 and 1110. A partially double-stranded nucleic acid barcode molecule 1150 comprising (i) a first strand 1112 comprising a first barcode sequence segment 1151 and an adapter sequence 1152 and (ii) a second strand 1111 comprising a binding sequence 1153 is hybridized to probe-linked nucleic acid molecule 1120 comprising barcode segments 1108 and 1110. Binding sequence 1153 is complementary to at least a portion of adapter sequence 1142 such that nucleic acid barcode molecule 1150 hybridizes to probe-linked nucleic acid molecule 1120 comprising barcode segments 1108 and 1110. Sequence 1112 is then attached to probe-linked nucleic acid molecule 1120 comprising barcode segments 1108 and 1110 (e.g., using ligation and/or nucleic acid extension) to add the third barcode sequence segment 1151.

The combinatorial barcoding scheme described above can be implemented using, e.g., a split-pool approach. For example, a plurality of permeabilized cells (or permeabilized nuclei or cell beads) comprising, e.g., probe-linked nucleic acid molecule 1120 (or any other probe described herein) may be partitioned into a first plurality of partitions (e.g., a plurality of wells) wherein each partition of the plurality of partitions comprises a different (i.e., unique) first barcode sequence segment. After addition of the first barcode sequence segment, cells (or nucleic or cell beads) can be collected from the first plurality of partitioned and pooled and partitioned into a second plurality of partitions (e.g., a plurality of wells) wherein each partition of the plurality of partitions comprises a different (i.e., unique) second barcode sequence segment. Repeating this split-pool process allows the generation of barcodes comprising any suitable amount of barcode sequence segments. Combinatorial barcoding as described herein may comprise at least 1, 2, 3, 4, 5, 6, 7, 8 or more operations (e.g., split-pool cycles). Combinatorial barcoding comprising multiple operations may be useful, for example, in generation of greater barcode diversity and to synthesize a unique barcode sequence on nucleic acid molecules derived from each single cell of a plurality of cells. For example, combinatorial barcoding comprising three operations, each comprising attachment of a unique nucleic acid sequence in each of 96 partitions, will yield up to 884,736 unique barcode combinations. Cells may be partitioned such that at least one cell (or nuclei or cell bead) is present in each partition of a plurality of partitions. Cells may be partitioned such that at least 1; 2; 3; 4; 5; 10; 20; 50; 100; 500; 1,000; 5,000; 10,000; 100,000; 1,000,000; or more cells are present in a single partition. Cells may be partitioned such that at most 1,000,000; 100,000; 10,000; 5,000; 1,000; 500; 100; 50; 20; 10; 5; 4; 3; 2; or 1 cell is present in a single partition. Cells may be partitioned in a random configuration.

In some instances, the methods described herein are performed in a cell bead. See, e.g., U.S. Pat. Pub. 2018/0216162 and PCT Application PCT/US18/54458 for exemplary cell bead generation and processing methods. For example, in some embodiments, a cell bead comprising a cell is generated as described elsewhere herein. In some instances, the cell bead comprises, attached thereto (e.g., covalently attached to the cell bead polymer or cross-linked matrix), a plurality of nucleic acid molecules comprising a poly-T sequence. In some instances, the nucleic acid molecules comprising a poly-T sequence are releasably attached to the c el bead (e.g., via a labile bond as described elsewhere herein). Nucleic acid molecules comprising a poly-T sequence may also comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Cells in the cell bead may then be lysed to release cellular constituents, including mRNA molecules comprising a poly-A tail. Alternatively, cells may be lysed prior to or concurrent with cell bead generation (e.g., in droplets prior to or concurrent with cell bead generation). Poly-A containing mRNA may then be hybridized to the poly-T sequence, thereby immobilizing mRNA in the cell bead. In some instances, captured mRNA is subjected to a reverse transcription reaction to convert captured mRNA into cDNA. In some instances, the cDNA is single stranded. In other instances, the cDNA is double stranded. Nucleic acid molecules immobilized in cell beads, can then be contacted by the probe molecules described herein and processed to detect cellular nucleic acid molecules (such as a nucleic acid molecule comprising a CRISPR guide, e.g., nucleic acid molecule 2300) as described herein.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more beads. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The methods and systems of the present disclosure may comprise methods and systems for generating one or more partitions such as droplets. The droplets may comprise a plurality of droplets in an emulsion. In some examples, the droplets may comprise droplets in a colloid. In some cases, the emulsion may comprise a microemulsion or a nanoemulsion. In some examples, the droplets may be generated with aid of a microfluidic device and/or by subjecting a mixture of immiscible phases to agitation (e.g., in a container). In some cases, a combination of the mentioned methods may be used for droplet and/or emulsion formation.

Droplets can be formed by creating an emulsion by mixing and/or agitating immiscible phases. Mixing or agitation may comprise various agitation techniques, such as vortexing, pipetting, tube flicking, or other agitation techniques. In some cases, mixing or agitation may be performed without using a microfluidic device. In some examples, the droplets may be formed by exposing a mixture to ultrasound or sonication. Systems and methods for droplet and/or emulsion generation by agitation are described in International Application No. PCT/US20/17785, which is entirely incorporated herein by reference for all purposes.

Microfluidic devices or platforms comprising microfluidic channel networks (e.g., on a chip) can be utilized to generate partitions such as droplets and/or emulsions as described herein. Methods and systems for generating partitions such as droplets, methods of encapsulating biological particle methods of increasing the throughput of droplet generation, and various geometries, architectures, and configurations of microfluidic devices and channels are described in U.S. Patent Publication Nos. 2019/0367997 and 2019/0064173, each of which is entirely incorporated herein by reference for all purposes.

In some examples, individual particles can be partitioned to discrete partitions by introducing a flowing stream of particles in an aqueous fluid into a flowing stream or reservoir of a non-aqueous fluid, such that droplets may be generated at the junction of the two streams/reservoir, such as at the junction of a microfluidic device provided elsewhere herein.

The methods of the present disclosure may comprise generating partitions and/or encapsulating particles, such as analyte carriers or analyte carriers, in some cases, individual analyte carriers such as single cells. In some examples, reagents may be encapsulated and/or partitioned (e.g., co-partitioned with analyte carriers) in the partitions. Various mechanisms may be employed in the partitioning of individual particles. An example may comprise porous membranes through which aqueous mixtures of cells may be extruded into fluids (e.g., non-aqueous fluids).

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
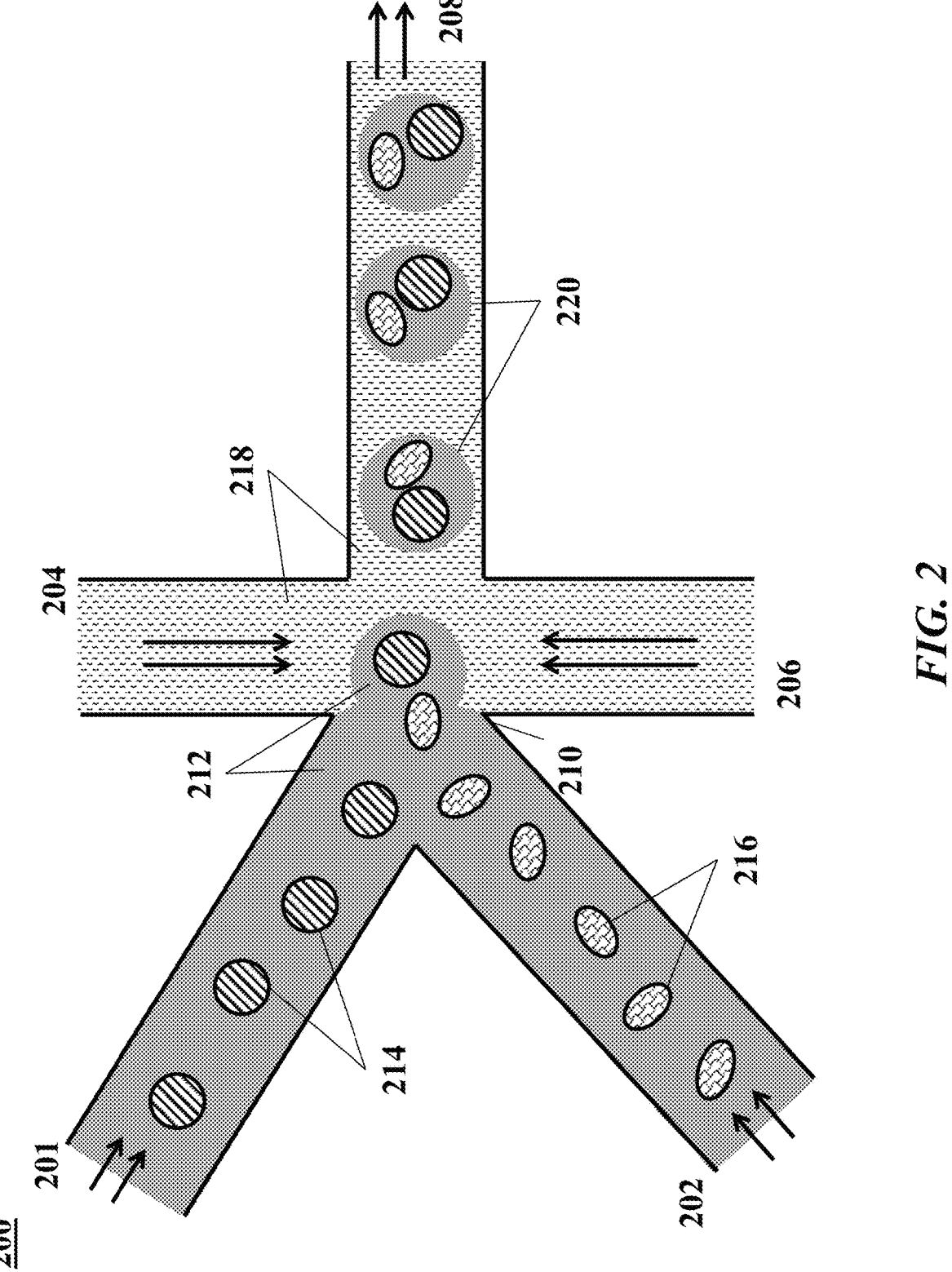
FIG. 2 shows an example of a microfluidic channel structure for delivering barcode carrying beads to droplets

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., Ca$^{2+}$ ions), can be used as an encapsulation process using the described processes. Likewise, agarose droplets may also be transformed into capsules through temperature-based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead."

A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example, after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles. Cell beads may be or include a cell, cell derivative, cellular material and/or material derived from the cell in, within, or encased in a matrix, such as a polymeric matrix. In some cases, a cell bead may comprise a live cell. In some instances, the live cell may be capable of being cultured when enclosed in a gel or polymer matrix, or of being cultured when comprising a gel or polymer matrix. In some instances, the polymer or gel may be diffusively permeable to certain components and diffusively impermeable to other components (e.g., macromolecular constituents).

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In some instances, a droplet is formed by creating an emulsion by mixing or agitating immiscible phases. Mixing or agitation may comprise various agitation techniques, such as vortexing, pipetting, tube flicking, or other agitation techniques. In some cases, mixing or agitation may be performed without using a microfluidic device. In some examples, a droplet may be formed by exposing a mixture to ultrasound or sonication. For example, to partition contents into droplets, a mixture comprising a first fluid, a second fluid, optionally a surfactant, and the contents can be subject to such agitation techniques to generate a plurality of droplets (first fluid-in-second fluid or second fluid-in-first fluid) comprising the contents, or subsets thereof. In an example, a mixture comprises beads. Upon agitation, the beads in the mixture may limit droplet break-up into droplets smaller than the size of the beads, and a substantially monodisperse population of droplets comprising the beads may result.

In the case of droplets in an emulsion, allocating individual particles to discrete partitions may in one non-limiting example be accomplished by introducing a flowing stream of particles in an aqueous fluid into a flowing stream or reservoir of a non-aqueous fluid, such that droplets are generated at the junction of the two streams (see generally, e.g., FIGS. 1-7B). Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature-based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylamide, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead."

A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example, after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles. Cell beads may be or include a cell, cell derivative, cellular material and/or material derived from the cell in, within, or encased in a matrix, such as a polymeric matrix. In some cases, a cell bead may comprise a live cell. In some instances, the live cell may be capable of being cultured when enclosed in a gel or polymer matrix, or of being cultured when comprising a gel or polymer matrix. In some instances, the polymer or gel may be diffusively permeable to certain components and diffusively impermeable to other components (e.g., macromolecular constituents).

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli (or reagents). In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Wells

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In some instances, the wells or microwells may be configured to toggle between "open" and "closed" configurations. For instance, an "open" microwell or set of microwells may be "closed" or "sealed" using a membrane (e.g., semi-permeable membrane), an oil (e.g., fluorinated oil to cover an aqueous solution), or a lid, as described elsewhere herein.

The well may have a volume of less than 1 milliliter (mL). For instance, the well may be configured to hold a volume of at most 1000 microliters (µL), at most 100 µL, at most 10 µL, at most 1 µL, at most 100 nanoliters (nL), at most 10 nL, at most 1 nL, at most 100 picoliters (pL), at most 10 (pL), or less. The well may be configured to hold a volume of about 1000 µL, about 100 µL, about 10 µL, about 1 µL, about 100 nL, about 10 nL, about 1 nL, about 100 pL, about 10 pL, etc. The well may be configured to hold a volume of at least 10 pL, at least 100 pL, at least 1 nL, at least 10 nL, at least 100 nL, at least 1 µL, at least 10 µL, at least 100 µL, at least 1000 µL, or more. The well may be configured to hold a volume in a range of volumes listed herein, for example, from about 5 nL to about 20 nL, from about 1 nL to about 100 nL, from about 500 pL to about 100 pL, etc. The well may be of a plurality of wells that have varying volumes and may be configured to hold a volume appropriate to accommodate any of the partition volumes described herein.

In some instances, a microwell array or plate comprises a single variety of microwells. In some instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a microcapsule, droplet, bead, or other reagent. In some cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a microcapsule or bead that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the microcapsule or bead, after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

A well may comprise free reagents and/or reagents encapsulated in, or otherwise coupled to or associated with, microcapsules, beads, or droplets. Any of the reagents described in this disclosure may be encapsulated in, or otherwise coupled to, a microcapsule, droplet, or bead, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds. As described herein, one or more reagents in the well may be used to perform one or more reactions, including but not limited to: cell lysis, cell fixation, permeabilization, nucleic acid reactions, e.g., nucleic acid extension reactions, amplification, reverse transcription, transposase reactions (e.g., tagmentation), etc.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In some cases, a well comprises a microcapsule, bead, or droplet that comprises a set of reagents that has a similar attribute (e.g., a set of enzymes, a set of minerals, a set of oligonucleotides, a mixture of different barcode molecules, a mixture of identical barcode molecules). In other cases, a microcapsule, bead, or droplet comprises a heterogeneous mixture of reagents. In some cases, the heterogeneous mixture of reagents can comprise all components necessary to perform a reaction. In some cases, such mixture can comprise all components necessary to perform a reaction, except for 1, 2, 3, 4, 5, or more components necessary to perform a reaction. In some cases, such additional components are contained within, or otherwise coupled to, a different microcapsule, droplet, or bead, or within a solution within a partition (e.g., microwell) of the system.

Figure 28:
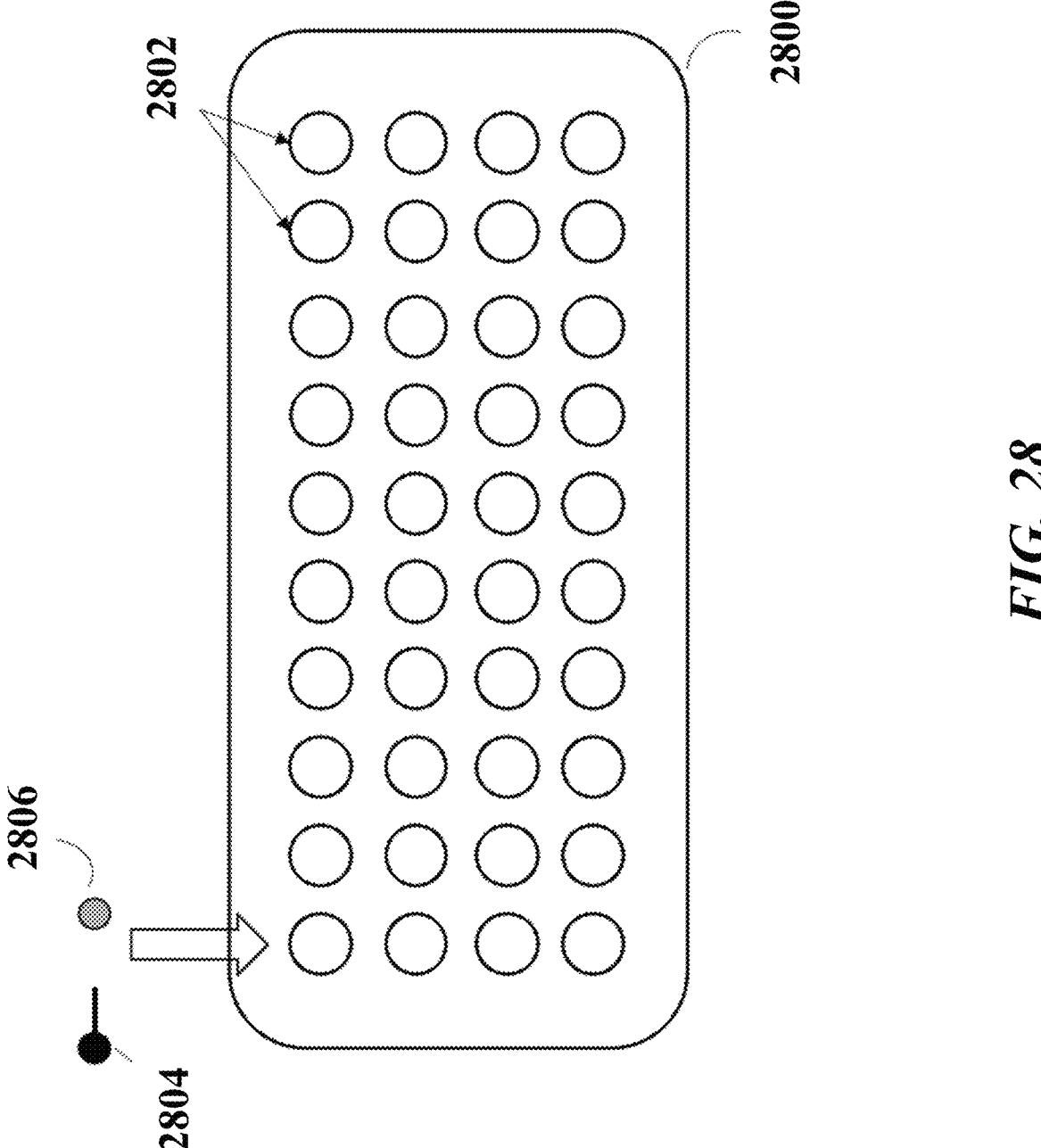
FIG. 28 schematically illustrates an example microwell array.

FIG. 28 schematically illustrates an example of a microwell array. The array can be contained within a substrate 2800. The substrate 2800 comprises a plurality of wells 2802. The wells 2802 may be of any size or shape, and the spacing between the wells, the number of wells per substrate, as well as the density of the wells on the substrate 2800 can be modified, depending on the particular application. In one such example application, a sample molecule 2806, which may comprise a cell or cellular components (e.g., nucleic acid molecules) is co-partitioned with a bead 2804, which may comprise a nucleic acid barcode molecule coupled thereto. The wells 2802 may be loaded using gravity or other loading technique (e.g., centrifugation, liquid handler, acoustic loading, optoelectronic, etc.). In some instances, at least one of the wells 2802 contains a single sample molecule 2806 (e.g., cell) and a single bead 2804.

Reagents may be loaded into a well either sequentially or concurrently. In some cases, reagents are introduced to the device either before or after a particular operation. In some cases, reagents (which may be provided, in certain instances, in microcapsules, droplets, or beads) are introduced sequentially such that different reactions or operations occur at different steps. The reagents (or microcapsules, droplets, or beads) may also be loaded at operations interspersed with a reaction or operation step. For example, microcapsules (or droplets or beads) comprising reagents for fragmenting polynucleotides (e.g., restriction enzymes) and/or other enzymes (e.g., transposases, ligases, polymerases, etc.) may be loaded into the well or plurality of wells, followed by loading of microcapsules, droplets, or beads comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a microcapsule, bead, or droplet. These microcapsules, beads, or droplets may be loaded into a partition (e.g., a microwell) before, after, or concurrently with the loading of a cell, such that each cell is contacted with a different microcapsule, bead, or droplet. This technique may be used to attach a unique nucleic acid barcode molecule to nucleic acid molecules obtained from each cell. Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in some instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet or microcapsule may be partitioned into a well. The droplets may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In some instances, imaging may be used to characterize live cells in the wells, including, but not limited to: dynamic live-cell tracking, cell-cell interactions (when two or more cells are co-partitioned), cell proliferation, etc. Alternatively or in addition to, imaging may be used to characterize a quantity of amplification products in the well.

In operation, a well may be loaded with a sample and reagents, simultaneously or sequentially. When cells or cell beads are loaded, the well may be subjected to washing, e.g., to remove excess cells from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 29:
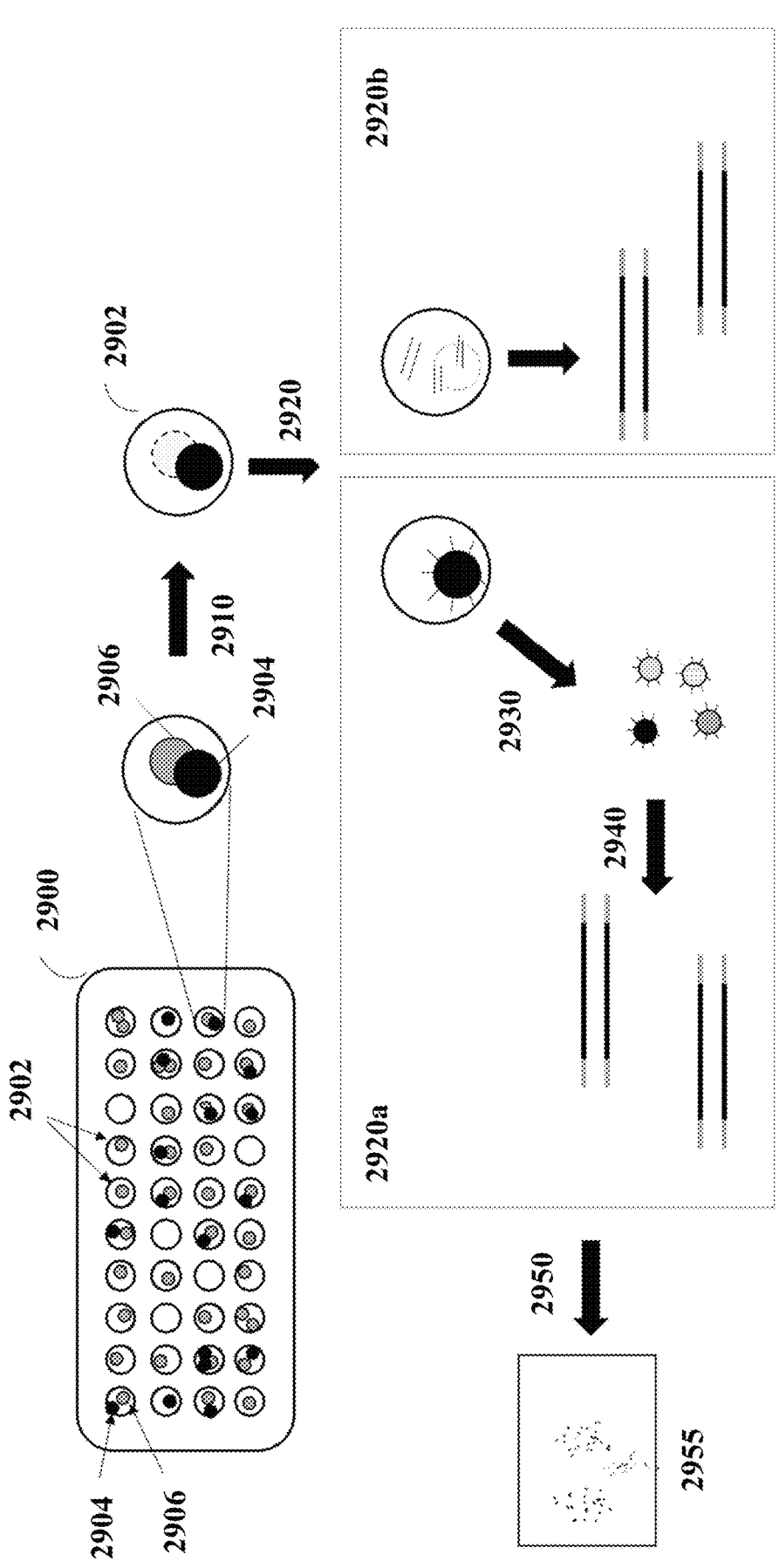
FIG. 29 schematically illustrates an example workflow for processing nucleic acid molecules.

FIG. 29 schematically shows an example workflow for processing nucleic acid molecules within a sample. A substrate 2900 comprising a plurality of microwells 2902 may be provided. A sample 2906 which may comprise a cell, cell bead, cellular components or analytes (e.g., proteins and/or nucleic acid molecules) can be co-partitioned, in a plurality of microwells 2902, with a plurality of beads 2904 comprising nucleic acid barcode molecules. During process 2910, the sample 2906 may be processed within the partition. For instance, in the case of live cells, the cell may be subjected to conditions sufficient to lyse the cells and release the analytes contained therein. In process 2920, the bead 2904 may be further processed. By way of example, processes 2920a and 2920b schematically illustrate different workflows, depending on the properties of the bead 2904.

In 2920a, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 2930, the beads 2904 from multiple wells 2902 may be collected and pooled. Further processing may be performed in process 2940. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 2950, further characterization, such as sequencing may be performed to generate sequencing reads. The sequencing reads may yield information on individual cells or populations of cells, which may be represented visually or graphically, e.g., in a plot 2955.

In 2920b, the bead comprises nucleic acid barcode molecules that are releasably attached thereto, as described below. The bead may degrade or otherwise release the nucleic acid barcode molecules into the well 2902; the nucleic acid barcode molecules may then be used to barcode nucleic acid molecules within the well 2902. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 2950, further characterization, such as sequencing may be performed to generate sequencing reads. The sequencing reads may yield information on individual cells or populations of cells, which may be represented visually or graphically, e.g., in a plot 2955.

Nucleic acid barcode molecules may be delivered to a partition (e.g., a droplet or well) via a solid support or carrier (e.g., a bead). In some cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

A nucleic acid barcode molecule may contain a barcode sequence and a functional sequence, such as a nucleic acid primer sequence or a template switch oligonucleotide (TSO) sequence.

The solid support may be a bead. A solid support, e.g., a bead, may be porous, non-porous, hollow (e.g., a microcapsule), solid, semi-solid, and/or a combination thereof. Beads may be solid, semi-solid, semi-fluidic, fluidic, and/or a combination thereof. In some instances, a solid support, e.g., a bead, may be dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support, e.g., the bead, may be a silica bead. In some cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

In some examples, beads, biological particles, analyte carriers, and droplets may flow along channels (e.g., the channels of a microfluidic device), in some cases at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (µm), 5 µm, 10 µm, 20 µm, 30 µm, 40 µm, 50 µm, 60 µm, 70 µm, 80 µm, 90 µm, 100 µm, 250 µm, 500 µm, 1 mm, or greater. In some cases, a bead may have a diameter of less than about 10 nm, 100 nm, 500 nm, 1 µm, 5 µm, 10 µm, 20 µm, 30 µm, 40 µm, 50 µm, 60 µm, 70 µm, 80 µm, 90 µm, 100 µm, 250 µm, 500 µm, 1 mm, or less. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using pre-polymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide) that comprises one or more functional sequences, such as a TSO sequence or a primer sequence (e.g., a poly T sequence, or a nucleic acid primer sequence complementary to a nucleic acid sequence and/or for amplifying a nucleic acid sequence, a random primer, or a primer sequence for messenger RNA) that is useful for incorporation into the bead, etc.) and/or one or more barcode sequences. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence (or a portion thereof) for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence (or a portion thereof) for attachment to a sequencing flow cell for Illumina sequencing. In some cases, the nucleic acid molecule can comprise a barcode sequence. In some cases, the nucleic acid molecule can further comprise a unique molecular identifier (UMI). In some cases, the nucleic acid molecule can comprise an R1 primer sequence for Illumina sequencing. In some cases, the nucleic acid molecule can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

In some cases, the nucleic acid molecule can comprise one or more functional sequences. For example, a functional sequence can comprise a sequence for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the functional sequence can comprise a barcode sequence or multiple barcode sequences. In some cases, the functional sequence can comprise a unique molecular identifier (UMI). In some cases, the functional sequence can comprise a primer sequence (e.g., an R1 primer sequence for Illumina sequencing, an R2 primer sequence for Illumina sequencing, etc.). In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof.

Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
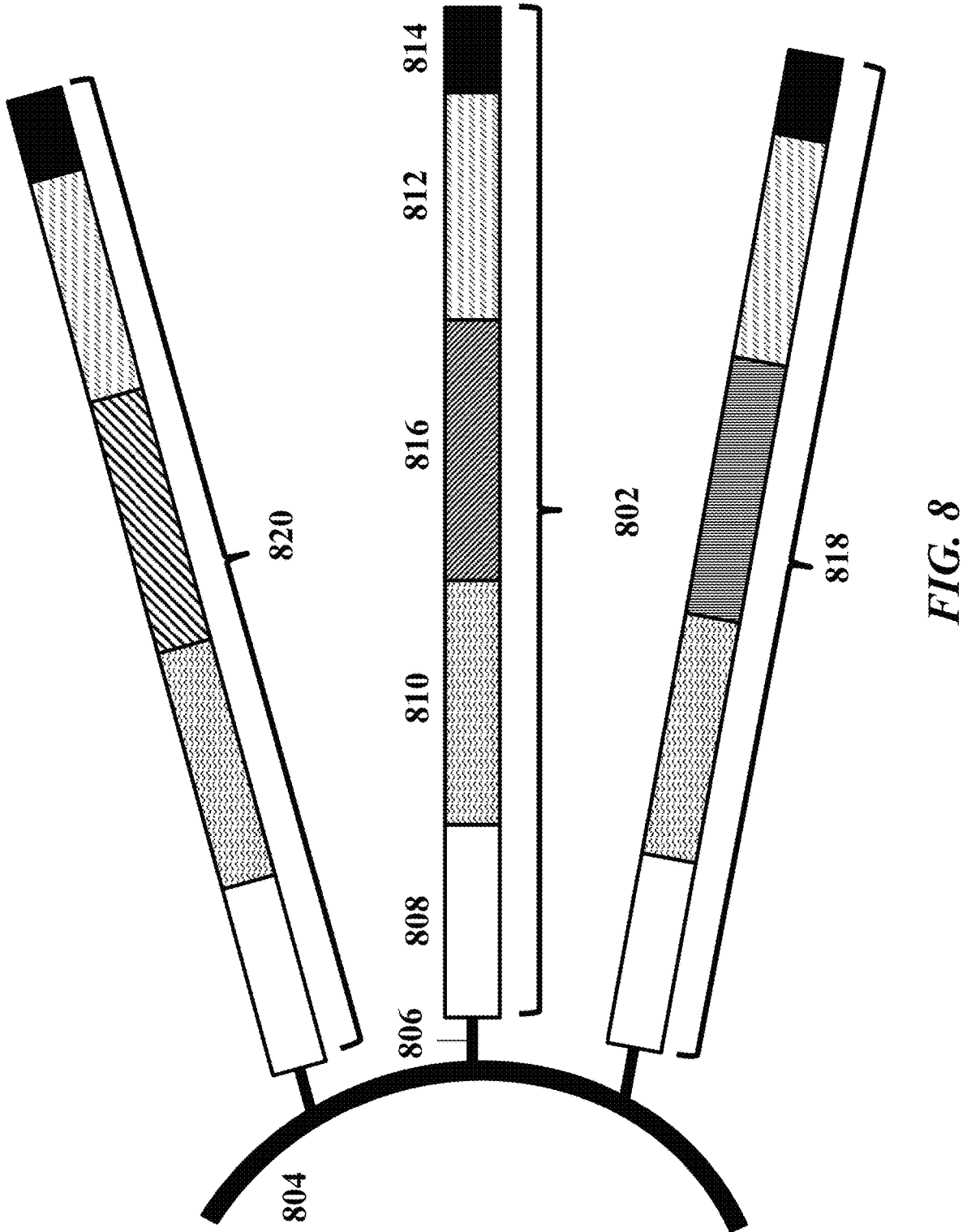
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems), or partial sequence(s) thereof. The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where the nucleic acid molecules from the sample remain attached to the bead, the beads from various partitions may be collected, pooled, and subjected to further processing (e.g., reverse transcription, adapter attachment, amplification, clean up, sequencing). In other instances, the processing may occur in the partition. For example, conditions sufficient for barcoding, adapter attachment, reverse transcription, or other nucleic acid processing operations may be provided in the partition and performed prior to clean up and sequencing.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, a biological particle (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In some instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 9:
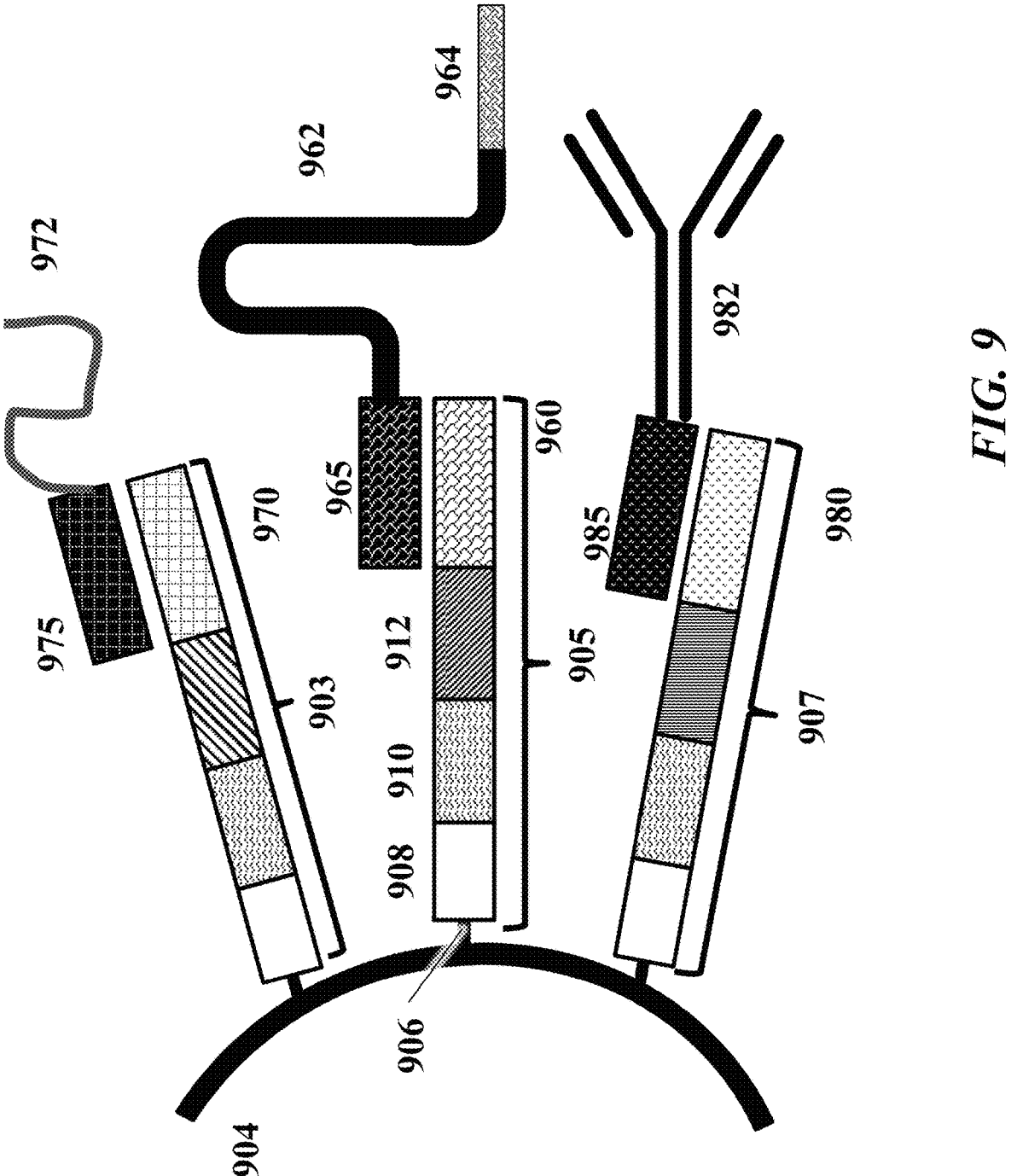
FIG. 9 illustrates another example of a barcode carrying bead.

FIG. 9 illustrates another example of a barcode carrying bead. A nucleic acid molecule 905, such as an oligonucleotide, can be coupled to a bead 904 by a releasable linkage 906, such as, for example, a disulfide linker. The nucleic acid molecule 905 may comprise a first capture sequence 960. The same bead 904 may be coupled (e.g., via releasable linkage) to one or more other nucleic acid molecules 903, 907 comprising other capture sequences. The nucleic acid molecule 905 may be or comprise a barcode. As noted elsewhere herein, the structure of the barcode may comprise a number of sequence elements, such as a functional sequence 908 (e.g., flow cell attachment sequence, sequencing primer sequence, etc.), a barcode sequence 910 (e.g., bead-specific sequence common to bead, partition-specific sequence common to partition, etc.), and a unique molecular identifier 912 (e.g., unique sequence within different molecules attached to the bead), or partial sequences thereof. The capture sequence 960 may be configured to attach to a corresponding capture sequence 965. In some instances, the corresponding capture sequence 965 may be coupled to another molecule that may be an analyte or an intermediary carrier. For example, as illustrated in FIG. 9, the corresponding capture sequence 965 is coupled to a guide RNA molecule 962 comprising a target sequence 964, wherein the target sequence 964 is configured to attach to the analyte. Another oligonucleotide molecule 907 attached to the bead 904 comprises a second capture sequence 980 which is configured to attach to a second corresponding capture sequence 985. As illustrated in FIG. 9, the second corresponding capture sequence 985 is coupled to an antibody 982. In some cases, the antibody 982 may have binding specificity to an analyte (e.g., surface protein). Alternatively, the antibody 982 may not have binding specificity. Another oligonucleotide molecule 903 attached to the bead 904 comprises a third capture sequence 970 which is configured to attach to a second corresponding capture sequence 975. As illustrated in FIG. 9, the third corresponding capture sequence 975 is coupled to a molecule 972. The molecule 972 may or may not be configured to target an analyte. The other oligonucleotide molecules 903, 907 may comprise the other sequences (e.g., functional sequence, barcode sequence, UMI, etc.) described with respect to oligonucleotide molecule 905. While a single oligonucleotide molecule comprising each capture sequence is illustrated in FIG. 9, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 904 may comprise other capture sequences. Alternatively or in addition, the bead 904 may comprise fewer types of capture sequences (e.g., two capture sequences). Alternatively or in addition, the bead 904 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be function-alized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degra-dation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligo-nucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate cer-tain reactions for generating a sequencing library, e.g., amplification, within the partition. In some cases, the pre-defined concentration of the primer can be limited by the process of producing nucleic acid molecule (e.g., oligo-nucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accom-plished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidi-cally. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization-based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In some cases, a species (e.g., oligonucleotide molecules comprising barcodes) that are attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include P-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), P-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

In some examples, a partition of the plurality of partitions may comprise a single biological particle or analyte carrier (e.g., a single cell or a single nucleus of a cell). In some examples, a partition of the plurality of partitions may comprise multiple biological particles or analyte carriers. Such partitions may be referred to as multiply occupied partitions, and may comprise, for example, two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet-based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000, 000,000 partitions, or more partitions can be generated or otherwise provided. Moreover, the plurality of partitions may comprise both unoccupied partitions (e.g., empty partitions) and occupied partitions.

Flow Sorting

A sample may derive from any useful source including any subject, such as a human subject. A sample may comprise material (e.g., one or more analyte carriers) from one or more different sources, such as one or more different subjects. Multiple samples, such as multiple samples from a single subject (e.g., multiple samples obtained in the same or different manners from the same or different bodily locations, and/or obtained at the same or different times (e.g., seconds, minutes, hours, days, weeks, months, or years apparat)), or multiple samples from different subjects, may be obtained for analysis as described herein. For example, a first sample may be obtained from a subject at a first time and a second sample may be obtained from the subject at a second time later than the first time. The first time may be before a subject undergoes a treatment regimen or procedure (e.g., to address a disease or condition), and the second time may be during or after the subject undergoes the treatment regimen or procedure. In another example, a first sample may be obtained from a first bodily location or system of a subject (e.g., using a first collection technique) and a second sample may be obtained from a second bodily location or system of the subject (e.g., using a second collection technique), which second bodily location or system may be different than the first bodily location or system. In another example, multiple samples may be obtained from a subject at a same time from the same or different bodily locations. Different samples, such as different subjects collected from different bodily locations of a same subject, at different times, from multiple different subjects, and/or using different collection techniques, may undergo the same or different processing (e.g., as described herein). For example, a first sample may undergo a first processing protocol and a second sample may undergo a second processing protocol.

A sample may be a biological sample, such as a cell sample (e.g., as described herein). A sample may include one or more analyte carriers, such as one or more cells and/or cellular constituents, such as one or more cell nuclei. For example, a sample may comprise a plurality of analyte carriers, such as a plurality of cells and/or cellular constituents. Analyte carriers (e.g., cells or cellular constituents, such as cell nuclei) of a sample may be of a single type or a plurality of different types. For example, cells of a sample may include one or more different types or blood cells.

Cells and cellular constituents of a sample may be of any type. For example, a cell or cellular constituent may be a mammalian, fungal, plant, bacterial, or other cell type. In some cases, the cell is a mammalian cell, such as a human cell. The cell may be, for example, a stem cell, liver cell, nerve cell, bone cell, blood cell, reproductive cell, skin cell, skeletal muscle cell, cardiac muscle cell, smooth muscle cell, hair cell, hormone-secreting cell, or glandular cell. The cell may be, for example, an erythrocyte (e.g., red blood cell), a megakaryocyte (e.g., platelet precursor), a monocyte (e.g., white blood cell), a leukocyte, a B cell, a T cell (such as a helper, suppressor, cytotoxic, or natural killer T cell), an osteoclast, a dendritic cell, a connective tissue macrophage, an epidermal Langerhans cell, a microglial cell, a granulocyte, a hybridoma cell, a mast cell, a natural killer cell, a reticulocyte, a hematopoietic stem cell, a myoepithelial cell, a myeloid-derived suppressor cell, a platelet, a thymocyte, a satellite cell, an epithelial cell, an endothelial cell, an epididymal cell, a kidney cell, a liver cell, an adipocyte, a lipocyte, or a neuron cell. In some cases, the cell may be associated with a cancer, tumor, or neoplasm. In some cases, the cell may be associated with a fetus. In some cases, the cell may be a Jurkat cell.

A cell of a biological sample may have any feature or dimension. For example, a cell may have a first dimension, a second dimension, and a third dimension, where the first, second, and third dimensions are approximately the same. In other cases, the first and second dimensions may be approximately the same, and the third dimension may be different, or the first, second, and third dimensions may all be different. In some cases, a cell may comprise a dimension (e.g., a diameter) of at least about 1 μm. For example, a cell may comprise a dimension of at least about 1 micrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some cases, the cell may comprise a dimension of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, a cell may comprise a dimension of between about 1 μm and 100 μm. Any or all dimensions of a cell may be variable. For example, the dimensions of a substantially fluid cell may vary over a rapid timescale. Dimensions of a more rigid cell may be fixed or may vary with lesser amplitude. Accordingly, the dimensions provided herein may represent averages rather than fixed values. The volume of a cell may be at least about 1 $\mu m^3$. In some cases, the volume of a cell may be at least about 10 $\mu m^3$. For example, the volume of the cell may be at least 1 $\mu m^3$, 2 $\mu m^3$, 3 $\mu m^3$, 4 $\mu m^3$, 5 $\mu m^3$, 6 $\mu m^3$, 7 $\mu m^3$, 8 $\mu m^3$, 9 $\mu m^3$, 10 $\mu m^3$, 12 $\mu m^3$, 14 $\mu m^3$, 16 $\mu m^3$, 18 $\mu m^3$, 20 $\mu m^3$, 25 $\mu m^3$, 30 $\mu m^3$, 35 $\mu m^3$, 40 $\mu m^3$, 45 $\mu m^3$, 50 $\mu m^3$, 55 $\mu m^3$, 60 $\mu m^3$, 65 $\mu m^3$, 70 $\mu m^3$, 75 $\mu m^3$, 80 $\mu m^3$, 85 $\mu m^3$, 90 $\mu m^3$, 95 $\mu m^3$, 100 $\mu m^3$, 125 $\mu m^3$, 150 $\mu m^3$, 175 $\mu m^3$, 200 $\mu m^3$, 250 $\mu m^3$, 300 $\mu m^3$, 350 $\mu m^3$, 400 $\mu m^3$, 450 $\mu m^3$, $\mu m^3$, 500 $\mu m^3$, 550 $\mu m^3$, 600 $\mu m^3$, 650 $\mu m^3$, 700 $\mu m^3$, 750 $\mu m^3$, 800 $\mu m^3$, 850 $\mu m^3$, 900 $\mu m^3$, 950 $\mu m^3$, 1000 $\mu m^3$, 1200 $\mu m^3$, 1400 $\mu m^3$, 1600 $\mu m^3$, 1800 $\mu m^3$, 2000 $\mu m^3$, 2200 $\mu m^3$, 2400 $\mu m^3$, 2600 $\mu m^3$, 2800 $\mu m^3$, 3000 $\mu m^3$, or greater. In some cases, a cell may comprise a volume of between about 1 $\mu m^3$ and 100 $\mu m^3$, such as between about 1 $\mu m^3$ and 10 $\mu m^3$, between about 10 $\mu m^3$ and 50 $\mu m^3$, or between about 50 $\mu m^3$ and 100 $\mu m^3$. In some cases, a cell may comprise a volume of between about 100 $\mu m^3$ and 1000 $\mu m^3$, such as between about 100 $\mu m^3$ and 500 $\mu m^3$ or between about 500 $\mu m^3$ and 1000 $\mu m^3$. In some cases, a cell may comprise a volume between about 1000 $\mu m^3$ and 3000 $\mu m^3$, such as between about 1000 $\mu m^3$ and 2000 $\mu m^3$ or between about 2000 $\mu m^3$ and 3000 $\mu m^3$. In some cases, a cell may comprise a volume between about 1 $\mu m^3$ and 3000 $\mu m^3$, such as between about 1 $\mu m^3$ and 2000 $\mu m^3$, between about 1 $\mu m^3$ and 1000 $\mu m^3$, between about 1 $\mu m^3$ and 500 $\mu m^3$, or between about 1 $\mu m^3$ and 250 $\mu m^3$.

A cell of a biological sample may comprise one or more cross-sections that may be the same or different. In some cases, a cell may have a first cross-section that is different from a second cross-section. a cell may have a first cross-section that is at least about 1 $\mu m$. For example, a cell may comprise a cross-section (e.g., a first cross-section) of at least about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 11 $\mu m$, 12 $\mu m$, 13 $\mu m$, 14 $\mu m$, 15 $\mu m$, 16 $\mu m$, 17 $\mu m$, 18 $\mu m$, 19 $\mu m$, 20 $\mu m$, 25 $\mu m$, 30 $\mu m$, 35 $\mu m$, 40 $\mu m$, 45 $\mu m$, 50 $\mu m$, 55 $\mu m$, 60 $\mu m$, 65 $\mu m$, 70 $\mu m$, 75 $\mu m$, 80 $\mu m$, 85 $\mu m$, 90 $\mu m$, 100 $\mu m$, 120 $\mu m$, 140 $\mu m$, 160 $\mu m$, 180 $\mu m$, 200 $\mu m$, 250 $\mu m$, 300 $\mu m$, 350 $\mu m$, 400 $\mu m$, 450 $\mu m$, 500 $\mu m$, 550 $\mu m$, 600 $\mu m$, 650 $\mu m$, 700 $\mu m$, 750 $\mu m$, 800 $\mu m$, 850 $\mu m$, 900 $\mu m$, 950 $\mu m$, 1 millimeter (mm), or greater. In some cases, a cell may comprise a cross-section (e.g., a first cross-section) of between about 1 $\mu m$ and 500 $\mu m$, such as between about 1 $\mu m$ and 100 $\mu m$, between about 100 $\mu m$ and 200 $\mu m$, between about 200 $\mu m$ and 300 $\mu m$, between about 300 $\mu m$ and 400 $\mu m$, or between about 400 $\mu m$ and 500 $\mu m$. For example, a cell may comprise a cross-section (e.g., a first cross-section) of between about 1 $\mu m$ and 100 $\mu m$. In some cases, the cell may have a second cross-section that is at least about 1 $\mu m$. For example, the cell may comprise a second cross-section of at least about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 11 $\mu m$, 12 $\mu m$, 13 $\mu m$, 14 $\mu m$, 15 $\mu m$, 16 $\mu m$, 17 $\mu m$, 18 $\mu m$, 19 $\mu m$, 20 $\mu m$, 25 $\mu m$, 30 $\mu m$, 35 $\mu m$, 40 $\mu m$, 45 $\mu m$, 50 $\mu m$, 55 $\mu m$, 60 $\mu m$, 65 $\mu m$, 70 $\mu m$, 75 $\mu m$, 80 $\mu m$, 85 $\mu m$, 90 $\mu m$, 100 $\mu m$, 120 $\mu m$, 140 $\mu m$, 160 $\mu m$, 180 $\mu m$, 200 $\mu m$, 250 $\mu m$, 300 $\mu m$, 350 $\mu m$, 400 $\mu m$, 450 $\mu m$, 500 $\mu m$, 550 $\mu m$, 600 $\mu m$, 650 $\mu m$, 700 $\mu m$, 750 $\mu m$, 800 $\mu m$, 850 $\mu m$, 900 $\mu m$, 950 $\mu m$, 1 millimeter (mm), or greater. In some cases, a cell may comprise a second cross-section of between about 1 $\mu m$ and 500 $\mu m$, such as between about 1 $\mu m$ and 100 $\mu m$, between about 100 $\mu m$ and 200 $\mu m$, between about 200 $\mu m$ and 300 $\mu m$, between about 300 $\mu m$ and 400 $\mu m$, or between about 400 $\mu m$ and 500 $\mu m$. For example, a cell may comprise a second cross-section of between about 1 $\mu m$ and 100 $\mu m$.

A cross section (e.g., a first cross-section) may correspond to a diameter of a cell. In some cases, a cell may be approximately spherical. In such cases, the first cross-section may correspond to the diameter of the cell. In other cases, the cell may be approximately cylindrical. In such cases, the first cross-section may correspond to a diameter, length, or width along the approximately cylindrical cell. In some cases, the cell may comprise a surface. A cell surface may comprise one or more features. For example, a cell may comprise a dendritic receiver, flagella, roughed border, or other feature.

A characteristic or set of characteristics of a cell may be changed by one or more conditions. A condition suitable for changing a characteristic or set of characteristics of a cell may be, for example, a temperature, a pH, an ion or salt concentration, a pressure, or another condition. For example, a cell may be exposed to a chemical species that may bring about a change in one or more characteristics of the cell. In some cases, a stimulus may be used to change one or more characteristics of a cell. For example, upon application of the stimulus, one or more characteristics of a cell may be changed. The stimulus may be, for example, a thermal stimulus, a photo stimulus, a chemical stimulus, or another stimulus. In some cases, conditions sufficient to change the one or more characteristics of a cell may comprise one or more different conditions, such as a temperature and a pressure, a pH and a salt concentration, a chemical species and a temperature, or any other combination of conditions. A temperature sufficient for changing one or more characteristics of the cell may be, for example, at least about 0 degrees Celsius (° C.), 1° C., 2° C., 3° C., 4° C., 5° C., 10° C., or higher. For example, the temperature may be about 4° C. In other cases, a temperature sufficient for changing one or more characteristics of the cell may be, for example, at least about 25° C., 30° C., 35° C., 37° C., 40° C., 45° C., 50° C., or higher. For example, the temperature may be about 37° C. A pH sufficient for changing one or more characteristics of the cell may be, for example, between about 5 and 8, such as between about 6 and 7.

A biological sample may include a plurality of cells having different dimensions and features. In some cases, processing of the biological sample, such as cell separation and sorting (e.g., as described herein), may affect the distribution of dimensions and cellular features included in the sample by depleting cells having certain features and dimensions and/or isolating cells having certain features and dimensions.

A sample may undergo one or more processes in preparation for analysis (e.g., as described herein), including, but not limited to, filtration, selective precipitation, purification, centrifugation, permeabilization, isolation, agitation, heating, and/or other processes. For example, a sample may be filtered to remove a contaminant or other materials. In an example, a filtration process may comprise the use of microfluidics (e.g., to separate analyte carriers of different sizes, types, charges, or other features).

In an example, a sample comprising one or more cells may be processed to separate the one or more cells from other materials in the sample (e.g., using centrifugation and/or another process). In some cases, cells and/or cellular constituents of a sample may be processed to separate and/or sort groups of cells and/or cellular constituents, such as to separate and/or sort cells and/or cellular constituents of different types. Examples of cell separation include, but are not limited to, separation of white blood cells or immune cells from other blood cells and components, separation of circulating tumor cells from blood, and separation of bacteria from bodily cells and/or environmental materials. A separation process may comprise a positive selection process (e.g., targeting of a cell type of interest for retention for subsequent downstream analysis, such as by use of a monoclonal antibody that targets a surface marker of the cell type of interest), a negative selection process (e.g., removal of one or more cell types and retention of one or more other cell types of interest), and/or a depletion process (e.g., removal of a single cell type from a sample, such as removal of red blood cells from peripheral blood mononuclear cells).

Separation of one or more different types of cells may comprise, for example, centrifugation, filtration, microfluidic-based sorting, flow cytometry, fluorescence-activated cell sorting (FACS), magnetic-activated cell sorting (MACS), buoyancy-activated cell sorting (BACS), or any other useful method. For example, a flow cytometry method may be used to detect cells and/or cellular constituents based on a parameter such as a size, morphology, or protein expression. Flow cytometry-based cell sorting may comprise injecting a sample into a sheath fluid that conveys the cells and/or cellular constituents of the sample into a measurement region one at a time. In the measurement region, a light source such as a laser may interrogate the cells and/or cellular constituents and scattered light and/or fluorescence may be detected and converted into digital signals. A nozzle system (e.g., a vibrating nozzle system) may be used to generate droplets (e.g., aqueous droplets) comprising individual cells and/or cellular constituents. Droplets including cells and/or cellular constituents of interest (e.g., as determined via optical detection) may be labeled with an electric charge (e.g., using an electrical charging ring), which charge may be used to separate such droplets from droplets including other cells and/or cellular constituents. For example, FACS may comprise labeling cells and/or cellular constituents with fluorescent markers (e.g., using internal and/or external biomarkers). Cells and/or cellular constituents may then be measured and identified one by one and sorted based on the emitted fluorescence of the marker or absence thereof. MACS may use micro- or nano-scale magnetic particles to bind to cells and/or cellular constituents (e.g., via an antibody interaction with cell surface markers) to facilitate magnetic isolation of cells and/or cellular constituents of interest from other components of a sample (e.g., using a column-based analysis). BACS may use microbubbles (e.g., glass microbubbles) labeled with antibodies to target cells of interest. Cells and/or cellular components coupled to microbubbles may float to a surface of a solution, thereby separating target cells and/or cellular components from other components of a sample. Cell separation techniques may be used to enrich for populations of cells of interest (e.g., prior to partitioning, as described herein). For example, a sample comprising a plurality of cells including a plurality of cells of a given type may be subjected to a positive separation process. The plurality of cells of the given type may be labeled with a fluorescent marker (e.g., based on an expressed cell surface marker or another marker) and subjected to a FACS process to separate these cells from other cells of the plurality of cells. The selected cells may then be subjected to subsequent partition-based analysis (e.g., as described herein) or other downstream analysis. The fluorescent marker may be removed prior to such analysis or may be retained. The fluorescent marker may comprise an identifying feature, such as a nucleic acid barcode sequence and/or unique molecular identifier.

In another example, a first sample comprising a first plurality of cells including a first plurality of cells of a given type (e.g., immune cells expressing a particular marker or combination of markers) and a second sample comprising a second plurality of cells including a second plurality of cells of the given type may be subjected to a positive separation process. The first and second samples may be collected from the same or different subjects, at the same or different types, from the same or different bodily locations or systems, using the same or different collection techniques. For example, the first sample may be from a first subject and the second sample may be from a second subject different than the first subject. The first plurality of cells of the first sample may be provided a first plurality of fluorescent markers configured to label the first plurality of cells of the given type. The second plurality of cells of the second sample may be provided a second plurality of fluorescent markers configured to label the second plurality of cells of the given type. The first plurality of fluorescent markers may include a first identifying feature, such as a first barcode, while the second plurality of fluorescent markers may include a second identifying feature, such as a second barcode, that is different than the first identifying feature. The first plurality of fluorescent markers and the second plurality of fluorescent markers may fluoresce at the same intensities and over the same range of wavelengths upon excitation with a same excitation source (e.g., light source, such as a laser). The first and second samples may then be combined and subjected to a FACS process to separate cells of the given type from other cells based on the first plurality of fluorescent markers labeling the first plurality of cells of the given type and the second plurality of fluorescent markers labeling the second plurality of cells of the given type. Alternatively, the first and second samples may undergo separate FACS processes and the positively selected cells of the given type from the first sample and the positively selected cells of the given type from the second sample may then be combined for subsequent analysis. The encoded identifying features of the different fluorescent markers may be used to identify cells originating from the first sample and cells originating from the second sample. For example, the first and second identifying features may be configured to interact (e.g., in partitions, as described herein) with nucleic acid barcode molecules (e.g., as described herein) to generate barcoded nucleic acid products detectable using, e.g., nucleic acid sequencing.

Multiplexing & 5'

The present disclosures provides methods and systems for multiplexing, and otherwise increasing throughput in, analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cell features may be used to characterize analyte carriers and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, each of which is herein entirely incorporated by reference for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In some aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labelling agents capable of binding to or otherwise coupling to one or more analyte carriers may be used to characterize an analyte carrier as belonging to a particular set of analyte carriers. For example, labeling agents may be used to label a sample of cells or a group of cells. In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling an analyte carrier may comprise subjecting the antibody-linked barcode molecule or the epitope binding fragment-linked barcode molecule to conditions suitable for binding the antibody to a molecule present on a surface of the analyte carrier. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 μM, 90 μM, 80 μM, 70 μM, 60 μM, 50 μM, 40 μM, 30 μM, 20 μM, 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 pM.

In another example, a reporter oligonucleotide may be coupled to a cell-penetrating peptide (CPP), and labeling cells may comprise delivering the CPP coupled reporter oligonucleotide into an analyte carrier Labeling analyte carriers may comprise delivering the CPP conjugated oligonucleotide into a cell and/or cell bead by the cell-penetrating peptide. A cell-penetrating peptide that can be used in the methods provided herein can comprise at least one non-functional cysteine residue, which may be either free or derivatized to form a disulfide link with an oligonucleotide that has been modified for such linkage. Non-limiting examples of cell-penetrating peptides that can be used in embodiments herein include penetratin, transportan, plsl, TAT(48-60), pVEC, MTS, and MAP). Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The cell-penetrating peptide may be an arginine-rich peptide transporter. The cell-penetrating peptide may be Penetratin or the Tat peptide.

In another example, a reporter oligonucleotide may be coupled to a fluorophore or dye, and labeling cells may comprise subjecting the fluorophore-linked barcode molecule to conditions suitable for binding the fluorophore to the surface of the analyte carrier. In some instances, fluorophores can interact strongly with lipid bilayers and labeling analyte carriers may comprise subjecting the fluorophore-linked barcode molecule to conditions such that the fluorophore binds to or is inserted into a membrane of the analyte carrier. In some cases, the fluorophore is a water-soluble, organic fluorophore. In some instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. PLoS One. 2014 Feb. 4; 9(2):e87649, which is hereby incorporated by reference in its entirety for all purposes, for a description of organic fluorophores.

A reporter oligonucleotide may be coupled to a lipophilic molecule, and labeling analyte carriers may comprise delivering the nucleic acid barcode molecule to a membrane of the analyte carrier or a nuclear membrane by the lipophilic molecule. Lipophilic molecules can associate with and/or insert into lipid membranes such as cell membranes and nuclear membranes. In some cases, the insertion can be reversible in some cases, the association between the lipophilic molecule and analyte carrier may be such that the analyte carrier retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

As described elsewhere herein, libraries of labelling agents may be associated with a particular cell feature as well as be used to identify analytes as originating from a particular analyte carrier, population, or sample. The analyte carriers may be incubated with a plurality of libraries and a given analyte carrier may comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 30:
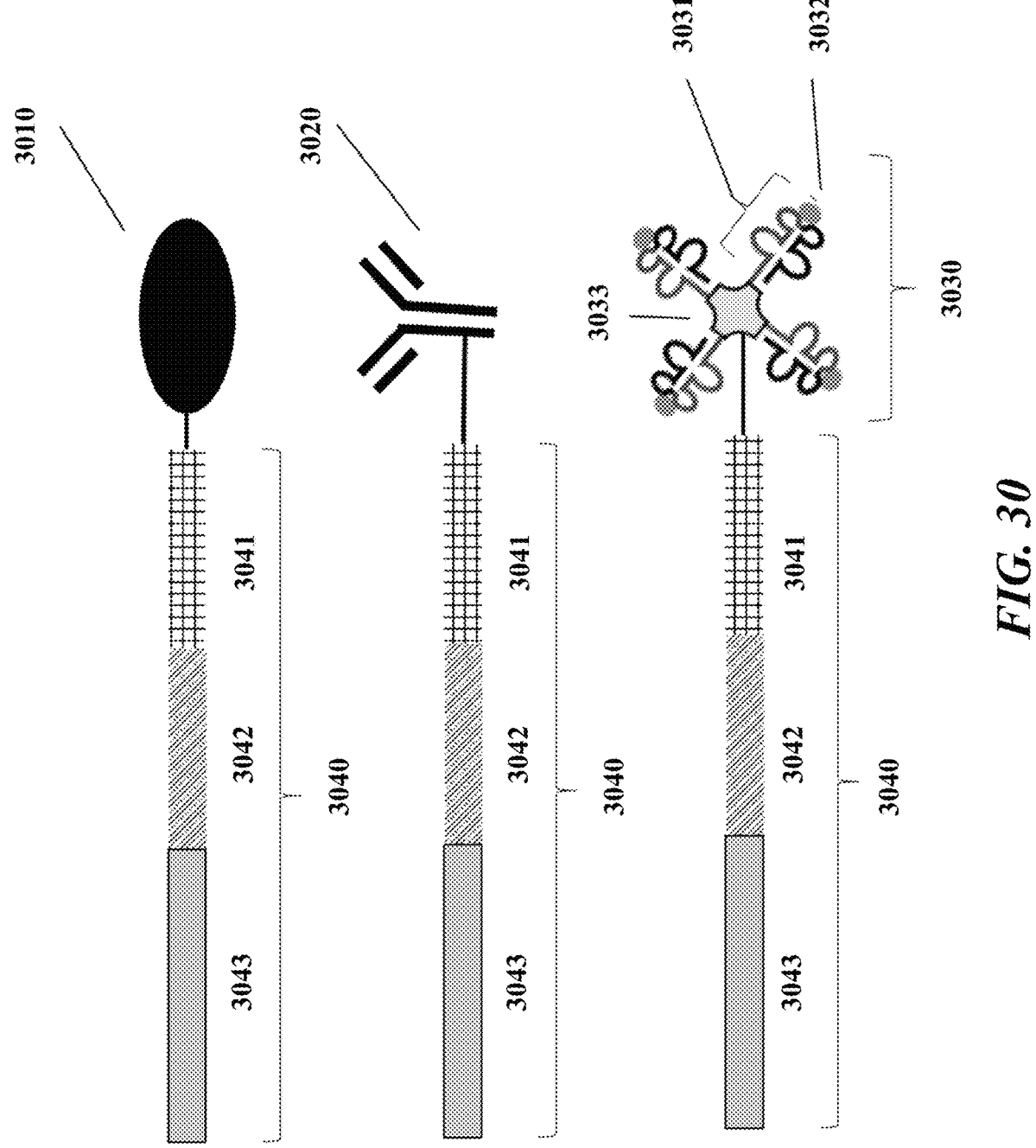
FIG. 30 schematically illustrates example labelling agents with nucleic acid molecules attached thereto.

FIG. 30 describes exemplary labelling agents (3010, 3020, 3030) comprising reporter oligonucleotides (3040) attached thereto. Labelling agent 3010 (e.g., any of the labelling agents described herein) is attached (either directly, e.g., covalently attached, or indirectly) to reporter oligonucleotide 3040. Reporter oligonucleotide 3040 may comprise barcode sequence 3042 that identifies labelling agent 3010. Reporter oligonucleotide 3040 may also comprise one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 30, in some instances, reporter oligonucleotide 3040 conjugated to a labelling agent (e.g., 3010, 3020, 3030) comprises a primer sequence 3041, a barcode sequence that identifies the labelling agent (e.g., 3010, 3020, 3030), and functional sequence 3043. Functional sequence 3043 may be configured to hybridize to a complementary sequence, such as a complementary sequence present on a nucleic acid barcode molecule 3090 (not shown), such as those described elsewhere herein. In some instances, nucleic acid barcode molecule 3090 is attached to a support (e.g., a bead, such as a gel bead), such as those described elsewhere herein. For example, nucleic acid barcode molecule 3090 may be attached to the support via a releasable linkage (e.g., comprising a labile bond), such as those described elsewhere herein. In some instances, reporter oligonucleotide 3040 comprises one or more additional functional sequences, such as those described above.

In some instances, the labelling agent 3010 is a protein or polypeptide (e.g., an antigen or prospective antigen) comprising reporter oligonucleotide 3040. Reporter oligonucleotide 3040 comprises barcode sequence 3042 that identifies polypeptide 3010 and can be used to infer the presence of an analyte, e.g., a binding partner of polypeptide 3010 (i.e., a molecule or compound to which polypeptide 3010 can bind). In some instances, the labelling agent 3010 is a lipophilic moiety (e.g., cholesterol) comprising reporter oligonucleotide 3040, where the lipophilic moiety is selected such that labelling agent 3010 integrates into a membrane of a cell or nucleus. Reporter oligonucleotide 3040 comprises barcode sequence 3042 that identifies lipophilic moiety 3010 which in some instances is used to tag cells (e.g., groups of cells, cell samples, etc.) and may be used for multiplex analyses as described elsewhere herein. In some instances, the labelling agent is an antibody 3020 (or an epitope binding fragment thereof) comprising reporter oligonucleotide 3040. Reporter oligonucleotide 3040 comprises barcode sequence 3042 that identifies antibody 3020 and can be used to infer the presence of, e.g., a target of antibody 3020 (i.e., a molecule or compound to which antibody 3020 binds). In other embodiments, labelling agent 3030 comprises an MHC molecule 3031 comprising peptide 3032 and reporter oligonucleotide 3040 that identifies peptide 3032. In some instances, the MHC molecule is coupled to a support 3033. In some instances, support 3033 may be a polypeptide, such as streptavidin, or a polysaccharide, such as dextran. In some instances, reporter oligonucleotide 3040 may be directly or indirectly coupled to MHC labelling agent 3030 in any suitable manner. For example, reporter oligonucleotide 3040 may be coupled to MHC molecule 3031, support 3033, or peptide 3032. In some embodiments, labelling agent 3030 comprises a plurality of MHC molecules, (e.g. is an MHC multimer, which may be coupled to a support (e.g., 3033)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

Figures 31A, 31B:
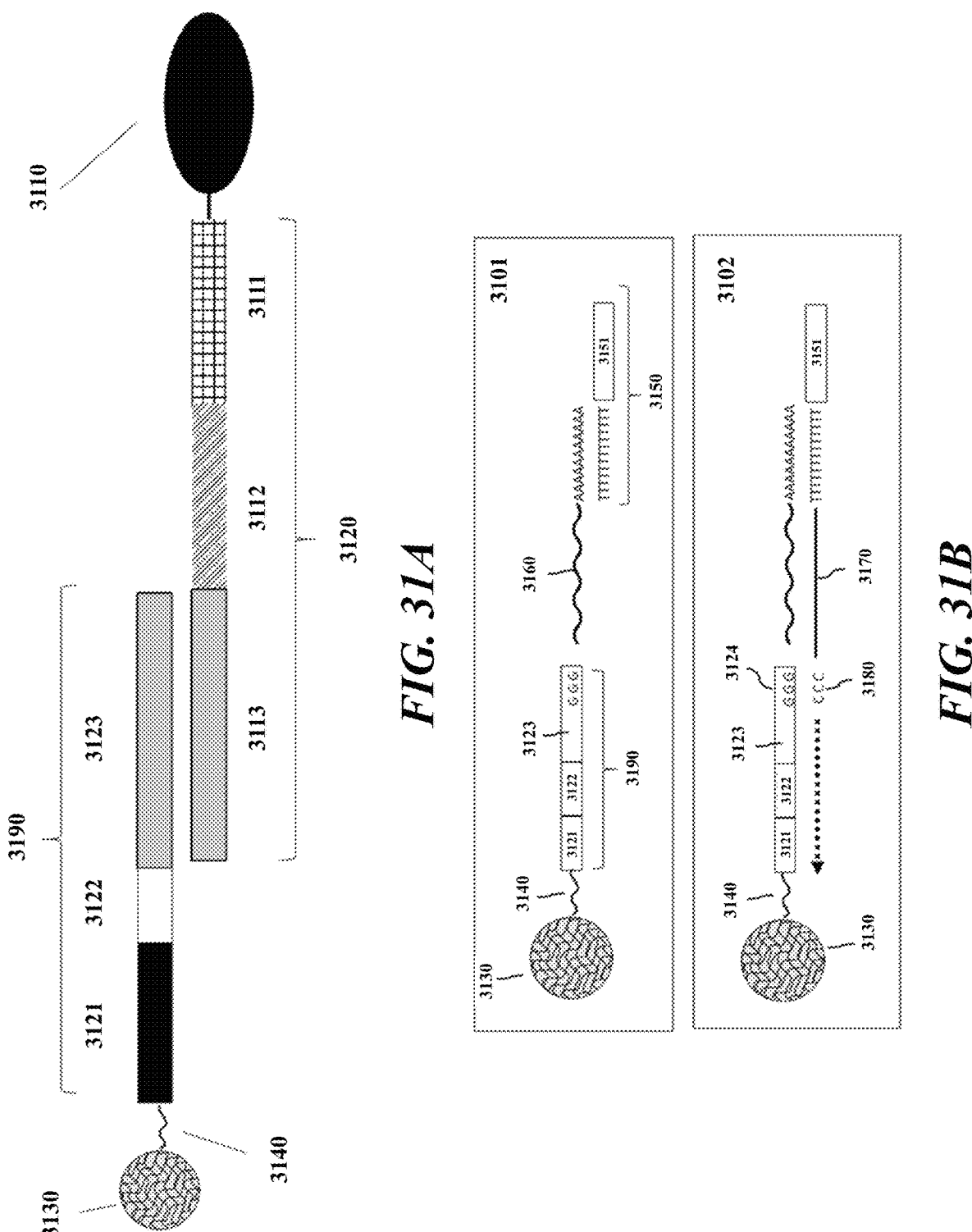
FIG. 31A schematically shows an example of labelling agents.
FIG. 31B schematically shows another example workflow for processing nucleic acid molecules.
Figure 31C:
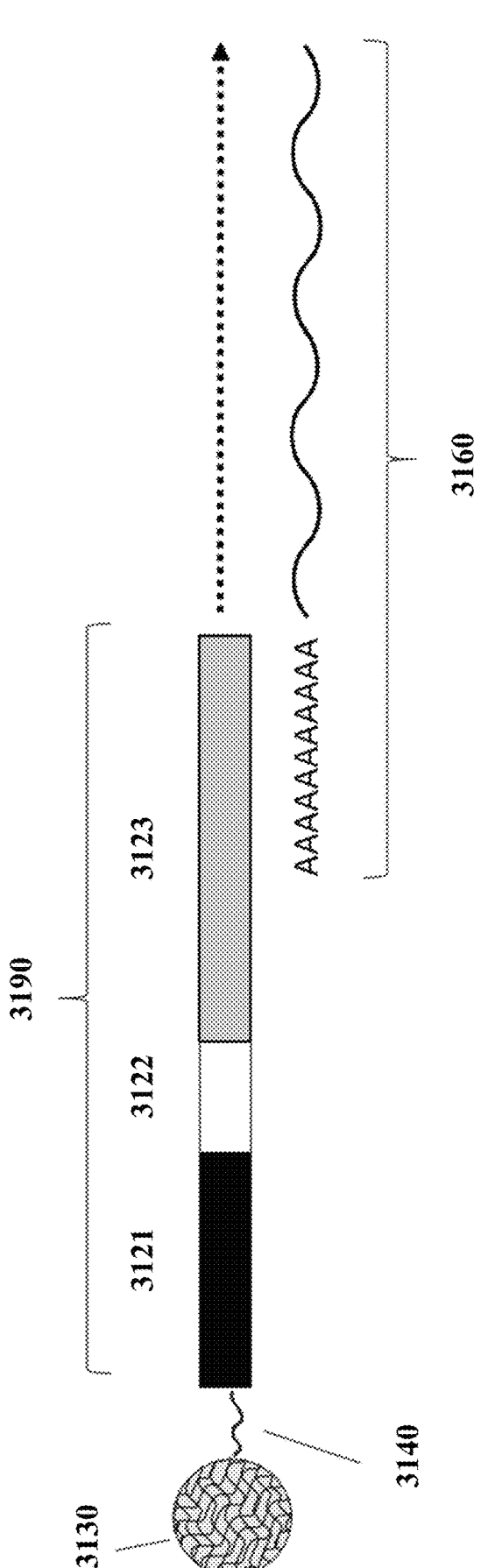
FIG. 31C schematically shows another example workflow for processing nucleic acid molecules.
Figure 32:
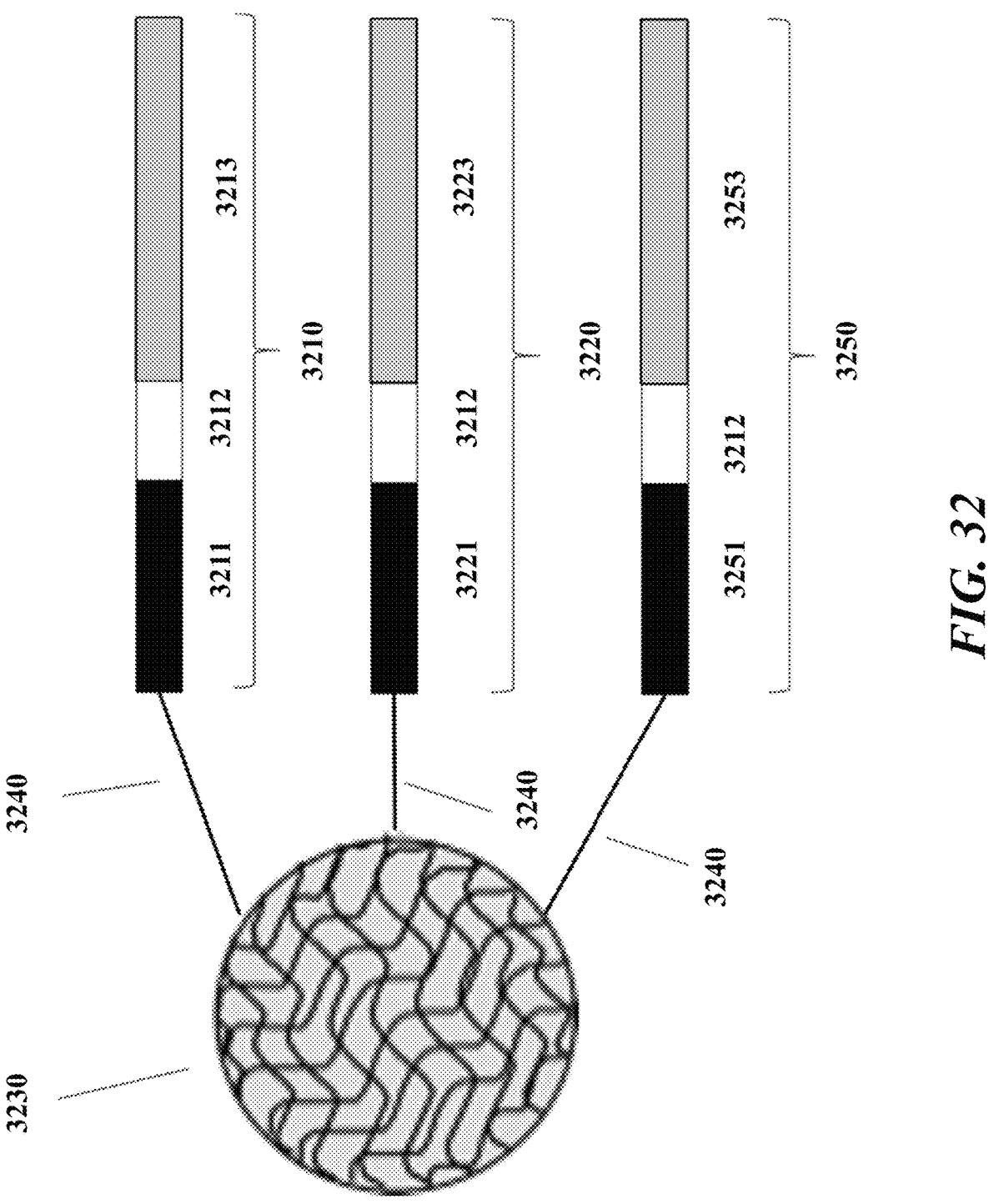
FIG. 32 schematically shows another example of a barcode-carrying bead.

FIG. 32 illustrates another example of a barcode carrying bead. In some embodiments, analysis of multiple analytes (e.g., RNA and one or more analytes using labelling agents described herein) may comprise nucleic acid barcode molecules as generally depicted in FIG. 32. In some embodiments, nucleic acid barcode molecules 3210 and 3220 are attached to support 3230 via a releasable linkage 3240 (e.g., comprising a labile bond) as described elsewhere herein. Nucleic acid barcode molecule 3210 may comprise adapter sequence 3211, barcode sequence 3212 and adapter sequence 3213. Nucleic acid barcode molecule 3220 may comprise adapter sequence 3221, barcode sequence 3212, and adapter sequence 3223, wherein adapter sequence 3223 comprises a different sequence than adapter sequence 3213. In some instances, adapter 3211 and adapter 3221 comprise the same sequence. In some instances, adapter 3211 and adapter 3221 comprise different sequences. Although support 3230 is shown comprising nucleic acid barcode molecules 3210 and 3220, any suitable number of barcode molecules comprising common barcode sequence 3212 are contemplated herein. For example, in some embodiments, support 3230 further comprises nucleic acid barcode molecule 3250. Nucleic acid barcode molecule 3250 may comprise adapter sequence 3251, barcode sequence 3212 and adapter sequence 3253, wherein adapter sequence 3253 comprises a different sequence than adapter sequence 3213 and 3223. In some instances, nucleic acid barcode molecules (e.g., 3210, 3220, 3250) comprise one or more additional functional sequences, such as a UMI or other sequences described herein. The nucleic acid barcode molecules 3210, 3220 or 3250 may interact with analytes as described elsewhere herein, for example, as depicted in FIGS. 31A-C.

Referring to FIG. 31A, in an instance where cells are labelled with labeling agents, sequence 3123 may be complementary to an adapter sequence of a reporter oligonucleotide. Cells may be contacted with one or more reporter oligonucleotide 3120 conjugated labelling agents 3110 (e.g., polypeptide, antibody, or others described elsewhere herein). In some cases, the cells may be further processed prior to barcoding. For example, such processing steps may include one or more washing and/or cell sorting steps. In some instances, a cell that is bound to labelling agent 3110 which is conjugated to oligonucleotide 3120 and support 3130 (e.g., a bead, such as a gel bead) comprising nucleic acid barcode molecule 3190 is partitioned into a partition amongst a plurality of partitions (e.g., a droplet of a droplet emulsion or a well of a microwell array). In some instances, the partition comprises at most a single cell bound to labelling agent 3110. In some instances, reporter oligonucleotide 3120 conjugated to labelling agent 3110 (e.g., polypeptide, an antibody, pMHC molecule such as an MHC multimer, etc.) comprises a first adapter sequence 3111 (e.g., a primer sequence), a barcode sequence 3112 that identifies the labelling agent 3110 (e.g., the polypeptide, antibody, or peptide of a pMHC molecule or complex), and an adapter sequence 3113. Adapter sequence 3113 may be configured to hybridize to a complementary sequence, such as sequence 3123 present on a nucleic acid barcode molecule 3190. In some instances, oligonucleotide 3120 comprises one or more additional functional sequences, such as those described elsewhere herein.

Barcoded nucleic may be generated (e.g., via a nucleic acid reaction, such as nucleic acid extension or ligation) from the constructs described in FIGS. 31A-C. For example, sequence 3113 may then be hybridized to complementary sequence 3123 to generate (e.g., via a nucleic acid reaction, such as nucleic acid extension or ligation) a barcoded nucleic acid molecule comprising cell (e.g., partition specific) barcode sequence 3122 (or a reverse complement thereof) and reporter barcode sequence 3112 (or a reverse complement thereof). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 31A-C, or a combination of workflows for an individual analyte, as described elsewhere herein. For example, by using a combination of the workflows as generally depicted in FIGS. 31A-C, multiple analytes can be analyzed.

In some instances, analysis of an analyte (e.g. a nucleic acid, a polypeptides, a carbohydrate, a lipid, etc.) comprises a workflow as generally depicted in FIG. 31A. A nucleic acid barcode molecule 3190 may be co-partitioned with the one or more analytes. In some instances, nucleic acid barcode molecule 3190 is attached to a support 3130 (e.g., a bead, such as a gel bead), such as those described elsewhere herein. For example, nucleic acid barcode molecule 3190 may be attached to support 3130 via a releasable linkage 3140 (e.g., comprising a labile bond), such as those described elsewhere herein. Nucleic acid barcode molecule 3190 may comprise a barcode sequence 3121 and optionally comprise other additional sequences, for example, a UMI sequence 3122 (or other functional sequences described elsewhere herein). The nucleic acid barcode molecule 3190 may comprise a sequence 3123 that may be complementary to another nucleic acid sequence, such that it may hybridize to a particular sequence.

For example, sequence 3123 may comprise a poly-T sequence and may be used to hybridize to mRNA. Referring to FIG. 31C, in some embodiments, nucleic acid barcode molecule 3190 comprises sequence 3123 complementary to a sequence of RNA molecule 3160 from a cell. In some instances, sequence 3123 comprises a sequence specific for an RNA molecule. Sequence 3123 may comprise a known or targeted sequence or a random sequence. In some instances, a nucleic acid extension reaction may be performed, thereby generating a barcoded nucleic acid product comprising sequence 3123, the barcode sequence 3121, UMI sequence 3122, any other functional sequence, and a sequence corresponding to the RNA molecule 3160.

In another example, sequence 3123 may be complementary to an overhang sequence or an adapter sequence that has been appended to an analyte. For example, referring to FIG. 31B, panel 3101, in some embodiments, primer 3150 comprises a sequence complementary to a sequence of nucleic acid molecule 3160 (such as an RNA encoding for a BCR sequence) from an analyte carrier. In some instances, primer 3150 comprises one or more sequences 3151 that are not complementary to RNA molecule 3160. Sequence 3151 may be a functional sequence as described elsewhere herein, for example, an adapter sequence, a sequencing primer sequence, or a sequence the facilitates coupling to a flow cell of a sequencer. In some instances, primer 3150 comprises a poly-T sequence. In some instances, primer 3150 comprises a sequence complementary to a target sequence in an RNA molecule. In some instances, primer 3150 comprises a sequence complementary to a region of an immune molecule, such as the constant region of a TCR or BCR sequence. Primer 3150 is hybridized to nucleic acid molecule 3160 and complementary molecule 3170 is generated (see Panel 3102). For example, complementary molecule 3170 may be cDNA generated in a reverse transcription reaction. In some instances, an additional sequence may be appended to complementary molecule 3170. For example, the reverse transcriptase enzyme may be selected such that several non-templated bases 3180 (e.g., a poly-C sequence) are appended to the cDNA. In another example, a terminal transferase may also be used to append the additional sequence. Nucleic acid barcode molecule 3190 comprises a sequence 3124 complementary to the non-templated bases, and the reverse transcriptase performs a template switching reaction onto nucleic acid barcode molecule 3190 to generate a barcoded nucleic acid molecule comprising cell (e.g., partition specific) barcode sequence 3122 (or a reverse complement thereof) and a sequence of complementary molecule 3170 (or a portion thereof). In some instances, sequence 3123 comprises a sequence complementary to a region of an immune molecule, such as the constant region of a TCR or BCR sequence. Sequence 3123 is hybridized to nucleic acid molecule 3160 and a complementary molecule 3170 is generated. For example complementary molecule 3170 may be generated in a reverse transcription reaction generating a barcoded nucleic acid molecule comprising cell (e.g., partition specific) barcode sequence 3122 (or a reverse complement thereof) and a sequence of complementary molecule 3170 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in International Patent Application WO2018/075693, U.S. Patent Publication No. 2018/0105808, U S Patent Publication No 2015/0376609, filed Jun. 26, 2015, and U.S. Patent Publication No. 2019/0367969, each of which applications is herein entirely incorporated by reference for all purposes.
Reagents In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
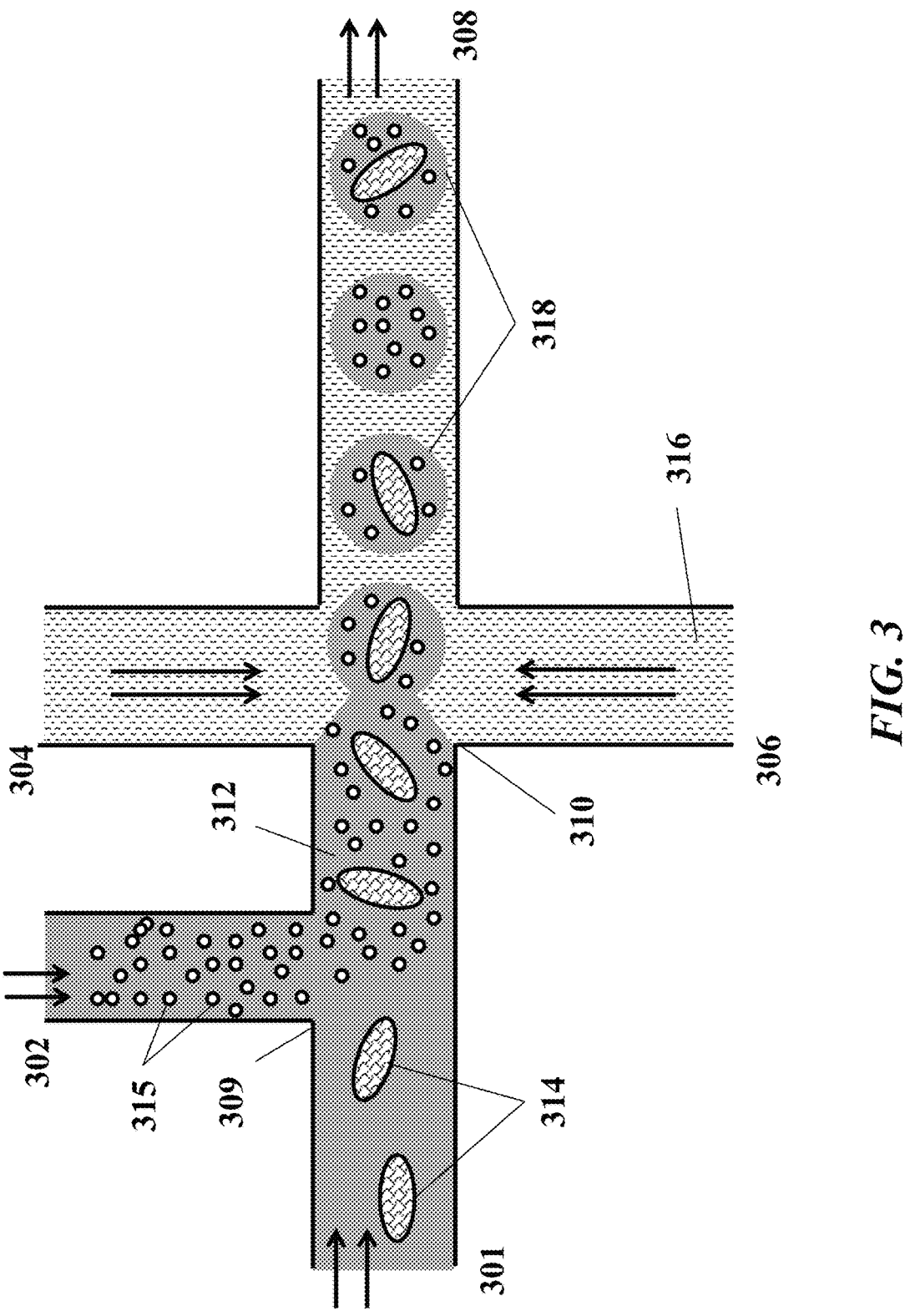
FIG. 3 shows an example of a microfluidic channel structure for co-partitioning biological particles and reagents

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The methods and systems of the present disclosure may comprise microfluidic devices and methods of use thereof, which may be used for co-partitioning analyte carriers or analyte carriers with reagents. Such systems and methods are described in U.S. Patent Publication No. US/20190367997, which is herein incorporated by reference in its entirety for all purposes.

Beneficially, when lysis reagents and biological particles are co-partitioned, the lysis reagents can facilitate the release of the contents of the biological particles within the partition. The contents released in a partition may remain discrete from the contents of other partitions.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion-based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the analyte carriers described above, other reagents can also be co-partitioned with the analyte carriers, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated analyte carriers (e.g., a cell or a nucleus in a polymer matrix), the analyte carriers may be exposed to an appropriate stimulus to release the analyte carriers or their contents from a co-partitioned microcapsule. For example, in some cases, a chemical stimulus may be co-partitioned along with an encapsulated analyte carrier to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative examples, this may be a different and non-overlapping stimulus, in order to allow an encapsulated analyte carrier to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. 20190100632, which are each incorporated by reference in their entirety.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the analyte. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Di-aminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying nucleic acids (e.g., mRNA, the genomic DNA) from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
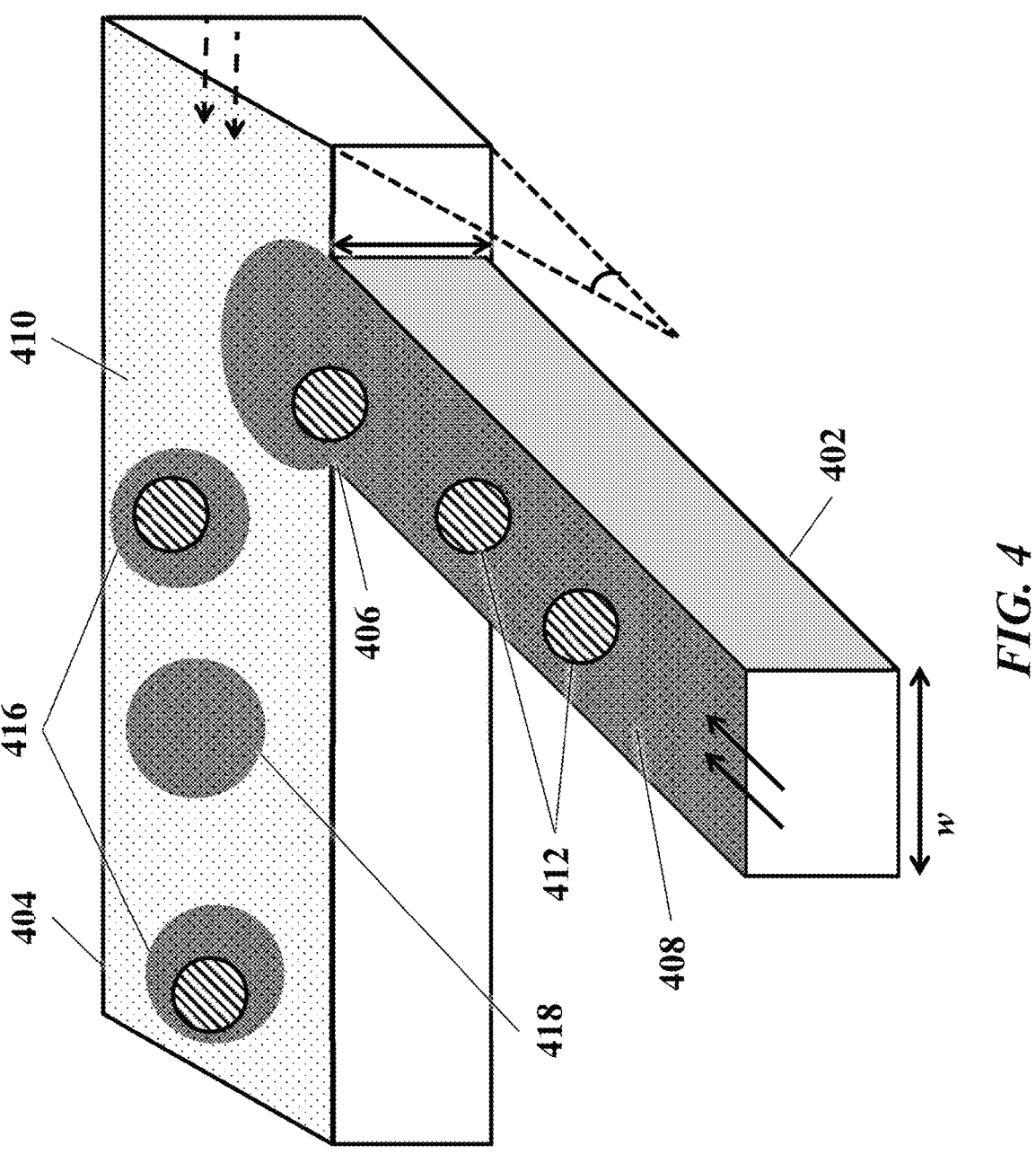
FIG. 4 shows an example of a microfluidic channel structure for the controlled partitioning of beads into discrete droplets

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, $\alpha$. The expansion angle, $\alpha$, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha \frac{w}{h_0}}\right)\frac{h_0}{\sqrt{\tan\alpha}}$$

By way of example, for a channel structure with w=21 μm, h=21 μm, and $\alpha$=3°, the predicted droplet size is 121 μm. In another example, for a channel structure with w=25 μm, h=25 μm, and $\alpha$=5°, the predicted droplet size is 123 μm. In another example, for a channel structure with w=28 μm, h=28 μm, and $\alpha$=7°, the predicted droplet size is 124 μm.

In some instances, the expansion angle, $\alpha$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
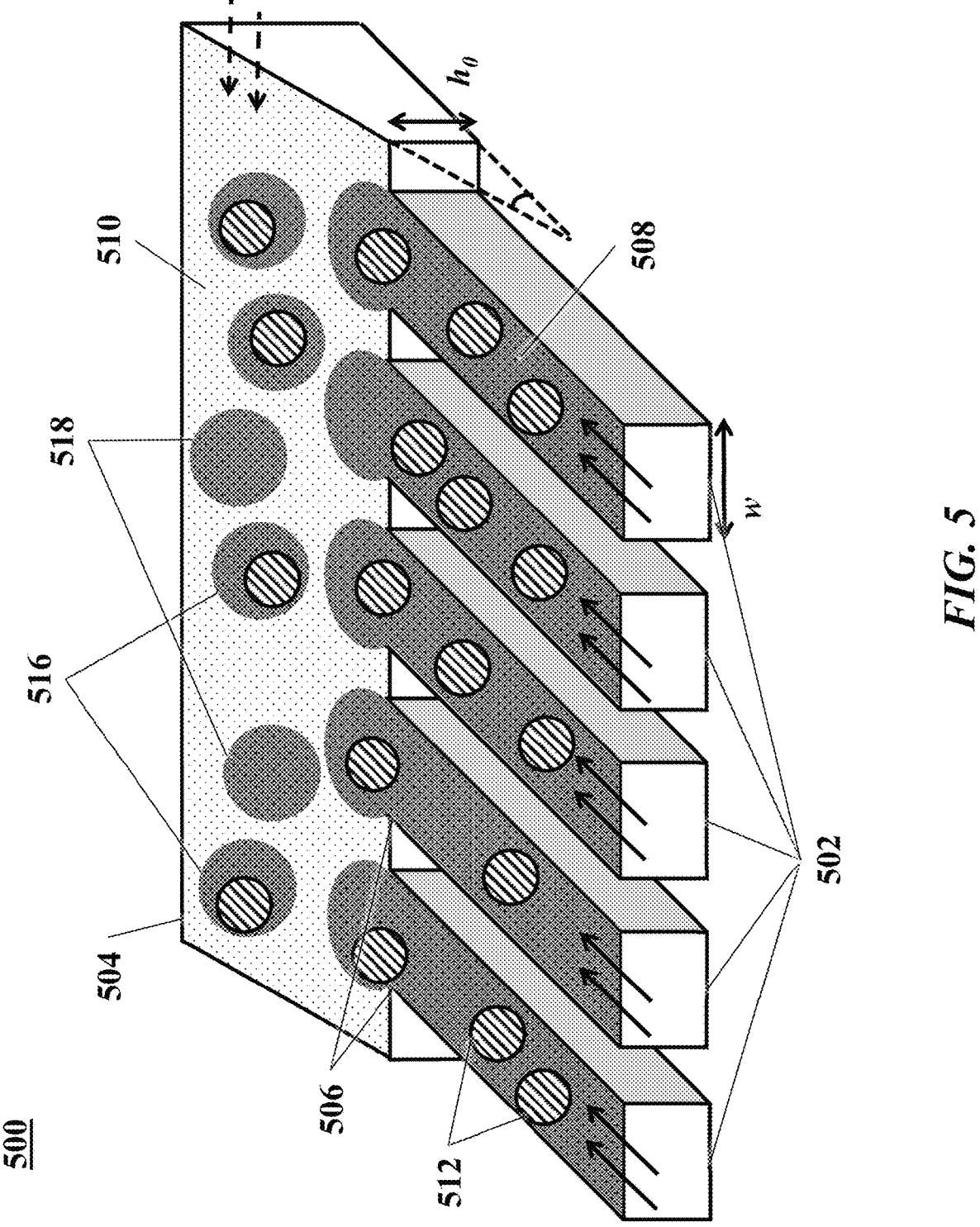
FIG. 5 shows an example of a microfluidic channel structure for increased droplet generation throughput

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
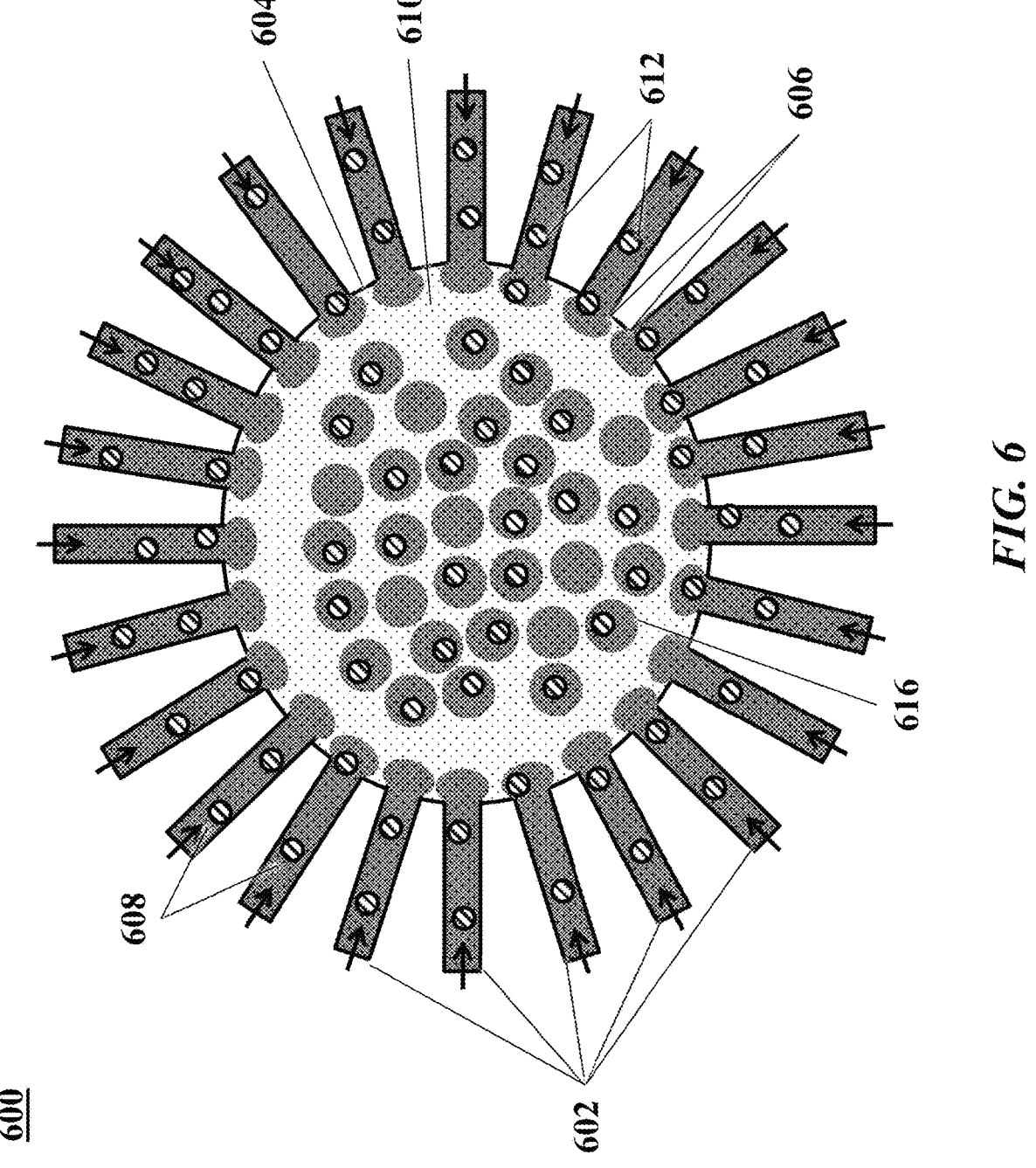
FIG. 6 shows another example of a microfluidic channel structure for increased droplet generation throughput

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation.

The channel segment 402 from the channel structure 400 in FIG. 4 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_0$, at or near the channel junction. The geometric parameters, w, $h_0$ and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figures 7A, 7B:
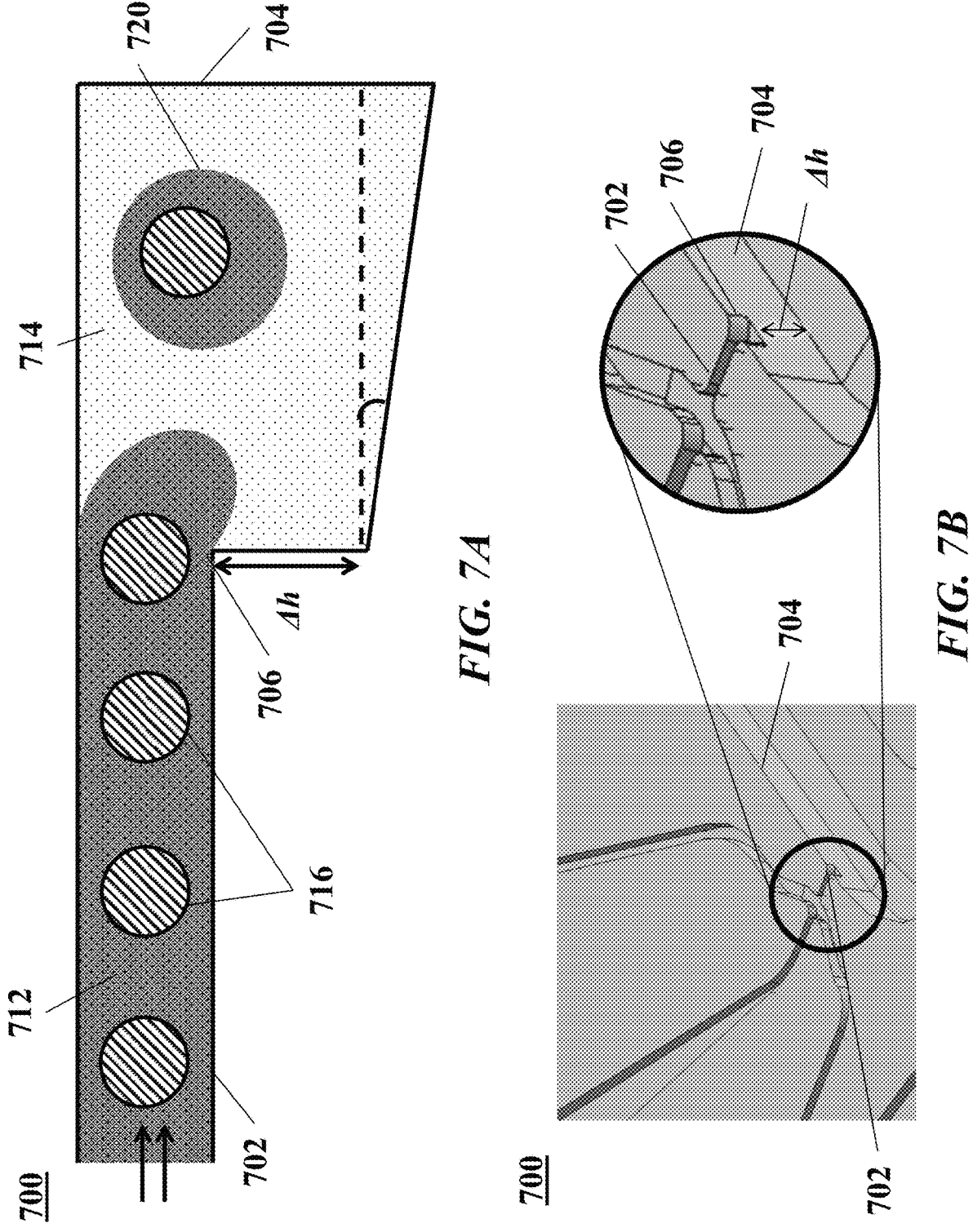
FIG. 7A shows a cross-section view of another example of a microfluidic channel structure with a geometric feature for controlled partitioning.
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., Δh, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\beta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, $\beta$), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 27:
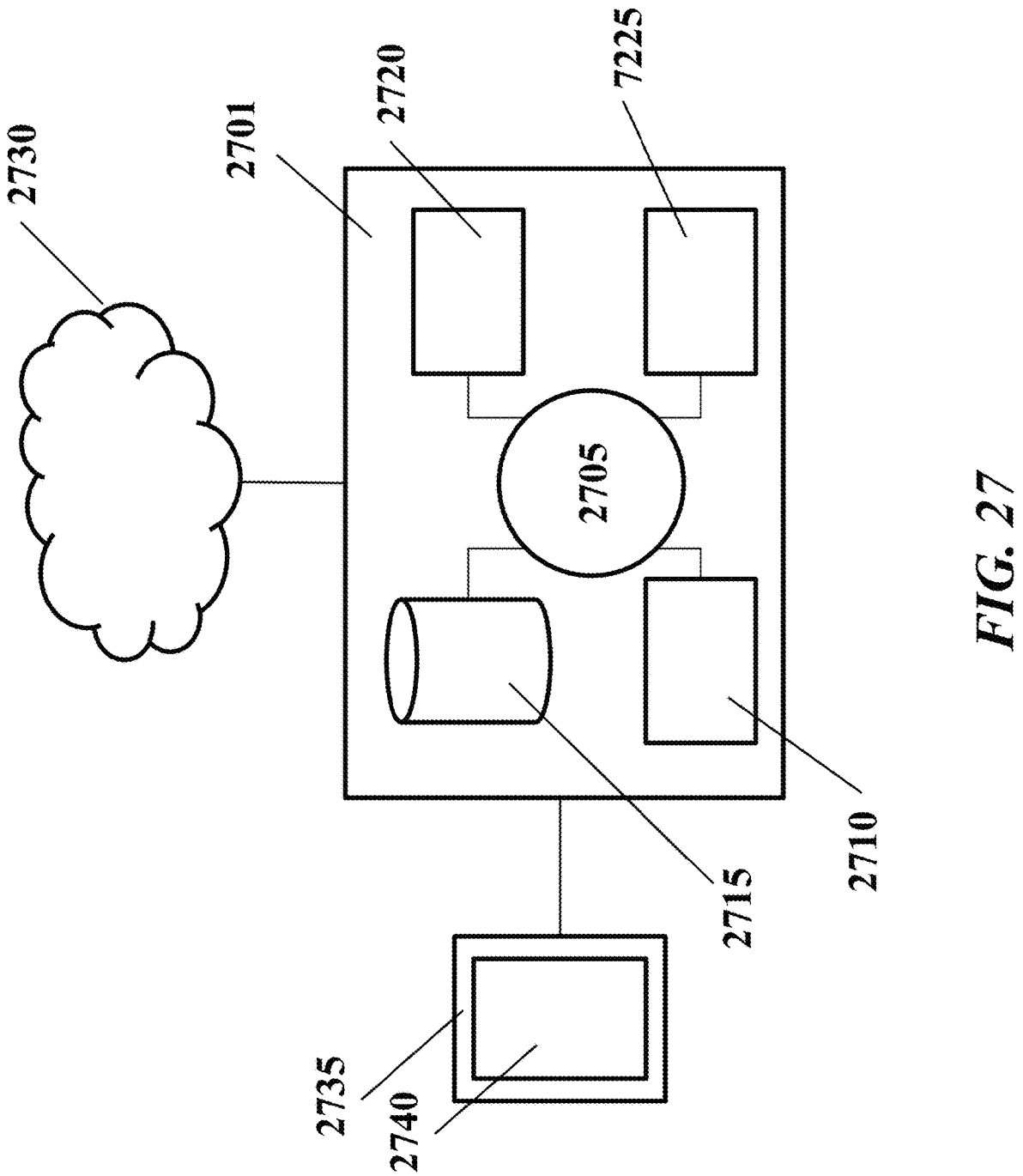
FIG. 27 shows a computer system that is programmed or otherwise configured to implement methods provided herein.

The present disclosure provides computer systems that are programmed to implement methods of the disclosure. FIG. 27 shows a computer system 2701 that is programmed or otherwise configured to performed the methods of the present disclosure such as controlling the conditions of experiments, process automation for performing the experiments, and more. Such methods may comprise microscopy, fluorometry, sequencing, and/or any other detection technique. For example, computer systems may be used to automate a microscope stage, a robotic system for performing experiments, control a microfluidic perform and perform other functions. The computer-aided methods may comprise detecting sequence data/reads from the assays of the present disclosure, saving and/or storing such data in a memory or database, analyzing the data using various techniques, and providing outputs indicative of the results of the experiments. The computer system 2801 can regulate various aspects of the present disclosure, such as, for example, regulating fluid flow rate in one or more channels in a microfluidic structure, performing and/or control the formation of partitions such as droplets, controlling device inputs and outputs, and more. The computer systems may be used to control a motorized stage of a microscope on which an assay of the present disclosure may be performed. The computer system and a software thereof may collect data, store data, display data, visualize data, plot data, and transfer data. Data may comprise any format. Data may comprise images. Data may comprise signals. Signals may be fluorescent measurements, sequence reads, or any other kind of signals. Data may comprise sequence reads of any kind. Data may comprise big data.

The computer system 2701 can be an electronic device of a user or a computer system that is remotely located with respect to the electronic device. The electronic device can be a mobile electronic device. The computer system 2701 includes a central processing unit (CPU, also "processor" and "computer processor" herein) 2705, which can be a single core or multi core processor, or a plurality of processors for parallel processing. The computer system 2701 also includes memory or memory location 2710 (e.g., random-access memory, read-only memory, flash memory), electronic storage unit 2715 (e.g., hard disk), communication interface 2720 (e.g., network adapter) for communicating with one or more other systems, and peripheral devices 2725, such as cache, other memory, data storage and/or electronic display adapters. The memory 2710, storage unit 2715, interface 2720 and peripheral devices 2725 are in communication with the CPU 2705 through a communication bus (solid lines), such as a motherboard. The storage unit 2715 can be a data storage unit (or data repository) for storing data. The computer system 2701 can be operatively coupled to a computer network ("network") 2730 with the aid of the communication interface 2720. The network 2730 can be the Internet, an internet and/or extranet, or an intranet and/or extranet that is in communication with the Internet. The network 2730 in some cases is a telecommunication and/or data network. The network 2730 can include one or more computer servers, which can enable distributed computing, such as cloud computing. The network 2730, in some cases with the aid of the computer system 2701, can implement a peer-to-peer network, which may enable devices coupled to the computer system 2701 to behave as a client or a server.

The CPU 2705 can execute a sequence of machine-readable instructions, which can be embodied in a program or software. The instructions may be stored in a memory location, such as the memory 2710. The instructions can be directed to the CPU 2705, which can subsequently program or otherwise configure the CPU 2705 to implement methods of the present disclosure. Examples of operations performed by the CPU 2705 can include fetch, decode, execute, and writeback.

The CPU 2705 can be part of a circuit, such as an integrated circuit. One or more other components of the system 2701 can be included in the circuit. In some cases, the circuit is an application specific integrated circuit (ASIC).

The storage unit 2715 can store files, such as drivers, libraries and saved programs. The storage unit 2715 can store user data, e.g., user preferences and user programs. The computer system 2701 in some cases can include one or more additional data storage units that are external to the computer system 2701, such as located on a remote server that is in communication with the computer system 2701 through an intranet or the Internet.

The computer system 2701 can communicate with one or more remote computer systems through the network 2730. For instance, the computer system 2701 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2701 via the network 2730.

Methods as described herein can be implemented by way of machine (e.g., computer processor) executable code stored on an electronic storage location of the computer system 2701, such as, for example, on the memory 2710 or electronic storage unit 2715. The machine executable or machine-readable code can be provided in the form of software. During use, the code can be executed by the processor 2705. In some cases, the code can be retrieved from the storage unit 2715 and stored on the memory 2710 for ready access by the processor 2705. In some situations, the electronic storage unit 2715 can be precluded, and machine-executable instructions are stored on memory 2710.

The code can be pre-compiled and configured for use with a machine having a processor adapted to execute the code or can be compiled during runtime. The code can be supplied in a programming language that can be selected to enable the code to execute in a pre-compiled or as-compiled fashion.

Aspects of the systems and methods provided herein, such as the computer system 2701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2701 can include or be in communication with an electronic display 1235 that comprises a user interface (UI) 2740 for providing, for example, results of sequencing analysis. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1205. Methods such as algorithm may comprise bioinformatics techniques. Algorithms may comprise algorithms for statistical analysis such as hypothesis testing, analysis of variance (ANOVA), performing t-tests, and other statistical techniques. Algorithms may be configured to cluster data. Methods may comprise cluster analysis. Examples of techniques which may be used may comprise k-means, hierarchical clustering, and other techniques. Methods may comprise using machine learning. A variety of platforms or programming languages such as C, C++, MATLAB, Python, R, or other languages may be used.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

EXAMPLES

Example 1

Figure 25A:
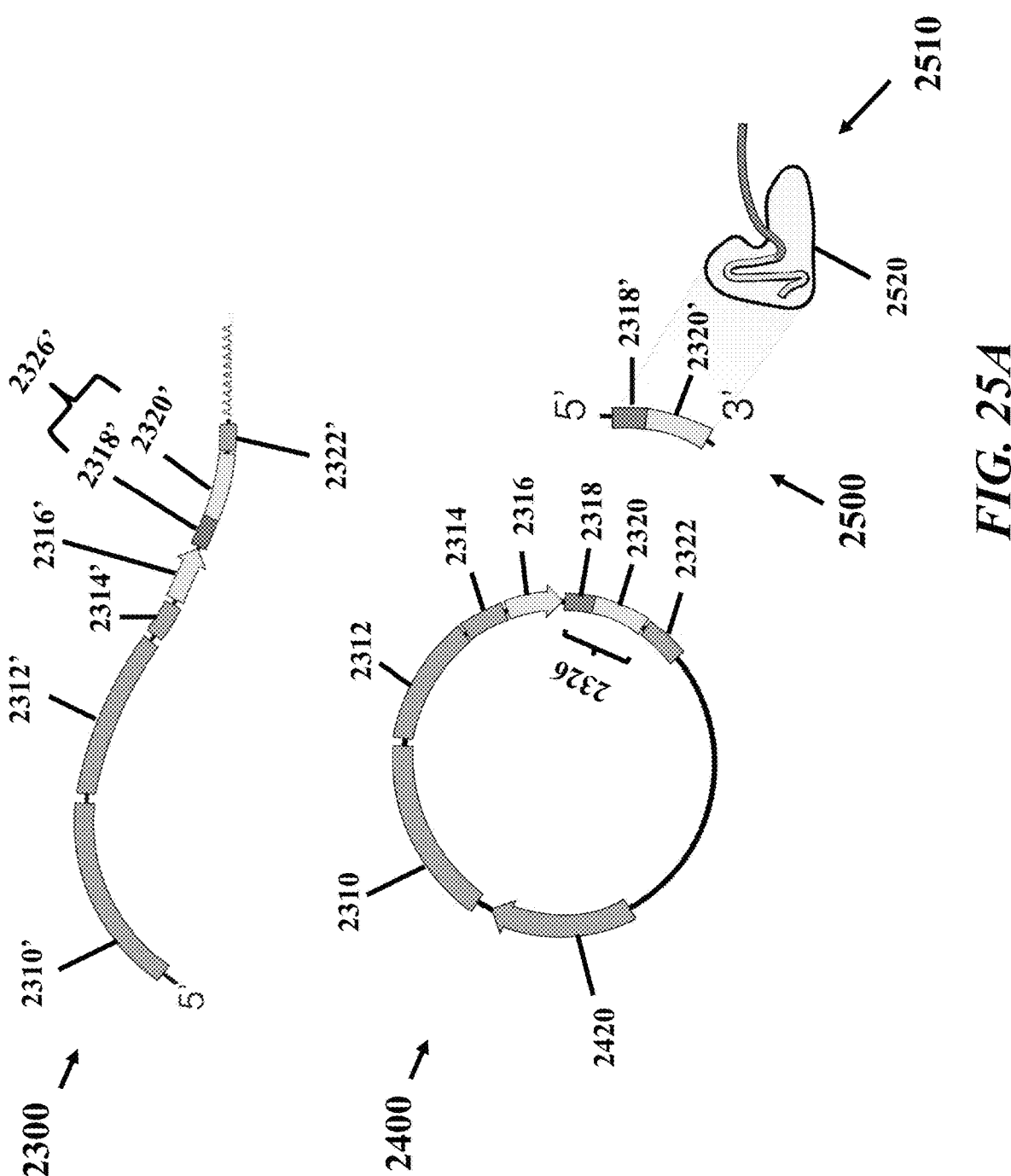
FIG. 25A shows an example plasmid expressing a polymerase III transcript and a polymerase II transcript which may be processed according to the methods of the present disclosure.

In an example, a plurality of cells is provided. The plurality of the cells is subjected to processing and analysis according to the workflows illustrated in FIG. 22 and FIG. 26 using the methods, systems, and kits provided herein. For example, a plasmid similar to plasmid 2400 shown in FIGS. 24 and 25A is constructed, e.g., using reagents and written instructions provided in a kit of the present disclosure. Methods may comprise introducing the plasmid 2400 into the plurality of cells. An RNA polymerase II can be used to transcribe, using promoter sequence 2316 of plasmid 2400, CRISPR guide 2500 comprising spacer sequence 2318' and backbone or scaffold sequence 2320'. CRISPR guide 2500 can be complexed with a CRISPR enzyme 2520 to form CRISPR complex 2510. An RNA polymerase II enzyme may transcribe plasmid 2400 using promoter 2420 (e.g., pol II promoter) to generate nucleic acid molecule 2300 in the plurality of cells. As described in further detail elsewhere herein, the nucleic acid molecule 2300 may comprise a CRISPR guide 2326' which may comprise a spacer 2318'. In some examples, the spacer 2318' may be an ssDNA. The guide 2326' may further comprise a sequence configured to bind a CRISPR enzyme (e.g., Cas9). Sequence 2320' may be a backbone or scaffold of the CRISPR guide 2326' in the nucleic acid molecule 2300. The nucleic acid molecule 2300 may comprise a promoter sequence 2316' and a poly-A tail. The systems and kits may comprise one or more nucleic scid probes (e.g., two probes). One probe may be hybridized to the scaffold 2320' in nucleic acid molecule 2300. Another probe may be hybridized to the promoter sequence 2316' in nucleic acid molecule 2300. The method may comprise performing the steps illustrated in FIG. 16. One of the probes may be extended. The extended part may include a sequence complementary to the spacer sequence. The sequence complementary to the spacer sequence may be substantially similar to the sequence of the protospacer of the target nucleic acid molecule edited using the CRISPR guide molecule and CRISPR enzyme. Extension may be facilitated by an enzyme (e.g., polymerase 1620). The two probes may ligate to one another, thereby generating the probe-linked molecule 1622. The probe-linked molecule may be barcoded according to a scheme provided elsewhere herein and be subjected to further processing and analysis leading to sequencing, determining, and/or profiling the sequence of the spacer of the CRISPR guide in the plurality of cells. For example, barcoding may be achieved by joining a barcode nucleic acid molecule with the generated a probe-linked nucleic acid molecule (e.g., via hybridization with an optional adapter molecule).

Figure 25B:
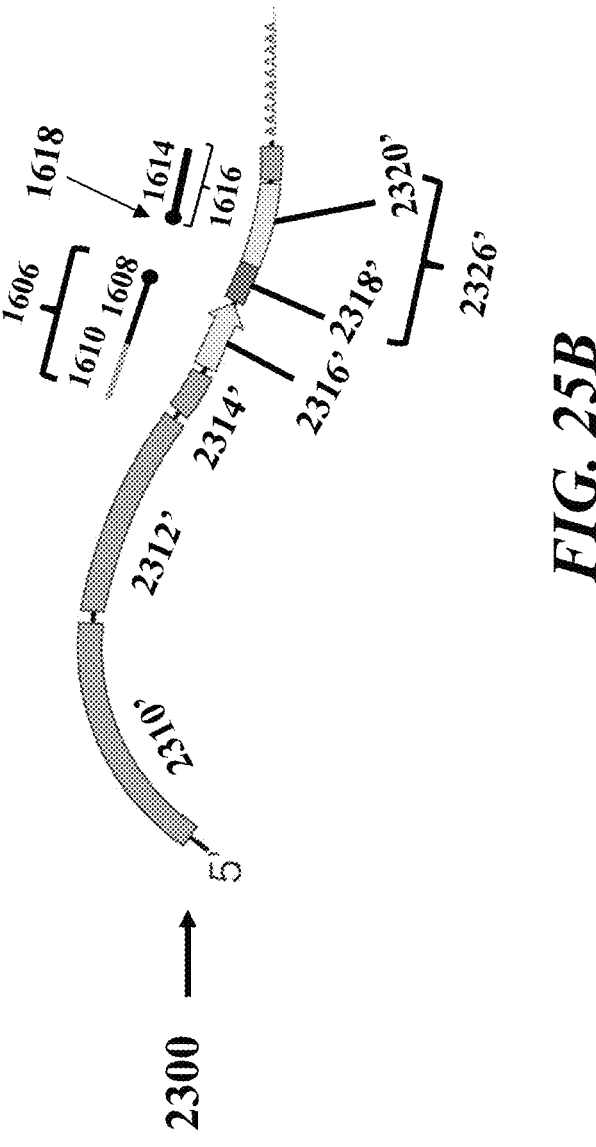
FIGS. 25B-25E show the steps of a method for analyzing a nucleic acid molecule.
Figure 25C:
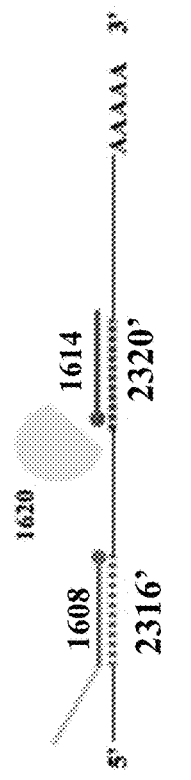
Figure 25D:
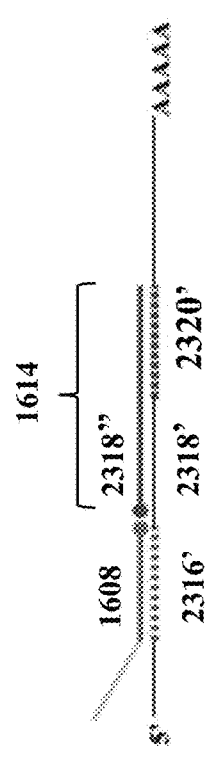
Figure 25E:
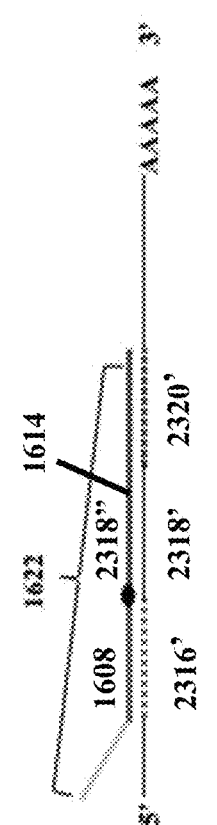

FIGS. 25B-25E show an example of analyzing nucleic acid molecule 2300 using the methods of the present disclosure, such as a method of ligating non-adjacent probes to form a probe-linked nucleic acid molecule. Sequence 1614 of probe 1616 binds to the binding region (scaffold 2320') of nucleic acid molecule 2300. Sequence 1608 of probe 1606 binds to the binding region (promoter 2316' of nucleic acid molecule 2300). As shown in FIGS. 25C and 25D, sequence 1614 of probe 1616 is extended by a polymerase 1620. The extended portion (sequence 2318") may be complementary to the spacer 2318'. The extended portion 2318" may be substantially the same as a sequence of a protospacer of a target nucleic acid. Therefore, subsequent processing and analysis of the extended portion 2318" may facilitate determining a sequence of a protospacer sequence of the target nucleic acid (i.e., a nucleic acid edited using the CRISPR guide molecule and CRISPR enzyme).

Probe 1606 comprises probe sequences 1608 and 1610 and probe 1614 comprises probe sequences 1616 and 1618. Probe sequence 1608 of probe 1606 is complementary to the promoter sequence 2316'. Similarly, probe sequence 1616 of probe 1614 is complementary to the scaffold 2320' of nucleic acid molecule 2300 and comprises a moiety 1618 onto which a polymerase may bind.

FIG. 25B shows probe sequence 1608 of probe 1606 hybridized to the promoter 2316' and probe sequence 1616 of probe 1614 hybridized to the scaffold 2320'. Probe 1614 may further comprise a sequence 3' of probe sequence 1616 that does not bind nucleic acid molecule 2300. A polymerase 1620, such as Mu polymerase or DNA polymerase, extends probe 1616 by adding complementary ribonucleotides (e.g., ribonucleoside tri-phosphate (rNTP)) or deoxyribonucleotides (e.g., deoxyribonucleotide triphosphate (dNTP)), respectively. Probe sequence 1610 of probe 1606 may be a sequence that does not bind nucleic acid molecule 2300. FIG. 25C shows probes 1606 and extended probe 1614 as adjacent to one another. FIG. 25D shows a ligation reaction of probe 1606 and extended probe 1614. Ligation may occur enzymatically, for example, by using a T4RNA ligase or a PBCV1 ligase, to form a probe-linked nucleic acid molecule 1622. The extended probe 1614 and the probe-linked nucleic acid molecule comprise sequence 2318" which is complementary to the spacer 2318' of the CRISPR guide molecule 2326'. The CRISPR guide molecule may be configured to make an edit to a target nucleic acid in the cell, such as at a protospacer sequence which is substantially complementary to the spacer sequence 2318' and substantially the same as the extended sequence 2318" (the extended portion of the probe). Processing and detecting the sequence of the extended sequence 2318" facilitates determining the sequence of the protospacer of the target nucleic acid molecule. This method can be applied to a large number of cells in a high-throughput RNA-seq or CROP-seq assay and determine the sequence of protospacer in a larger number of nucleic acids in a plurality of cells. Downstream analysis may subsequently be performed, such as barcoding and amplification, similar to as shown in FIGS. 12D-12F or according to any other method or system described or illustrated elsewhere herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing nucleic acid molecules, comprising:
   (a) providing a plurality of nucleic acid molecules each comprising:
      i) a constant upstream binding region,
      ii) a variable region comprising a sequence encoding a CRISPR guide molecule or a barcode sequence that identifies the CRISPR guide molecule, and
      iii) a constant downstream binding region;
   (b) hybridizing a plurality of first nucleic acid probes to constant upstream binding regions of the plurality of nucleic acid molecules, and a plurality of second nucleic acid probes to constant downstream binding regions of the plurality of nucleic acid molecules;
   (c) extending a 3' end of a second nucleic acid probe of the plurality of second nucleic acid probes hybridized to a nucleic acid molecule of the plurality of nucleic acid molecules to generate an extension product comprising a sequence complementary to the variable region; and
   (d) ligating a 3' end of the extension product to a 5' end of a first nucleic acid probe of the plurality of first nucleic acid probes hybridized to the nucleic acid molecule to generate a probe-linked nucleic acid molecule hybridized to the nucleic acid molecule.

2. The method of claim 1, wherein the variable region comprises a spacer sequence of the CRISPR guide molecule.

3. The method of claim 1, wherein (a) comprises providing a plurality of cells comprising the plurality of nucleic acid molecules.

4. The method of claim 1, wherein the first nucleic acid probe and/or the second nucleic acid probe comprises a barcode sequence.

5. The method of claim 1, wherein the constant downstream binding region comprises a CRISPR enzyme binding sequence.

6. The method of claim 1, wherein a nucleic acid molecule of the plurality of nucleic acid molecules comprises a deoxyribonucleic acid (DNA) molecule, wherein the DNA molecule is a plasmid, and wherein the plasmid comprises a long terminal repeat sequence.

7. The method of claim 6, wherein the long terminal repeat sequence comprises the variable region comprising the sequence encoding the CRISPR guide molecule or the barcode sequence that identifies the CRISPR guide molecule.

8. The method of claim 1, wherein a nucleic acid molecule of the plurality of nucleic acid molecules comprises a ribonucleic acid (RNA) molecule.

9. The method of claim 8, wherein the RNA molecule comprises a 3' untranslated region, which comprises the variable region comprising the sequence encoding the CRISPR guide molecule or the barcode sequence that identifies the CRISPR guide molecule.

10. The method of claim 1, further comprising coupling a nucleic acid barcode molecule to the probe-linked nucleic acid molecule to generate a barcoded nucleic acid molecule.

11. The method of claim 10, wherein the coupling is performed in a partition, wherein the partition is a droplet or a well.

12. The method of claim 10, further comprising sequencing the barcoded nucleic acid molecule, or an amplification product thereof.

13. The method of claim 12, further comprising determining a sequence of the variable region comprising the sequence encoding the CRISPR guide molecule or the barcode sequence that identifies the CRISPR guide molecule, or a sequence complementary thereto in the barcoded nucleic acid molecule, or an amplification product thereof.

14. A kit comprising (a) a plurality of nucleic acid molecules, each comprising:
  i) a constant upstream binding region,
  ii) a variable region comprising a sequence encoding a CRISPR guide molecule or a barcode sequence that identifies the CRISPR guide molecule, and
  iii) a constant downstream binding region,
(b) a first nucleic acid probe configured to hybridize to the constant upstream binding region of a nucleic acid molecule of the plurality of nucleic acid molecules;

(c) a second nucleic acid probe configured to hybridize to the constant downstream binding region of the nucleic acid molecule; and
(d) a support comprising a plurality of nucleic acid barcode molecules.

15. The kit of claim 14, wherein the nucleic acid molecule comprises a deoxyribonucleic acid (DNA) molecule.

16. The kit of claim 14, wherein the nucleic acid molecule comprises a ribonucleic acid (RNA) molecule.

17. The kit of claim 16, wherein the RNA molecule comprises a CRISPR spacer sequence.

18. The kit of claim 17, wherein the kit further comprises:
a polymerase configured to extend a 3' end of the second nucleic acid probe when the second nucleic acid probe is hybridized to the nucleic acid molecule; and
a ligase configured to ligate a 3' end of an extension product generated by extension of the second nucleic acid probe by the polymerase to a 5' end of the first nucleic acid probe when the first nucleic acid probe is hybridized to the nucleic acid molecule to generate a probe-linked nucleic acid molecule hybridized to the nucleic acid molecule.

19. The kit of claim 18, wherein the first nucleic acid probe of the probe-linked nucleic acid molecule comprises an overhang sequence configured to hybridize to a nucleic acid barcode molecule of the plurality of nucleic acid barcode molecules.

20. The method of claim 3, wherein (d) occurs in a cell of the plurality of cells.

21. The method of claim 20, wherein the method further comprises providing a partition comprising the cell and a plurality of nucleic acid barcode molecules comprising a partition-specific barcode sequence, wherein the partition is a droplet or a well.

22. The method of claim 21, wherein the method further comprises generating a barcoded nucleic acid molecule using a nucleic acid barcode molecule of the plurality of nucleic acid barcode molecules and the probe-linked nucleic acid molecule in the partition, wherein the barcoded nucleic acid molecule comprises: 1) the partition-specific barcode sequence or a complement thereof, and 2) a sequence of the probe-linked nucleic acid molecule or a complement thereof.

23. The method of claim 22, wherein the method further comprises sequencing the barcoded nucleic acid molecule or a derivative thereof.

24. The method of claim 23, wherein the method further comprises determining a sequence of the variable region and the partition-specific barcode sequence using results of the sequencing.

* * * * *